United States Patent [19]
Hohla

[11] Patent Number: 6,090,100
[45] Date of Patent: Jul. 18, 2000

[54] EXCIMER LASER SYSTEM FOR CORRECTION OF VISION WITH REDUCED THERMAL EFFECTS

[75] Inventor: Kristian Hohla, Vaterstetten, Germany

[73] Assignee: Chiron Technolas GmbH Ophthalmologische Systeme, Munich, Germany

[21] Appl. No.: 08/324,782

[22] Filed: Oct. 18, 1994

Related U.S. Application Data

[63] Continuation-in-part of application No. 08/224,751, Apr. 8, 1994, which is a continuation-in-part of application No. PCT/EP93/02667, Sep. 30, 1993, abandoned.

[30] Foreign Application Priority Data

Oct. 1, 1992 [DE] Germany .......................... 42 32 915

[51] Int. Cl.$^7$ .................................................. A61N 5/06
[52] U.S. Cl. ................................ 606/5; 606/3; 606/10; 606/11; 606/13
[58] Field of Search .......................... 606/2, 3–6, 10–14

[56] References Cited

U.S. PATENT DOCUMENTS

| | | | |
|---|---|---|---|
| 4,469,098 | 9/1984 | Davi | 606/7 |
| 4,665,913 | 5/1987 | L'Esperance, Jr. | 606/3 |

(List continued on next page.)

FOREIGN PATENT DOCUMENTS

| | | |
|---|---|---|
| 9348198 | 9/1993 | Australia . |
| 111 060 | 9/1983 | European Pat. Off. . |
| 151 869 | 11/1984 | European Pat. Off. . |
| 164 858 | 4/1985 | European Pat. Off. . |
| 191 688 | 1/1986 | European Pat. Off. . |

(List continued on next page.)

OTHER PUBLICATIONS

*Variations on a Dither Algorithm*, ©Eurographics Association, 1989, Elsevier Science Publishers B.V.).
*Rasterfahndung*, MC–Extra, Aug. 1994, pp. 20–28 no translation.
*Darf es etwas weniger sein?*, MC–Extra, Jun. 1994, pp. 92–99 no translation.

(List continued on next page.)

*Primary Examiner*—David M. Shay
*Attorney, Agent, or Firm*—Akin, Gump, Strauss, Hauer & Feld, LLP

[57] ABSTRACT

A apparatus and method for controlling an apparatus for removing tissue from the eye performs various types of corrections using a relatively large beam, but oscillating, or dithering, that being to prevent reinforcing ridges from being formed during the tissue removal process. Further, various types of correction, such as hyperopia and astigmatism correction, are performed using a large beam that is scanned over the area to be ablated using overlapping shots. Further, the epithelium in the area to be treated is removed using an infrared fluorescent dye to dye the epithelium, and then observing the fluorescent patterns from the epithelium area to be removed. Once a certain area is no longer fluorescent after laser shots, smaller shots are then applied, selectively removing the epithelium from the remaining regions. Again, the fluorescence patterns are observed, and the process is repeated until no epithelium remains. At this point, all of the epithelium is removed, and further a map is created of the initial epithelial thickness at each point in the area from which the epithelium was removed. Using two astigmatism correcting ablation patterns intersecting at an angle, a lens is created capable of correcting for myopia, hyperopia, and astigmatism. Further, overlapping shots using a relatively large fixed spot size provide for reduced thermal heating, ridgeless treatment patterns, reduced shot count, and simplified equipment.

23 Claims, 29 Drawing Sheets

U.S. PATENT DOCUMENTS

| | | |
|---|---|---|
| 4,669,466 | 6/1987 | L'Esperance . |
| 4,695,163 | 9/1987 | Schachar . |
| 4,718,418 | 1/1988 | L'Esperance, Jr. . |
| 4,729,372 | 3/1988 | L'Esperance, Jr. . |
| 4,731,516 | 3/1988 | Noguchi et al. . |
| 4,732,148 | 3/1988 | L'Esperance, Jr. . |
| 4,737,628 | 4/1988 | Lovoi .................................. 606/7 |
| 4,770,172 | 9/1988 | L'Esperance, Jr. . |
| 4,773,414 | 9/1988 | L'Esperance, Jr. . |
| 4,784,135 | 11/1988 | Blum et al. . |
| 4,788,975 | 12/1988 | Shturman et al. . |
| 4,798,204 | 1/1989 | L'Esperance, Jr. . |
| 4,887,019 | 12/1989 | Reis et al. . |
| 4,911,711 | 3/1990 | Telfair et al. . |
| 4,925,523 | 5/1990 | Braren et al. . |
| 4,941,093 | 7/1990 | Marshall et al. . |
| 4,953,969 | 9/1990 | Fedorov . |
| 4,973,330 | 11/1990 | Azema et al. . |
| 5,061,342 | 10/1991 | Jones .................................. 156/643 |
| 5,108,388 | 4/1992 | Trokel . |
| 5,170,191 | 12/1992 | Jones . |
| 5,240,553 | 8/1993 | Jones . |
| 5,336,217 | 8/1994 | Buys et al. ............................ 606/2 |
| 5,520,679 | 5/1996 | Lin . |
| 5,548,352 | 8/1996 | Dewey . |
| 5,569,238 | 10/1996 | Shei et al. . |
| 5,599,340 | 2/1997 | Simon et al. . |

FOREIGN PATENT DOCUMENTS

| | | |
|---|---|---|
| 0 247 260 | 5/1986 | European Pat. Off. . |
| 0 209 992 | 6/1986 | European Pat. Off. . |
| 207 648 | 6/1986 | European Pat. Off. . |
| 224 322 | 9/1986 | European Pat. Off. . |
| 257 836 | 7/1987 | European Pat. Off. . |
| 280 414 | 1/1988 | European Pat. Off. . |
| 306 409 | 1/1988 | European Pat. Off. . |
| 296 982 | 6/1988 | European Pat. Off. . |
| 299 836 | 6/1988 | European Pat. Off. . |
| 326 760 | 12/1988 | European Pat. Off. . |
| 346 116 | 6/1989 | European Pat. Off. . |
| 356 282 | 7/1989 | European Pat. Off. . |
| 400 471 | 5/1990 | European Pat. Off. . |
| 412 789 | 8/1990 | European Pat. Off. . |
| 412 798 | 8/1990 | European Pat. Off. . |
| 447 067 | 2/1991 | European Pat. Off. . |
| 0 503 802 A1 | 2/1992 | European Pat. Off. . |
| 657 151 | 6/1995 | European Pat. Off. . |
| WO 91/08723 | 6/1991 | France . |
| 1 040 181 | 10/1954 | Germany . |
| 31 48 748 | 12/1981 | Germany . |
| 35 32 464 | 9/1985 | Germany . |
| 3615042 | 11/1987 | Germany . |
| 4001434 | 8/1990 | Germany . |
| 41 41 890 | 2/1992 | Germany . |
| 43 37 842 | 5/1994 | Germany . |
| 58-163589 | 9/1983 | Japan . |
| WO 86/02730 | 5/1986 | WIPO . |
| WO 90/09141 | 8/1990 | WIPO . |
| WO 90/11054 | 10/1990 | WIPO . |
| WO 91/19539 | 12/1991 | WIPO . |
| WO 92/01430 | 2/1992 | WIPO . |
| WO 93/08877 | 5/1993 | WIPO . |
| WO 94/01904 | 7/1993 | WIPO . |
| WO 94/07447 | 9/1993 | WIPO . |

OTHER PUBLICATIONS

Thompson, Frank B. and McDonnell, Peter J., "Color Atlas/Text of Excimer Laser Surgery: The Cornea", 1993 Igaku–Shoin Medical Publishers, Inc., pp. 30–33; 41; 53–62; 77–92; 93–103; 137–151.

Sher, et al., "Clinical Use of the 193–nm Excimer Laser in the Treatment of Corneal Scars," Arch Ophthalmol–vol. 109, Apr. 1991, pp. 491–498.

L'Esperance, et al., "Excimer Laser Instrumentation and Technique for Human Corneal Surgery," Arch Ophthalmol–vol. 107, Jan. 1989, pp. 131–139.

Hanna, et al., "Excimer Laser Keratectomy for Myopia with a Rotating–Slit Delivery System," Arch Ophthalmol–vol. 106, Feb. 1988, pp. 245–250.

McDonnell, et al., "Photorefractive Keratectomy to Create Toric Ablations for Correction of Astigmatism," Arch Ophthalmol–vol. 109, Mar. 1991, pp. 710–713.

Trokel, et al., "Excimer Laser Surgery of the Cornea," AM. J. Ophthalmology 96:710–715, 1983.

"Selective Photothermolysis: Precise Microsurgery by Selective Absorption of Pulsed Radiation"by Anderson et al; Science; vol. 220; Apr. 1983 pp. 524–527.

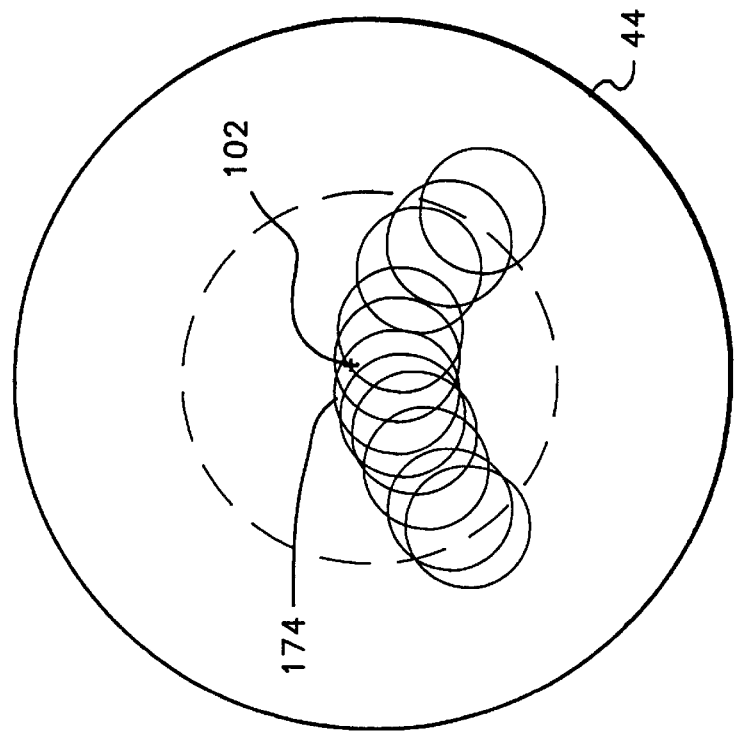
FIG. 5
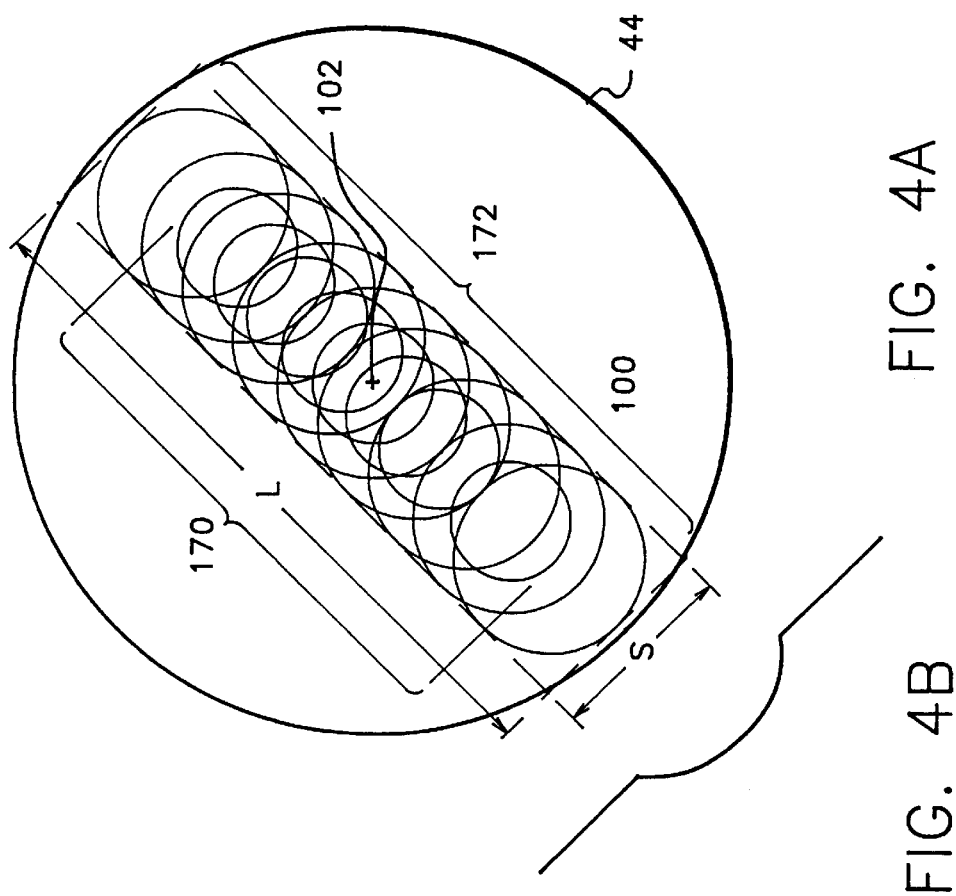
FIG. 4A
FIG. 4B

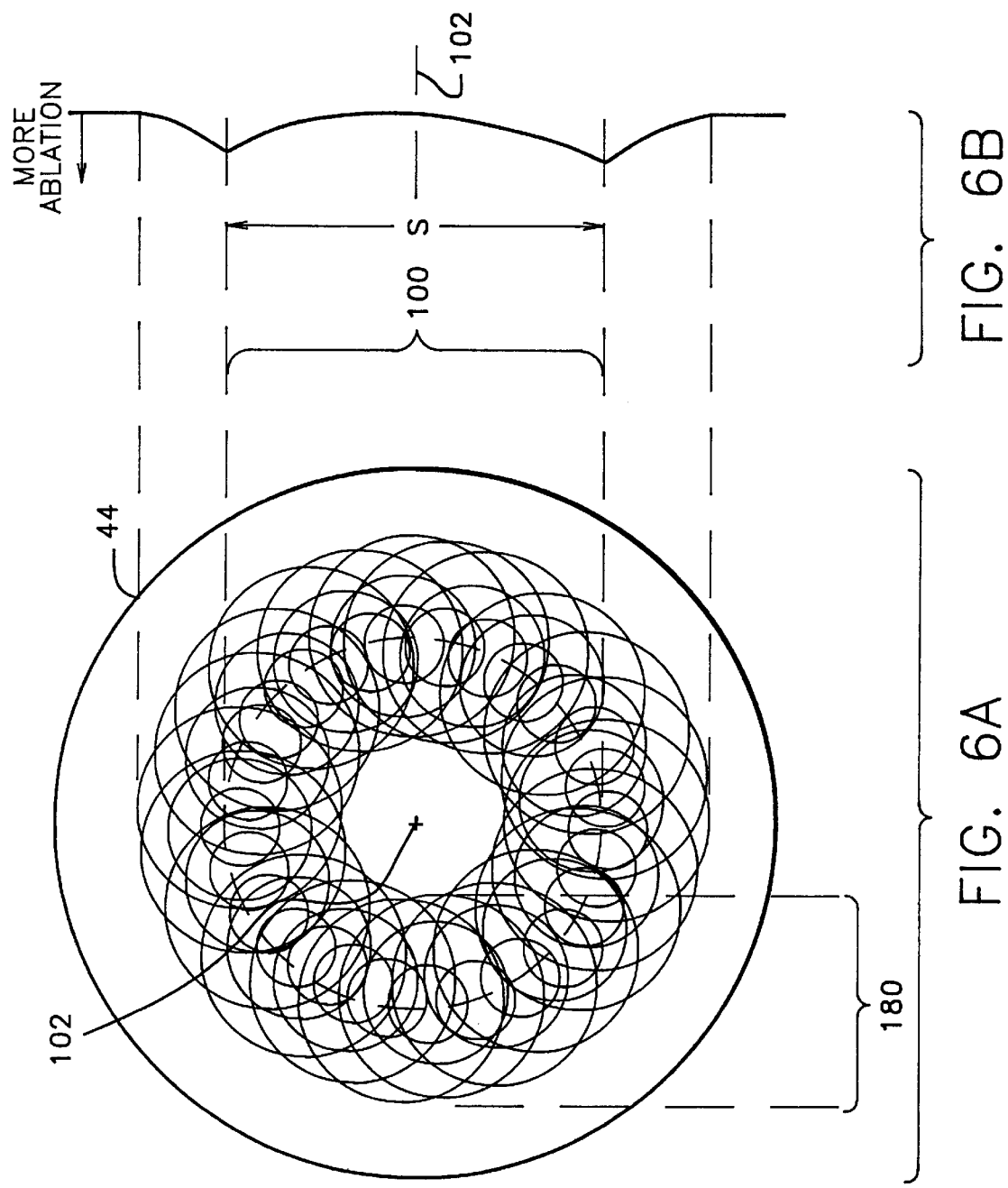

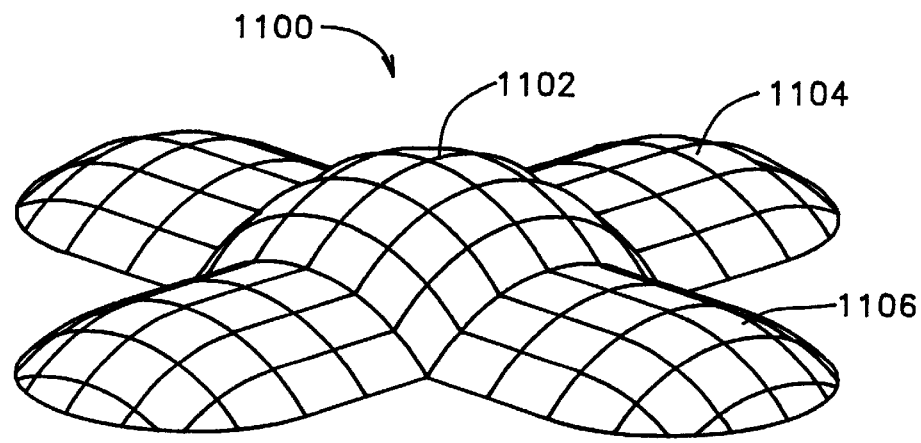
FIG. 17
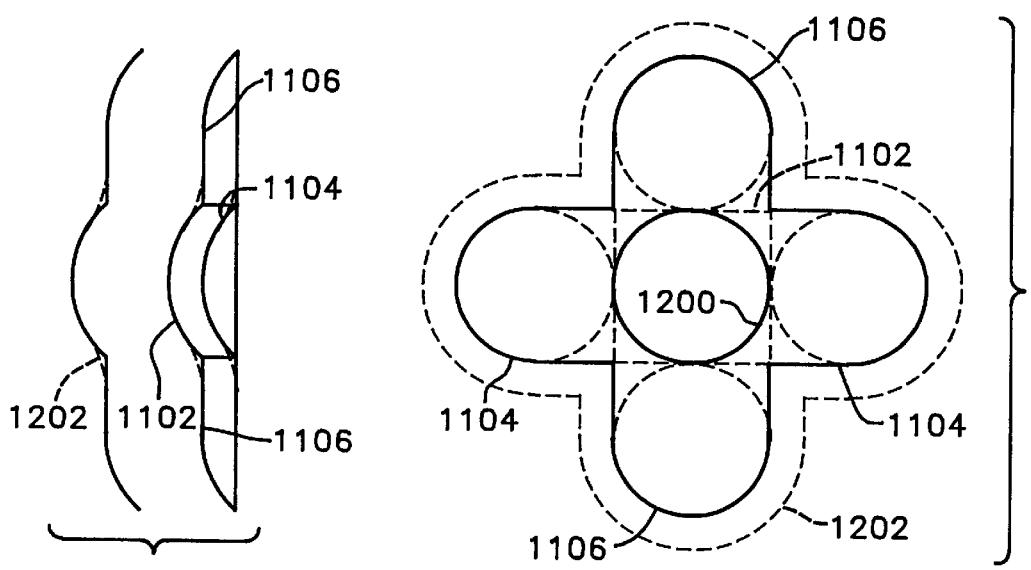
FIG. 18C
FIG. 18A
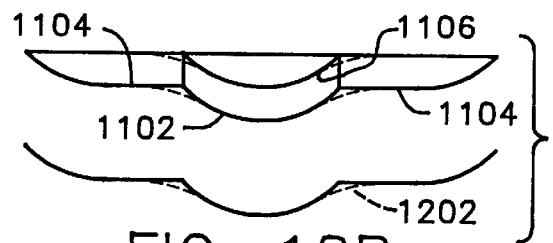
FIG. 18B

| No. | x_pos | y_pos | No. | x_pos | y_pos | No. | x_pos | y_pos |
|---|---|---|---|---|---|---|---|---|
| 5 | -1953 | 0 | 116 | -793 | -562 | 106 | -364 | 955 |
| 22 | -1665 | -331 | 130 | -789 | 380 | 215 | -360 | 104 |
| 14 | -1664 | -689 | 146 | -779 | -44 | 193 | -343 | -343 |
| 13 | -1664 | 689 | 78 | -738 | -981 | 199 | -343 | 343 |
| 30 | -1580 | 314 | 122 | -706 | 596 | 155 | -336 | -650 |
| 46 | -1461 | 123 | 154 | -697 | -222 | 20 | -331 | 1665 |
| 38 | -1450 | 507 | 15 | -689 | -1664 | 216 | -328 | -181 |
| 21 | -1412 | 943 | 12 | -689 | 1664 | 32 | -314 | -1580 |
| 39 | -1384 | -666 | 139 | -688 | -460 | 223 | -314 | 9 |
| 54 | -1382 | -235 | 91 | -675 | 897 | 129 | -289 | 827 |
| 6 | -1381 | -1381 | 101 | -668 | -838 | 178 | -283 | -513 |
| 4 | -1381 | 1381 | 161 | -667 | 152 | 191 | -272 | 462 |
| 31 | -1339 | -895 | 37 | -666 | 1384 | 231 | -241 | -55 |
| 69 | -1276 | 144 | 153 | -650 | 336 | 52 | -235 | 1382 |
| 61 | -1254 | 479 | 169 | -636 | -18 | 224 | -228 | -216 |
| 62 | -1225 | -548 | 124 | -598 | -706 | 160 | -222 | 697 |
| 77 | -1216 | -172 | 145 | -582 | 520 | 201 | -218 | -370 |
| 53 | -1143 | 811 | 162 | -579 | -364 | 222 | -216 | 228 |
| 47 | -1120 | -946 | 177 | -563 | -162 | 230 | -209 | 131 |
| 92 | -1112 | 157 | 114 | -562 | 793 | 214 | -181 | 328 |
| 85 | -1086 | -450 | 60 | -548 | 1225 | 75 | -172 | 1216 |
| 84 | -1086 | 450 | 147 | -520 | -582 | 117 | -163 | -958 |
| 100 | -1065 | -120 | 192 | -519 | 134 | 140 | -162 | -812 |
| 70 | -1004 | -801 | 184 | -513 | 283 | 183 | -162 | 563 |
| 76 | -981 | 738 | 40 | -507 | -1450 | 238 | -160 | 51 |
| 115 | -958 | 163 | 200 | -485 | 0 | 94 | -157 | -1112 |
| 108 | -955 | -364 | 63 | -479 | -1254 | 163 | -152 | -667 |
| 45 | -946 | 1120 | 185 | -462 | -272 | 239 | -149 | -77 |
| 23 | -943 | -1412 | 176 | -462 | 437 | 71 | -144 | -1276 |
| 107 | -933 | 417 | 137 | -460 | 688 | 186 | -134 | -519 |
| 123 | -921 | -78 | 86 | -450 | -1086 | 232 | -131 | -209 |
| 93 | -897 | -675 | 83 | -450 | 1086 | 48 | -123 | -1461 |
| 29 | -895 | 1339 | 170 | -437 | -462 | 98 | -120 | 1085 |
| 99 | -838 | 668 | 109 | -417 | -933 | 206 | -107 | 416 |
| 131 | -827 | -289 | 208 | -416 | -107 | 209 | -104 | -360 |
| 138 | -812 | 162 | 132 | -380 | -789 | 121 | -78 | 921 |
| 55 | -811 | -1143 | 207 | -370 | 218 | 237 | -77 | 149 |
| 68 | -801 | 1004 | 168 | -364 | 579 | 229 | -65 | 241 |

FIG. 24A

| No. | x_pos | y_pos | No. | x_pos | y_pos | No. | x_pos | y_pos |
|---|---|---|---|---|---|---|---|---|
| 240 | -51 | -160 | 113 | 163 | 958 | 151 | 520 | 582 |
| 152 | -44 | 779 | 79 | 172 | -1216 | 64 | 548 | -1225 |
| 246 | -31 | 2 | 210 | 181 | -328 | 118 | 562 | -793 |
| 247 | -23 | -21 | 226 | 209 | -131 | 181 | 563 | 162 |
| 245 | -21 | 23 | 218 | 216 | -228 | 166 | 579 | 364 |
| 175 | -18 | 636 | 205 | 218 | 370 | 149 | 582 | -520 |
| 250 | -15 | 10 | 156 | 222 | -697 | 128 | 596 | 706 |
| 217 | -9 | -314 | 220 | 228 | 216 | 173 | 636 | 18 |
| 248 | -2 | -31 | 56 | 235 | -1382 | 157 | 650 | -336 |
| 7 | 0 | -1953 | 227 | 241 | 55 | 33 | 666 | -1384 |
| 194 | 0 | -485 | 187 | 272 | -462 | 165 | 667 | -152 |
| 198 | 0 | 485 | 182 | 283 | 513 | 97 | 668 | 838 |
| 3 | 0 | 1953 | 133 | 289 | -827 | 95 | 675 | -897 |
| 244 | 2 | 31 | 219 | 314 | -9 | 143 | 688 | -460 |
| 221 | 9 | 314 | 28 | 314 | 1580 | 16 | 689 | -1664 |
| 249 | 15 | -10 | 212 | 328 | 181 | 11 | 689 | 1664 |
| 171 | 18 | -636 | 24 | 331 | -1665 | 158 | 697 | 222 |
| 241 | 21 | -23 | 159 | 336 | 650 | 126 | 706 | -596 |
| 243 | 23 | 21 | 195 | 343 | -343 | 74 | 738 | 981 |
| 242 | 31 | -2 | 197 | 343 | 343 | 150 | 779 | 44 |
| 148 | 44 | -779 | 211 | 360 | -104 | 134 | 789 | -380 |
| 236 | 51 | 160 | 110 | 364 | -955 | 120 | 793 | 562 |
| 225 | 55 | -241 | 164 | 364 | -579 | 72 | 801 | -1004 |
| 233 | 77 | -149 | 203 | 370 | -218 | 51 | 811 | 1143 |
| 125 | 78 | -921 | 136 | 380 | 789 | 142 | 812 | -162 |
| 213 | 104 | 360 | 204 | 416 | 107 | 135 | 827 | 289 |
| 202 | 107 | -416 | 105 | 417 | 933 | 103 | 838 | -668 |
| 102 | 120 | -1065 | 174 | 437 | 462 | 25 | 895 | -1339 |
| 44 | 123 | 1461 | 87 | 450 | -1086 | 89 | 897 | 675 |
| 228 | 131 | 209 | 82 | 450 | 1086 | 127 | 921 | 78 |
| 190 | 134 | 519 | 141 | 460 | -688 | 111 | 933 | -417 |
| 67 | 144 | 1276 | 172 | 462 | -437 | 19 | 943 | 1412 |
| 235 | 149 | 77 | 189 | 462 | 272 | 41 | 946 | -1120 |
| 167 | 152 | 667 | 59 | 479 | 1254 | 112 | 955 | 364 |
| 90 | 157 | 1112 | 196 | 485 | 0 | 119 | 958 | -163 |
| 234 | 160 | -51 | 36 | 507 | 1450 | 80 | 981 | -738 |
| 179 | 162 | -563 | 180 | 513 | -283 | 86 | 1004 | 801 |
| 144 | 162 | 812 | 188 | 519 | -134 | 104 | 1065 | 120 |

FIG. 24B

| No. | x_pos | y_pos |
|---|---|---|
| 88 | 1086 | -450 |
| 81 | 1086 | 450 |
| 96 | 1112 | -157 |
| 43 | 1120 | 946 |
| 49 | 1143 | -811 |
| 73 | 1216 | 172 |
| 58 | 1225 | 548 |
| 57 | 1254 | -479 |
| 65 | 1276 | -144 |
| 27 | 1339 | 895 |
| 8 | 1381 | -1381 |
| 2 | 1381 | 1381 |
| 50 | 1382 | 235 |
| 35 | 1384 | 666 |
| 17 | 1412 | -943 |
| 34 | 1450 | -507 |
| 42 | 1461 | -123 |
| 26 | 1580 | -314 |
| 9 | 1664 | -689 |
| 10 | 1664 | 689 |
| 18 | 1665 | 331 |
| 1 | 1953 | 0 |

FIG. 24C

EXCIMER LASER SYSTEM FOR CORRECTION OF VISION WITH REDUCED THERMAL EFFECTS

This application is a continuation-in-part of U.S. patent application Ser. No. 08/224,751 filed on Apr. 8, 1994, abandoned which is in turn a continuation-in-part of PCT Application No. EP93/02667 filed on Sep. 30, 1993, and designating the Untied States, which in turn claims priority to German application no. P 42 32 915.9 filed on Oct. 1, 1992.

BACKGROUND OF THE INVENTION

1. Field of the Invention

The invention relates to an apparatus for surgically modifying the curvature of the eye cornea and a method of controlling the apparatus, and more particularly to an apparatus for smoothly correcting a variety of corneal defects using a large, fixed spot size in an overlapping pattern that reduces thermal effects.

2. Description of the Related Art

Since the initial development of corrective lenses, 20 new and better ways of correcting defective eyesight have been developed. From the bifocal lens and extended wear soft contact lens to corneal incisions and shaping, the field of ophthalmology has seen great advances in convenience, safety, and accuracy in correcting a variety of sight defects, including myopia, hyperopia, and astigmatism.

While corrective lenses still find wide general application, ophthalmologists are focussing on surgery to correct such defects. One of the most popular surgical techniques is radial keratotomy, in which a surgeon forms radial slits in the outer surface of the cornea, allowing the cornea to re-shape and resulting in a modified cornea to correct the deficiencies of the patient's sight. This technique has continued to develop, but the advent of the laser and its introduction into the field of medicine have given rise to a new and potentially revolutionary method of eye surgery. Specifically, the development of the excimer laser and its application to eye surgery has opened a new approach to ophthalmological surgery.

The excimer laser produces coherent light of a very short wavelength of around 193 nm. At these wavelengths and the resulting high energies, the excimer laser removes, or ablates, tissue at the molecular level without significant heating of adjacent tissue. Thus, rather than "burning" away tissue, the excimer laser literally breaks the molecular bonds, and the ablated tissue is ejected from the ablated surface leaving a relatively unmarred surface to heal virtually scar-free. This aspect of the excimer laser is now well known and is further described, for example, in U.S. Pat. No. 4,784,135 entitled "Far Ultraviolet Surgical and Dental Procedures," issued Nov. 15, 1988.

The word "excimer" in excimer laser was initially drawn from its molecular principal of operation. The excimer laser was initially based on the lasing action of excited dimers, such as xenon, krypton, or fluorine in the form of $Xe_2$, $Kr_2$, or $F_2$. The word "excimer" as applied to lasers is now a misnomer, as the most popular excimer laser used in eye surgery does not even use dimers—it uses argon fluoride. The excimer laser is also a pumped laser, in the sense that another laser is used to stimulate the lasing action of the argon fluoride mixture in the laser cavity. "Excimer laser" has now come to be applied to an entire group of lasers with ultraviolet wavelengths below 400 nm.

When used in ophthalmological surgery, the excimer laser is preferably pulsed, as that allows for application of high energies without thermal heating. These pulses are very short bursts of high energy laser light applied to the cornea. For example, such a laser is typically pulsed at between 1 to 50 Hz with a 10 to 20 ns pulse duration. A drawback of the excimer laser, however, is the energy density over the beam tends to have both large and small scale inhomogeneities. The application of the excimer laser for surgical procedures is described in U.S. Pat. No. 4,784,135, entitled "Far Ultraviolet Surgical and Dental Procedures," issued Nov. 15, 1988. For a historical background of the development and application of the excimer laser to ophthalmic surgery, see Chapter 1 of the Color Atlas/Text of Excimer Laser Surgery, © 1993 Igaku-Shoin Medical Publishers, Inc.

As early as 1983, researchers recognized the potential application of excimer laser light in reshaping the cornea. Since that time, a number of systems have been developed to reshape the cornea, using a variety of techniques such as variable sized circular apertures to correct for myopia, variable sized ring shaped apertures to correct for hyperopia, and variable sized slit shaped apertures to correct for astigmatism. These techniques collectively came to be known as photorefractive keratectomy. It has been recognized that using such apertures to correct for myopia, for example, a series of excimer laser shots using progressively smaller spot sizes could ablate away a portion of the cornea to effectively build a "corrective lens" into the cornea. These techniques are discussed, for example, in U.S. Pat. No. 4,973,330, entitled "Surgical Apparatus for Modifying the Curvature of the Eye Cornea," issued Nov. 27, 1990, and in U.S. Pat. No. 4,729,372, entitled "Apparatus for Performing Ophthalmic Laser Surgery," issued Mar. 8, 1988. Those skilled in the art of laser ophthalmological surgery have extensively developed the required exposure patterns using these variable size apertures to provide an appropriate amount of correction to various degrees of myopia, hyperopia, and astigmatism, and a combination of these conditions.

These multiple aperture systems, however, suffer a number of drawbacks. They tend to be complicated and inflexible, requiring a number of aperture wheels or masks and only providing standard forms of correction for myopia and hyperopia with circular symmetry and astigmatism with cylindrical symmetry. The human eye, however, tends to have more subtle defects. A system that could accommodate these defects and provide more adaptable solutions, as well as a physically simpler components, would thus be advantageous.

An apparatus for ablating tissue from the eye is shown in U.S. Pat. No. 4,973,330, referenced above. This apparatus includes an excimer laser, the laser beam of which impinges on the cornea, with the axis of the laser beam coinciding with the optical axis of the eye. Furthermore, a field stop limits the area of the laser spot on the cornea illuminated by the laser beam, and the size of this field stop is set in a temporarily variable manner according to the profile of the area to be removed so that the thickness of the area to be removed is a function of the distance from the optical axis of the eye.

The system described in U.S. Pat. No. 4,973,330 permits in this way setting the "laser energy deposited" on the cornea as the function of the distance from the optical axis of the eye, but only under the condition that the distribution of energy (i.e., the power of the laser beam spot) is homogeneous, or at least axially symmetrical. This, however, is a condition that excimer lasers in particular do not always fulfill. Inhomogeneous power distribution results in non-axially symmetrical removal. Moreover, the system described in U.S. Pat. No. 4,973,330 only permits the correction of spherical aberrations, not astigmatism.

An apparatus based on the same fundamental idea is known from U.S. Pat. No. 4,994,058, entitled "Surface Shaping Using Lasers", issued Feb. 19, 1991. That apparatus employs a "destructible field stop mask" instead of a field stop having a temporarily variable aperture.

Another class of apparatus for shaping the cornea by means of removing tissue is known from the various L'Esperance patents. These include U.S. Pat. No. 4,665,913, entitled "Method for Ophthalmological Surgery," issued May 19, 1987; U.S. Pat. No. 4,669,466, entitled "Method and Apparatus for Analysis and Correction of Abnormal Refractive Errors of the Eye," issued Jun. 2, 1987; U.S. Pat. No. 4,718,418, entitled "Apparatus for Ophthalmological Surgery," issued Jan. 12, 1988; U.S. Pat. No. 4,721,379, entitled "Apparatus for Analysis and Correction of Abnormal Refractive Errors of the Eye," issued Jan. 26, 1988; U.S. Pat. No. 4,729,372, entitled "Apparatus for Performing Ophthalmic Laser Surgery," issued Mar. 8, 1988; U.S. Pat. No. 4,732,148, entitled "Method for Performing Ophthalmic Laser Surgery," issued Mar. 22, 1988; U.S. Pat. No. 4,770,172, entitled "Method of Laser-Sculpture of the Optically used Portion of the Cornea," issued Sep. 13, 1988; U.S. Pat. No. 4,773,414, entitled "Method of Laser-Sculpture of the Optically used Portion of the Cornea," issued Sep. 27, 1988; and U.S. Pat. No. 4,798,204, entitled "Method of Laser-Sculpture of the Optically used Portion of the Cornea," issued Jan. 17, 1989. In that apparatus, a laser beam with a small focus spot is moved by a two-dimensional scanning system over the area to be removed. This apparatus, which operates as a "scanner," has the advantage that it can generate any two-dimensional profile of deposited energy "over the area to be removed." Because of the small size of the beam spot, the period of treatment, however, is very great, as power per area unit cannot be raised above a specific "critical" value.

Thus, current techniques do not adequately address the non-linear energy distribution of an excimer laser. The excimer laser includes both large scale and small scale non-linearities in its energy distribution. This can cause over-ablation and under-ablation of certain areas of the eye under treatment. Thus it would be desirable to provide a system that further homogenizes the effective energy deposited on the eye.

Systems that use apertures to create a series of progressively smaller shot sizes also suffer from the disadvantage of creating sharp ridges in the treatment zone of the cornea. Especially near the periphery of the treatment zone, a number of shots are typically required to create the necessary ablation depth at each particular spot size. The typical ablation depth for each shot is 0.2 μm. When multiple shots are required at a single aperture size, the ridge depth reinforces, creating an effective ridge of some multiple of 0.2 μm. For example, five shots would result in a ridge height of 1.0 μm. These sharp ridges in the treatment zone can lead to unwanted epithelial regrowth, especially when correcting high diopter defects. A system that minimizes such ridges would promote smoother epithelial healing, preventing excessive regrowth and allowing the corrected eye to retain its correction for a longer period of time and with more stability.

Before ablating, most current excimer techniques also require physically scraping away the epithelial layer from the eye. This can be a traumatic procedure for the patient, and requires a high degree of precision by the surgeon. Alternative, less invasive methods of removal of the epithelium before ablation of the cornea are thus desirable.

Another problem with current techniques involves "central islands" created during the ablation process. A central island is an area of an ablation profile which is not ablated to a depth proportional to the number of excimer laser shots fired on that particular area. For example, in typical myopia patterns, the greatest depth of ablation is at the center of the pattern. In ablating such patterns, a recurring problem is that the central area is not ablated to as great a depth as is needed to create the proper ablation profile. The causes of this problem are not clear. However, techniques which reduce or eliminate this problem are highly desirable.

Further, present systems typically use either a relatively small spot size of less than 0.50 mm, or variable spot sizes that require the spot size to be adjusted throughout the treatment. A relatively small spot size has serious disadvantages, because it greatly increases the number of shots required to complete a treatment. A variable spot size also has disadvantages, in that it requires complex masking instrumentation to allow the spot size to be adjusted. Reducing or eliminating either of these problems would be greatly desirable.

Another problem that has become apparent is thermal heating. Although an excimer laser is a "cold" laser, which functions by breaking molecular bonds rather than by burning, repeated shots at a particular location will cause the tissue to heat. This limits the maximum shot rate allowed at a particular location. This in turn has historically caused treatments to take at least a certain amount of time, because the maximum shot rate could not be exceeded. Eliminating this limitation would similarly be desirable.

SUMMARY OF THE INVENTION

The method and apparatus according to the invention provides corneal correction using laser "polishing" or "dithering" in which subsequent shots used to ablate the eye are randomly or otherwise moved from a center axis of treatment to prevent the formation of large ridges in the treatment zone.

Further according to the invention, instead of using various aperture shapes, a relatively large beam is moved along the line of hyperopic or astigmatic correction desired, creating a line of overlapping shots. If further correction is necessary, overlapping lines are then created using various beam sizes, thus forming the desired correction curve in the cornea.

Further according to the invention, using this scanning beam technique, various non-symmetrical optical defects are corrected, such as a "curved" astigmatism, by modifying the line of travel of the overlapping shots or by otherwise generating a sequence of shots to appropriately ablate a non-symmetrical defect.

Further in the system and method according to the invention, the epithelium is removed using laser ablation. The epithelium is first dyed with an infrared fluorescent dye. The epithelium is then continually ablated using a beam covering the area of epithelium to be removed until an infrared scanning device recognizes that some portion of the epithelium is gone, as indicated by a lack of fluorescence. Then, either manually or under computer control, the spot size is reduced and areas that still fluoresce are ablated until they no longer fluoresce. This is repeated until the epithelium has been removed from the entire treatment area. This technique can also map the initial thickness of the epithelium before removal.

Further in the system and method according to the invention, myopia is treated by creating a lens formed by two astigmatism correcting ablation patterns at an angle to one another. Preferably, this pattern is developed by creating two astigmatism ablation patterns at right angles to each other. Further, according to the invention, each of these astigmatism ablation patterns is preferably created with a series of overlapping lines of shots.

The system and method according to the invention further provides a technique for using relatively large overlapping shots of a fixed size to accomplish a desired treatment pattern. According to the invention, a series of rings are calculated, in which each ring has a series of shots fired along the radius of the ring. Using an empirical algorithm, the number of shots, the distance of each ring from the center of the desired treatment area, and the optimal fixed shot size is determined. According to another embodiment, a shot dithering pattern is used to distribute the large, overlapping shots throughout the treatment area. These techniques have a number of advantages, including allowing large overlapping shots, thus reducing treatment time, and reducing the formation of large ridges that would be encountered in a treatment pattern in which the shots were centered on the treatment area. This ridging effect is even further reduced by placing these shots in a spiral pattern.

Further according to the invention, thermal heating is reduced. This is achieved by optimally adjusting the order in which the needed shots are fired. Typically, a single tissue location can only absorb a certain number of shots per second. According to the invention, however, subsequent shots in the treatment pattern are fired at different locations that are not overlapping. Then, the desired partially overlapping shot is later fired overlapping the first location. For example, a first shot is fired on one side of the treatment area, a second, nonoverlapping shot is fired on the other side of the treatment area, and then a third shot is fired partially overlapping the first shot. In another embodiment, the shot treatment array is sorted to maximize the distance between sequential shots. Alternatively, the array is randomly reordered, thus statistically reducing the number of overlapping sequential shots. It will be appreciated that the effective shot rate can be doubled, because a particular point of tissue is only being ablated on every other shot. By displacing the shots from each other, even higher shot rates can be realized.

Calculating the shot patterns needed using a fixed large spot size is nontrivial, generally not easily derived. Therefore, further according to the method and apparatus of the invention, the shot patterns are determined through an empirical search algorithm, which searches for appropriate rings of shots to ablate the desired pattern.

Further, according to the invention, shots are preferably fixed at a size between 2.0 and 3.5 mm. This minimizes the number of required shots, while providing the resolution necessary to ablate virtually any desired pattern.

BRIEF DESCRIPTION OF THE DRAWINGS

A better understanding of the present invention can be obtained when the following detailed description of the preferred embodiment is considered in conjunction with the following drawings, in which:

FIGS. 4A and 4B are illustrations showing a shot pattern for astigmatic correction according to the invention;

FIG. 5 is an illustration of a treatment zone illustrating a shot treatment pattern for a curved astigmatism according to the invention;

FIG. 6A and 6B are illustrations showing a shot pattern for treatment of hyperopia according to the invention;

FIG. 17 is a perspective view of a lens ablation pattern according to the invention created by ablating two orthogonal astigmatism correcting ablation patterns;

FIG. 18A is a top view of the ablation pattern of FIG. 17;

FIGS. 18B and 18C are side views of a portion of the ablation pattern of FIG. 18A;

FIGS. 24A, 24B, and 24C are enumerations of each shot used to create the pattern of FIG. 21 sorted by X position order, the X position and Y position being given in microns;

DETAILED DESCRIPTION OF THE PREFERRED EMBODIMENT

Figure 1A:
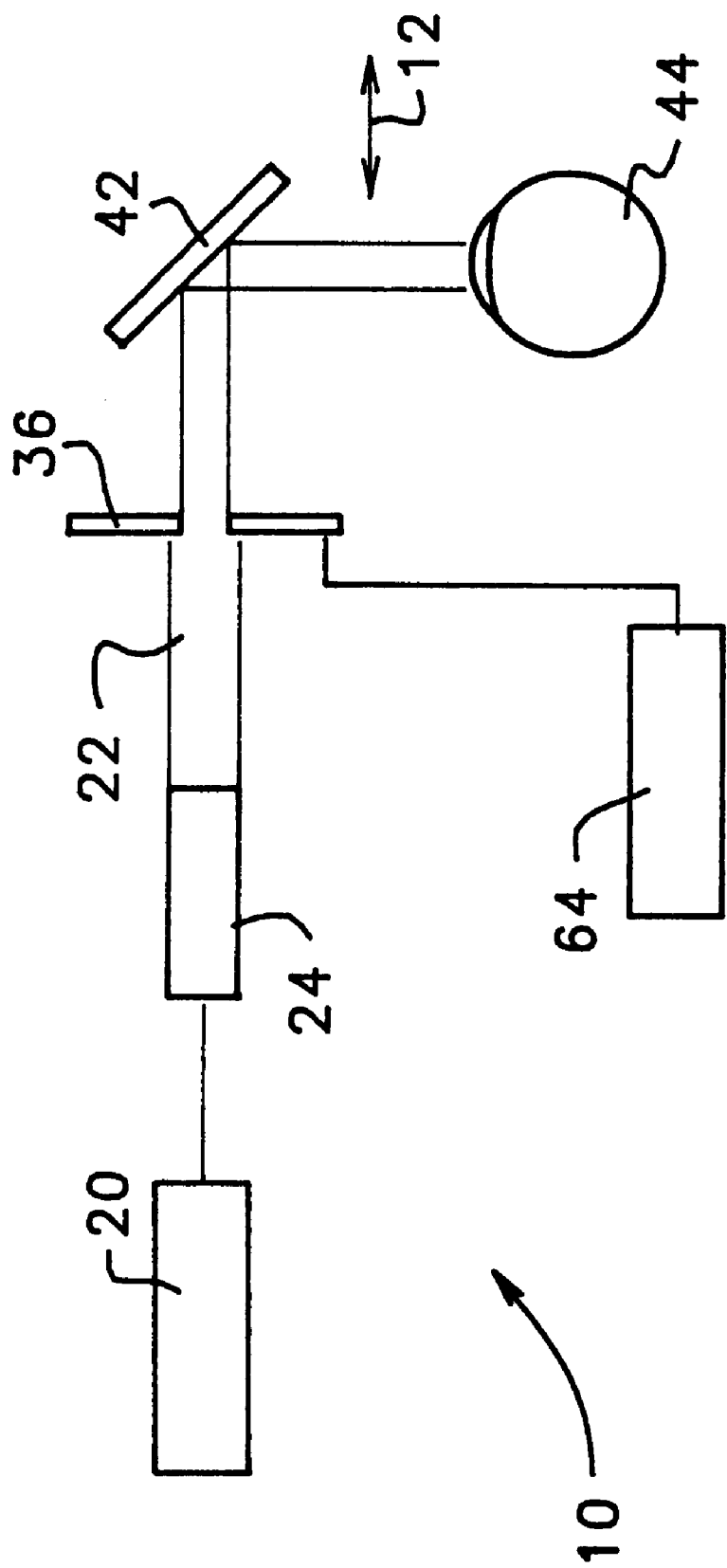
FIG. 1A is a simplified diagram illustrating a typical excimer laser eye surgery system in which can be implemented the apparatus and method according to the invention.

FIG. 1A, according to the invention, shows an excimer laser 20 providing a beam to a beam homogenizer 24 that also includes focusing components. The beam homogenizer 24 then provides a relatively homogeneous beam 22 to a field stop in the form of a diaphragm 36, which is regulated by a control unit 64 in such a manner that it limits the laser spot on an eye 44 to an area the maximum size of which is between approximately 10% and approximately 90% of the area of the region in which the tissue is to be removed when ablation is performed to correct for astigmatism or hyperopia. This preferred maximum size is more dependent on the shape and size of the area to be ablated rather than any fixed percentage, and could be, for example, between 20% and 80%. The larger the size of the spot that can be used the better, as that reduces treatment time.

Moreover, a beam manipulator unit in the form of a scanning mirror 42 is provided that also is regulated by the control unit 64. The scanning mirror 42 moves the axis of the beam 22 over at least a part of the region on the eye 44 in which the tissue is to be removed.

The invention thus provides an eye surgery system 10 for shaping the cornea by removing tissue with which removal of non-axially symmetrical profiles can be realized in a relatively shorter time. Further, the eye surgery system 10 compensates for any inhomogeneous distribution of energy over the beam spot.

By this means, not only can a very small spot be illuminated, as in the case of a scanning unit, but also a relatively large region can be illuminated so that the treatment can occur relatively quickly. To shorten treatment time, it is preferred to maintain the size of the laser spot on the eye 44 as large as possible for as long as possible, for example to at least 50% of the size of the region to be treated.

The scanning mirror 42 can, by way of illustration, tilt about or around at least one axis. Mirror elements that can be used, and in particular that can be tilted about two axes, are described in U.S. Pat. No. 4,175,832, for example.

Further, the control unit 64 can regulate the size of the laser spot on the eye 44 in correlation to the movement of the beam axis (through use of the scanning mirror 42) on the eye 44, thus precisely regulating the energy deposited on a specific area of the eye 44. Thus, non-axially symmetrical profiles can be generated on the corneal surface of the eye 44. Different types of diaphragms 36 can be used, for example ovals or circles with blocked centers.

Moreover, the scanning mirror 42 can be placed in the beam 22 not only after the diaphragm 36, but also before the diaphragm 36. It would then be preferable to move the diaphragm 36 synchronously with the scanning mirror 42.

In correcting spherical aberrations, the control unit 64 preferably moves the scanning mirror 42 such that the beam 22 oscillates from shot to shot in at least one direction, such as is illustrated by an arrow 12. Such oscillation compensates for inhomogeneity of the energy distribution over the beam 22. This oscillation finds application regardless of the maximum beam size.

To correct astigmatism, the scanning mirror 42 moves the axis of the beam 22 between at least two directions, neither of which are collinear with the axis of treatment of the eye 44. This permits treating an astigmatic eye, which, without being limited by theory, the latest research states has not one apex, but two. That is, it has the shape of camel humps. Also, the control unit 64 regulates the scanning mirror 42 such that the axis of the beam 22 oscillates at least one-dimensionally about each direction, thus compensating for homogeneity of the beam 22.

To correct for hyperopia, the axis of the beam 22 is preferably moved on a conic-shaped shell surface, it also being possible to superimpose an at least one-dimensional oscillation to compensate for inhomogeneity of the beam 22. By moving on a conic-shaped shell surface, a circular pattern of overlapping shots are projected onto the eye 44.

In adapting the diaphragm 36 to the typical shape of the cross-section of excimer laser beams, the diaphragm 36 may also have a non-axially symmetrical shape, with the diaphragm 36 being turned in order to homogenize the deposited energy during the movement of the axis of the beam 22 on the conic shell. The homogenization is enhanced if the turning of the diaphragm 36 occurs asynchronously to the rotation of the axis of the beam 22 on the conic shell.

Figure 1B:
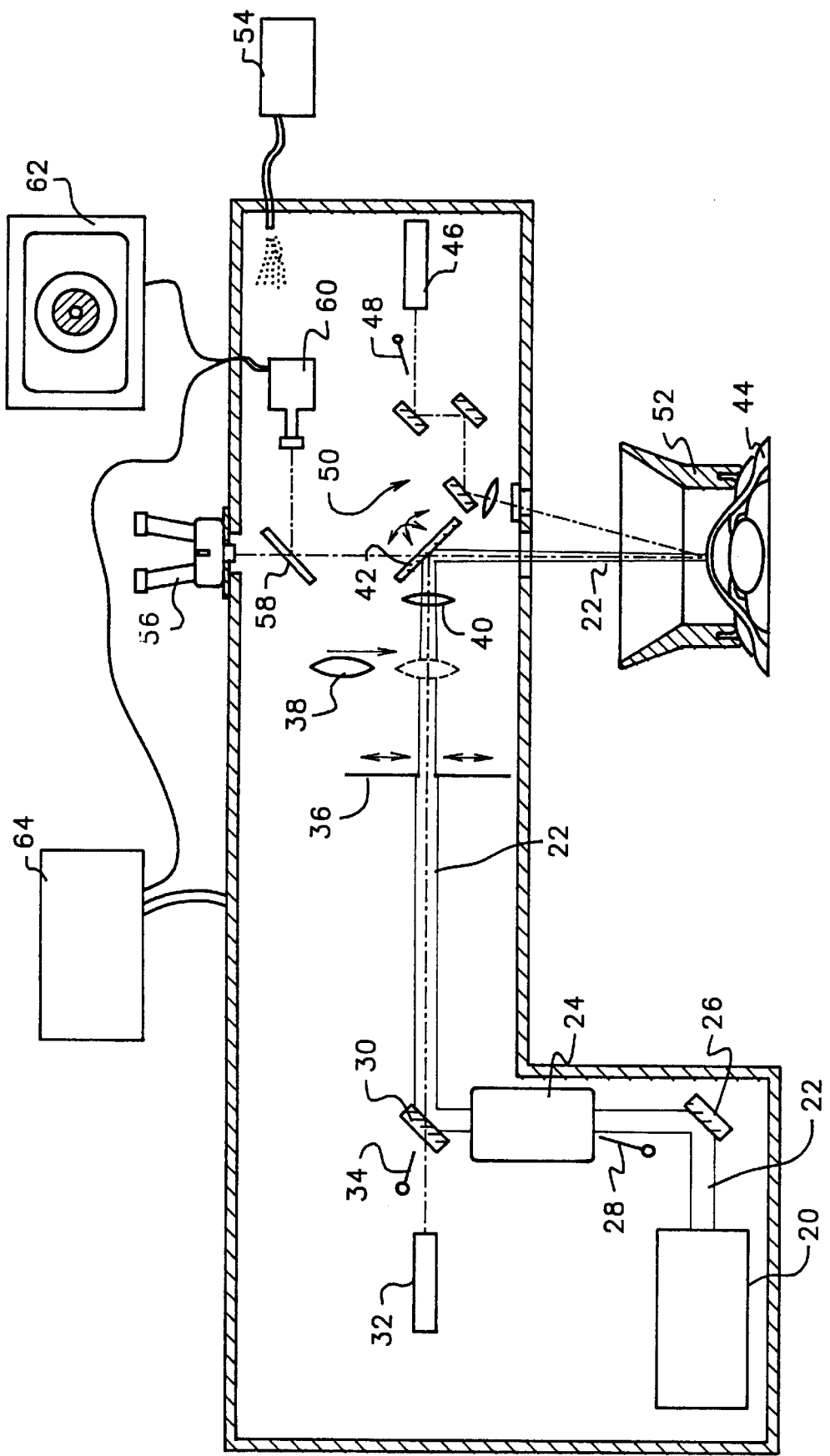
FIG. 1B is a more detailed diagram illustrating the system of FIG. 1A.

FIG. 1B shows additional details of the typical eye surgery system 10 in which the method and apparatus according to the invention would be implemented. An excimer laser 20 provides a pulsed beam 22 to a beam homogenizer 24 after reflection from optics 26. A shutter 28 is also provided to block transmission of the pulsed beam 22 to the beam homogenizer 24. The excimer laser 20 is a typical excimer laser as is well known in the art. It preferably provides a 193 nm wavelength beam with a maximum pulse energy of 400 mJ/pulse. The excimer laser 20 preferably provides maximum power at the treatment site of 1 W, with a pulse frequency of 10 Hz and a pulse length of 18 ns. Of course a variety of other excimer lasers could be used, and the apparatus and method according to the invention further have application where a laser other than an excimer laser is used. By way of example, the wavelength of the light from the laser is preferably less than 400 nm, as that provides the desired ablating action with reduced thermal heating. Further, other pulse energies can be provided, such as all the way down to 200 mJ/pulse, with typical repetition rates of 60 to 100 pulses per second with a typical pulse length of 10 to 30 ns. Again, all of these are merely typical values, and deviation from them can be made without changing the spirit of the apparatus and method according to the invention. Further examples of such laser systems can be found in U.S. Pat. No. 4,665,913, entitled "Method for Ophthalmological Surgery," issued May 19, 1987, and U.S. Pat. No. 4,729,372, entitled "Apparatus for Performing Ophthalmic Laser Surgery," issued Mar. 8, 1988.

The beam homogenizer 24 preferably includes standard homogenization and focusing hardware, which can be based both on optical mixing of the beam and on rotation of the beam. For an example of typical beam homogenization hardware, see U.S. Pat. No. 4,911,711 entitled, "Sculpture Apparatus For Correcting Curvature Of The Cornea," issued Mar. 27, 1990. Note that by providing the "dithering" according to the invention as discussed below, the beam homogenizer 24 can be simpler than the beam homogenization hardware shown in that reference. From the beam homogenizer 24, the pulsed beam 22 is then reflected off of optics 30, which also passes a red pilot laser beam from a pilot laser 32. This pilot laser 32 is preferably a 633 nm helium neon laser of less than 1 mW of power. The red pilot beam from the pilot laser 32 can also be blocked by a shutter 34. The pilot laser 32 is aligned so that its optical pathway coincides with the pulsed beam 22. The pilot laser 32 provides the functions of centering the beam 22 on the axis of treatment of the eye 44, and also provides for focusing on the eye 44, as is discussed below. Further, it can provide an optical fixation point for the patient, although a different laser or light source could also be provided for that purpose.

From the optics 30, the pulsed beam 20 (now also co-aligned with the beam from the pilot laser 32) then passes through an adjustable diaphragm 36, which allows the beam size to be adjusted before it enters the final optics. After the diaphragm 36, a spot mode lens 38, when in place, provides further concentration of the beam 22, allowing spot ablation of certain defects in the eye by a physician performing therapeutic rather than refractive surgery. The spot mode lens 38 is thus moved into and out of place depending on whether therapeutic or refractive treatment is desired.

Following the spot mode lens 38, a focusing lens 40 directs the beam 22 onto the scanning mirror 42, which then reflects the beam 22 onto a patient's eye 44. Note that the portion of the beam 22 from the pilot laser 32 is used for both adjusting the distance of the eye 44 from the entire eye surgery system 10 and for providing centering, as will be discussed below. The focusing lens 40 focuses light such that when the eye 44 is at the optimal distance, the beam 22 is properly focused onto the eye 44.

These various lenses and mirrors thus combine to form an optical system providing an excimer beam to the cornea. The optical system creates a laser spot on the cornea, and the spot size is adjustable, along with its location. It will be readily appreciated that a wide variety of different systems could be used to optically provide such a beam. For example, a lens could be used to adjust the spot size rather than an aperture, and instead of a scanning mirror, the patient or the patient's eye 44 could be physically moved to provide for shots at different locations on the eye 44.

Also provided in the system according to the invention is a focusing laser 46, whose beam can also be blocked by a shutter 48. The focusing laser 46 is preferably a green helium neon laser providing a beam of a wavelength of 535 nm and less than 1 mW of power. The beam from the focusing laser 46 travels through optics 50 and impinges on the eye 44 at an angle. The distance of the eye 44 from the eye surgery system 10 is adjusted such that both the beam from the pilot laser 32 and the beam from the focusing laser 46 impinge on the surface of the eye 44 at the same point.

Further provided is an optional fixation mask 52, which is well known in the art and is used to stabilize the eye 44 during surgery. It can include debris removal components, and is typically attached to the eye 44 through either a vacuum suction ring or through hooks. A clean gas purge unit 54 ensures that the optics and the beams in the system are free from any floating debris.

A microscope 56 is provided for the physician to observe progress during ablation of the surface of the eye 44. The microscope 56 is preferably a ZEISS OPMI "PLUS" part No. 3033119910, with magnifications of 3.4, 5.6 and 9.0 times. Field illumination is provided by a cold light source not shown, which is preferably the Schott KL1500 Electronic, ZEISS part number 417075. This microscope 56 focuses through the scanning mirror 42 and also focuses through a splitting mirror 58. The splitting mirror further provides a view of the eye 44 to an infrared video unit 60, which is used for the epithelial ablation discussed below. The infrared video unit 60 preferably provides an image output to a capturing video screen 62 and to a control unit 64. The infrared video unit 60 is preferably sensitive to both infrared light and visible light.

The control unit 64, which is typically a high performance computer compatible with an IBM PC by International Business Machines Corp., further preferably controls all components of the eye surgery system 10, including the shutters 28, 34, and 48, the diaphragm 36, the spot mode lens 38, and the scanning mirror 42.

Figures 1C, 1D:
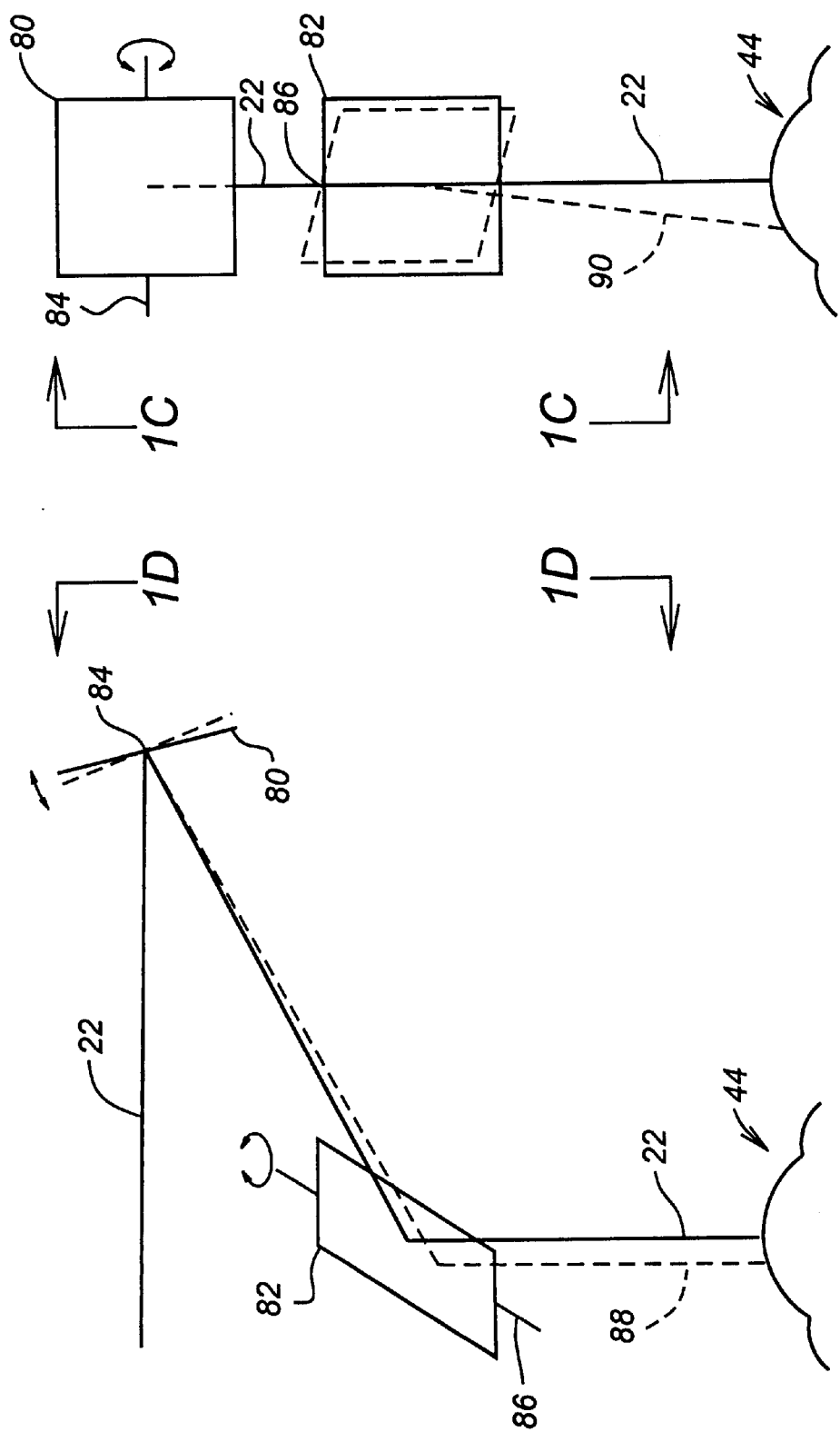
FIGS. 1C and 1D are a side view and an end view, respectively, of an alternative mirror arrangement to that shown in FIGS. 1A and 1B.

FIGS. 1C and 1D illustrate an alternative mirror arrangement to that of the mirror 42 of FIGS. 1A and 1B. Instead of using the single mirror 42, two mirrors 80 and 82 are used in the path of the beam 22 to ablate the eye 44.

The first mirror 80 is mounted on an axis 84 that provides for adjustment of the beam in one direction, while the second mirror 82 is mounted on an axis 86 that allows adjustment of the beam in a second direction. When the first mirror 80 is adjusted, for example, the beam 22 adopts an alternative beam path 88, which strikes the second mirror 82 at a different position, subsequently adjusting the position of the beam 88 onto the eye 44. This is seen in FIG. 1C. The other axis of adjustment is provided by the second mirror 82. Referring to FIG. 1D it is seen that when the second mirror 82 is adjusted, the beam 22 takes an alternate beam path 90, thus allowing the beam to be moved in the second axis.

These two mirrors thus combine to allow the beam to be aimed anywhere on the eye 44. This combination of mirrors allows for mounting with a single axis of rotation, rather than the double axis of adjustment required by the mirror 42. This can simplify implementation of the optics of the excimer laser system 10. The mirrors are adjusted using servo motors coupled to the axis 84 and 86, with those servo motors not being shown.

Figure 2A:
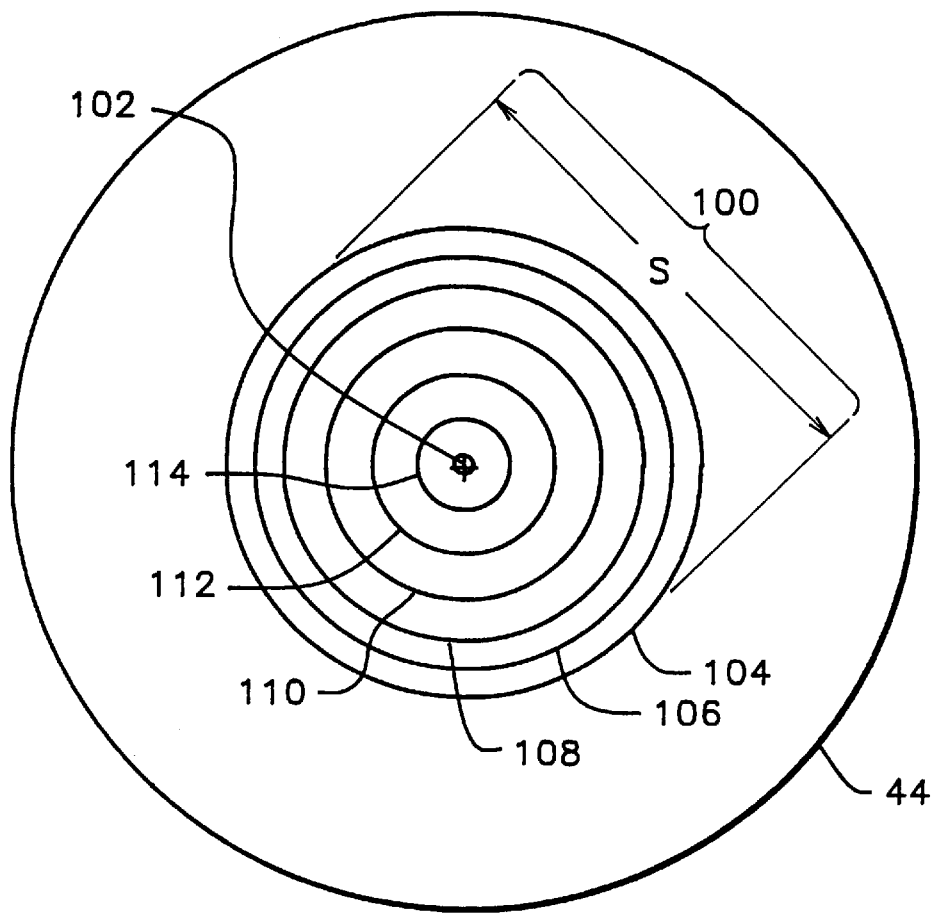
FIG. 2A is a view along the center axis of the treatment zone illustrating a typical large beam ablation pattern to correct for myopia.

FIG. 2A shows a simplified top view of the cornea of a typical eye 44 on which myopic correction has been performed. A treatment zone 100 of a width S is centered on an axis of treatment 102, which does not necessarily correspond to the optical axis of the eye 44. The treatment zone 100 is bounded by a first outer ablation ring 104, with subsequent ablation rings 106 to 114 shown spaced more widely towards the center of the axis of treatment 102 (note that preferably the smaller shots are performed first).

This wider spacing is topographical in effect, as in a typical system, the change in spot radius between shots may actually be constant, but with a greater number of shots performed toward the periphery of the treatment zone 100. Although only six ablation zones are shown, in a typical ablation pattern a greater number of spot sizes are used, and a greater number of shots are also performed. The ablation function for calculating the necessary depth of ablation for myopia is discussed below in conjunction with FIG. 7A.

Figure 2B:
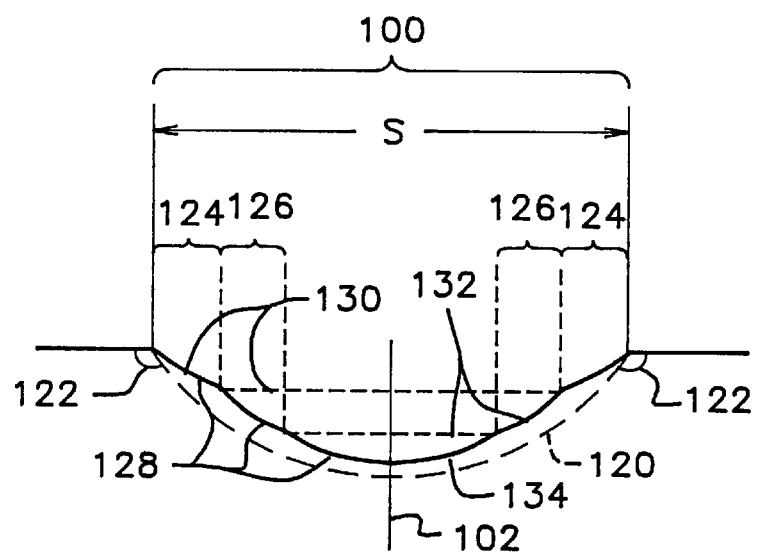
FIG. 2B is a side profile of FIG. 2A, further illustrating the use of transition zones.

In performing high dioptric correction for myopia, using the standard ablation function discussed below may result in an excessive depth of ablation along the axis of treatment 102. As illustrated in FIG. 2B, the standard equation for myopic ablation would result, for example, in a curve 120 which would lead to a high depth of ablation along the axis of treatment 102, and would also result in sharp edges 122 at the corner of the treatment zone 100. For simplicity, FIG. 2B shows the effect of treatment on a flat surface rather than the surface of the cornea. For such a high degree of correction, the use of transition zones can significantly reduce the edge effects in healing and can also reduce the center depth of ablation along the axis of treatment 102. These transition zones 124 and 126 effectively create a multi-focal lens. In FIG. 2B, two transition zones 124 and 126 are shown resulting in a shallower ablation curve 128. The first of these transition zones 124 is created by performing a myopic ablation over the full width S of the treatment zone 100 using a lesser degree of correction than the ultimate correction desired. Only those shots of a radius falling into the radius of the transition zone 124 are performed, however, thus leaving a uniformly ablated surface inside transition zone 124 for further treatment. This results in an initial curve 130.

Then, another series of myopic ablation shots using the myopic ablation function discussed below is performed using a somewhat greater degree of correction but using a smaller "treatment zone" (in actual practice, the smaller shots are preferably performed first). This resulting curve and uniformly ablated area 132 creates the second transition zone 126. Finally, a series of shots are performed for the full desired correction but using an again narrower zone of treatment, resulting in the final curve 134. The use of transition zones is known to the art of photorefractive keratectomy, and is described, for example, in Chapter 6 of the Color Atlas/Text of Excimer Laser Surgery, © 1993 Igaku-Shoin Medical Publishers, Inc. These transition zones 124 and 126 reduce any sharp edges 122 from being created, which could otherwise result in undesirable patterns of epithelia regrowth, and also reduce ultimate depth of ablation along the axis of treatment 102.

The following are two typical tables showing transition zones. For treatment to correct −9.00 diopters of myopia over a 5 mm treatment zone 100, the following transition zones could be used:

| No. | Min. [mm] Max. [mm] | Correction [diopters] |
|---|---|---|
| 1 | 0.50–4.00 | −9.00 |
| 2 | 4.00–4.20 | −7.50 |
| 3 | 4.20–4.40 | −6.00 |
| 4 | 4.40–4.60 | −4.50 |
| 5 | 4.60–4.80 | −3.00 |
| 6 | 4.80–5.00 | −1.50 |

Using this table, first a standard myopic correction using the equation discussed below would be performed for the desired −9.00 diopters of correction, but instead over a treatment zone 4.00 mm wide. This provides full correction in the middle 4.00 mm zone. Then, a transition is created by ablating from 4.00 to 4.20 mm using the lesser correction of −7.50 diopters. This is repeated for the subsequent entries in the table, thus forming transition zones of a greater radius of curvature.

Without the transition zones, 88 μm would be ablated at the axis of treatment 102; with the transition zones, only 71 μm is ablated—20% less. This is good for the stability of the cornea.

An example of treatment for −12.00 diopters over a full 7 mm treatment zone 100 is illustrated below:

| No. | Min. [mm] Max. [mm] | Correction [diopters] |
|---|---|---|
| 1 | 0.50–2.00 | −12.00 |
| 2 | 2.00–2.20 | −11.54 |
| 3 | 2.20–2.40 | −11.08 |
| 4 | 2.40–2.60 | −10.62 |
| 5 | 2.60–2.80 | −10.15 |
| 6 | 2.80–3.00 | −9.69 |
| 7 | 3.00–3.20 | −9.23 |
| 8 | 3.20–3.40 | −8.77 |
| 9 | 3.40–3.60 | −8.31 |
| 10 | 3.60–3.80 | −7.85 |
| 11 | 3.80–4.00 | −7.38 |
| 12 | 4.00–4.20 | −6.92 |
| 13 | 4.20–4.40 | −6.46 |
| 14 | 4.40–4.60 | −6.00 |
| 15 | 4.60–4.80 | −5.54 |
| 16 | 4.80–5.00 | −5.08 |
| 17 | 5.00–5.20 | −4.62 |
| 18 | 5.20–5.40 | −4.15 |
| 19 | 5.40–5.60 | −3.69 |
| 20 | 5.60–5.80 | −3.23 |
| 21 | 5.80–6.00 | −2.77 |
| 22 | 6.00–6.20 | −2.31 |
| 23 | 6.20–6.40 | −1.85 |
| 24 | 6.40–6.60 | −1.38 |
| 25 | 6.60–6.80 | −0.92 |
| 26 | 6.80–7.00 | −0.46 |

Figure 3A:
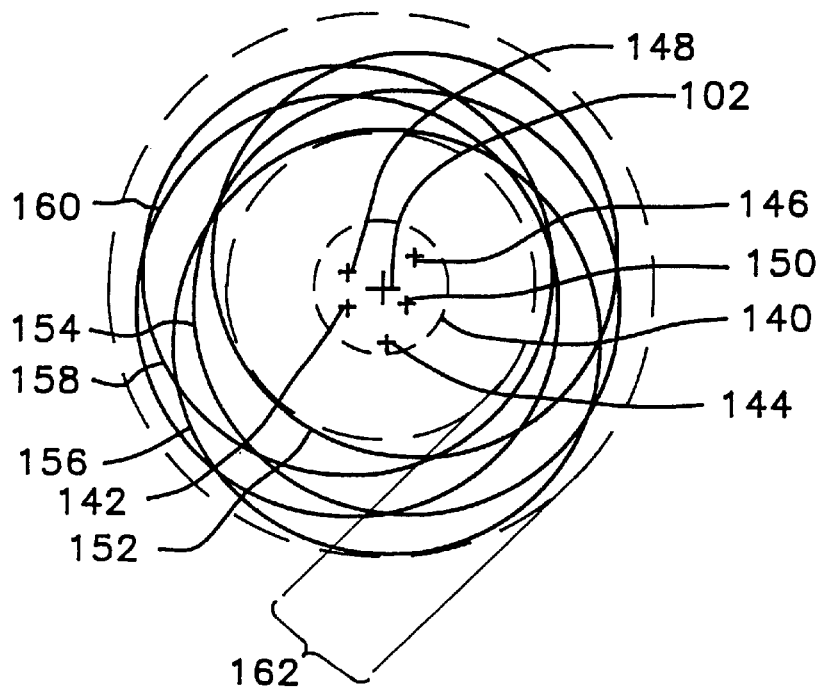
FIG. 3A is a view along the center axis of the treatment zone illustrating random dithering according to the invention.
Figure 3B:
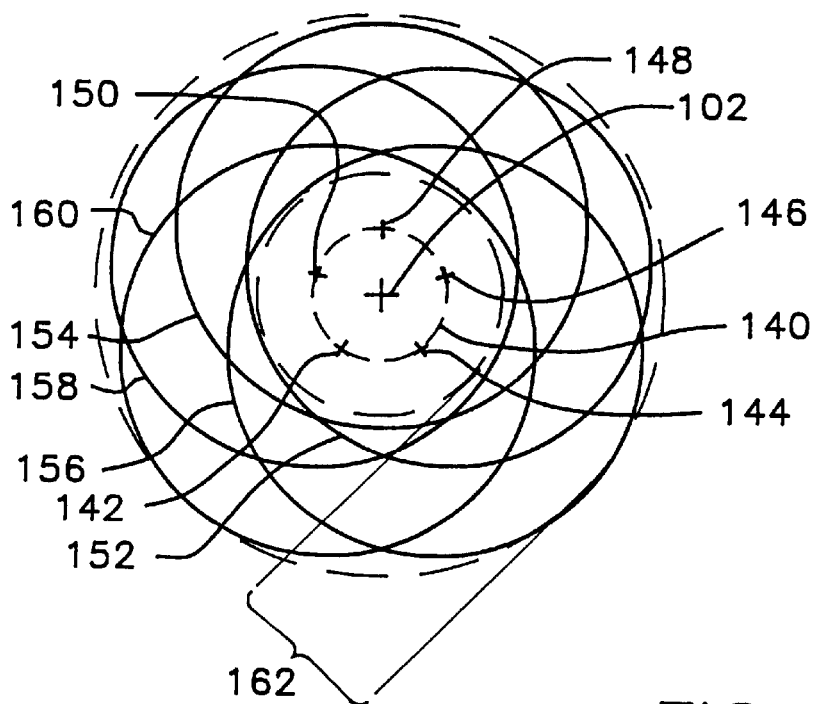
FIG. 3B is a view along the center axis of the treatment zone illustrating circular dithering according to the invention.

FIGS. 3A and 3B show an ablation pattern corresponding to one of the ablation rings 104 to 114 of FIG. 2A, but using the laser "dithering," or "polishing," according to the invention. The term "dithering" is used in the sense that small random or pseudo random fluctuations are added to the beam 22 to "smooth" particular errors that would otherwise build up. Assuming one of the ablation rings 104 to 114 of FIG. 2A includes five shots at a particular spot size, FIGS. 3A and 3B show the effect achieved according to the method and apparatus of the invention. In FIG. 3A, the axis of treatment 102 is shown, upon which shots in past systems have been centered, as shown in FIG. 2A.

According to the invention, however, the centers of the five shots are randomly distributed in a dithering zone 140 with the center axis of each shot being away from the axis of treatment 102. Five shots using randomly distributed centers 142 through 150 result in five individual excimer laser ablation shots 152 through 160. The radius of the dithering zone 140 is preferably somewhat less than the radius of the shots themselves. As can be seen, any reinforcement—i.e., ridge height greater than a single shot ridge height—occurs only incidentally, and generally the ridges are distributed over a dithering band 162. This provides a "smoothing" effect, reducing average ridge height.

FIG. 3B shows an alternative manner of performing this polishing, in which the shot centers 142 through 150 are evenly distributed around the periphery of the dithering zone 140. This case insures that none of the ablation shots 152 through 160, even though of the same radius, form reinforcing ridges.

In this manner, a smoother surface of the eye 44 is achieved during ablation to correct for myopia. This polishing, or dithering, could also be described as an "oscillation" of the laser spot upon the cornea. This dithering could also be one dimensional rather than two, and could also be created by vibrating the patient's eye 44, such as by vibrating the mask 52 or the patient himself. For example, a small mechanical vibrator could be placed in a patient table or in the mask 52. This could then provide the oscillation necessary. As can be readily appreciated, such a dithering technique can be applied to other forms of correction, such as using ring apertures and slit apertures to correct for hyperopia and astigmatism, as are known in the art. Further, the dithering could be applied to any other shot patterns such as for hyperopia and astigmatism, thus reducing the effects of both ridge height and beam 22 inhomogeneity.

FIGS. 4A and 4B illustrate a large beam scanning pattern used to correct for astigmatism according to the system and method of the invention. In the prior art, variable size slits were generally used to perform this correction, requiring further hardware and generally inflexible patterns of correction.

The method and apparatus according to the invention, however, correct astigmatism within the treatment zone 100, here with width S and length L, through a series of lines 170 and 172 created by a series of overlapping shots in the area to corrected for astigmatism. In the diagram, only the first line 170 and the second line 172 are shown, with the first line created using smaller spot sizes than the second line 172. According to the method of the invention, a lesser or greater number of lines are used to provide the desired degree of correction for astigmatism. This results in the ablation profile as shown in FIG. 4B. This profile generally corresponds to the curvature needed for a myopia ablation, whose formula is discussed below in conjunction with FIG. 7A.

A typical pattern used for ablating to correct for astigmatism for a −2.00 diopter correction would involve shots of:

| No. | Spot Size | Shots |
|-----|-----------|-------|
| 1 | 1.067 | 11 |
| 2 | 1.679 | 8 |
| 3 | 2.141 | 7 |
| 4 | 2.484 | 7 |
| 5 | 2.726 | 6 |
| 6 | 2.885 | 6 |
| 7 | 2.977 | 6 |
| 8 | 3.019 | 6 |
| 9 | 3.022 | 6 |
| 10 | 3.000 | 6 |

At each spot size, a line is created corresponding to the lines 102 and 104, and preferably the spots overlap by approximately 88%. This would create an appropriate modified curvature corresponding to a −2.00 diopter correction for astigmatism. These would be spread over a 3 mm width S of the treatment zone 100.

FIG. 5 is an illustration of shot patterns used to correct for non-symmetrical astigmatism. In this case, only a single treatment line 174 is shown; typically, a greater number of lines would be used, but for clarity, the single line 174 illustrates the treatment of a curved astigmatism that does not extend linearly across an axis of treatment 102 of the eye 44. In this way, a greater variety of types of astigmatism are correctable.

FIG. 6A illustrates the large beam scanning according to the invention used to correct for hyperopia without using ring apertures. Instead, only the single diaphragm 36 is used to adjust the spot size, and a circular ablation ring 180 over the treatment zone 100, as is well known to those skilled in performing hyperopic ablation, is created using multiple rings of different spot sizes and various overlaps. The approximate ablation profile is shown in FIG. 6B. The formula for the curvature for hyperopic ablation is discussed below in conjunction with FIG. 7B.

It will be noted that the shots for hyperopic ablation extend beyond the zone of treatment 100 of width S. The shots outside of this area do not provide for optical correction, but instead provide a smooth transition at the edge of hyperopic ablation. Further, although the circular ablation ring 180 is not shown extending all the way to the center of the axis of treatment 102, the final series of shots at the largest shot size preferably extend very close to that axis, to provide a smooth profile from the center of the axis of treatment 102 to the edge of the treatment zone 100.

A typical shot pattern for hyperopic correction of 5.00 diopters would involve shots of:

| No. | Spot Size | Shots | Overlap |
|-----|-----------|-------|---------|
| 1 | 2.000 | 1052 | 99.25 [%] |
| 2 | 2.469 | 128 | 95 |
| 3 | 3.060 | 104 | 95 |
| 4 | 3.966 | 80 | 95 |
| 5 | 4.600 | 27 | 87 |

In this pattern, each series of shots is used to create a ring with centers at a radius of 2.5 mm from the axis of treatment 102 of the eye 44. In this case, the preferred overlap is variable per treatment ring, and is illustrated in the table.

As can further be appreciated, although the illustrated shot patterns use circular apertures, another aperture shape could be used to create the hyperopic correction pattern and the astigmatism correction pattern according to the invention. For example, an oval shot shape could be used, and that oval could be rotated during the hyperopic correction, such that one axis of the oval pointed to the axis of treatment 102 of the eye 44. Alternatively, the oval could be rotated asynchronously with the rotation about the axis of treatment 102, thus further reducing the effects of inhomogeneity of the beam 22.

Figure 7A:
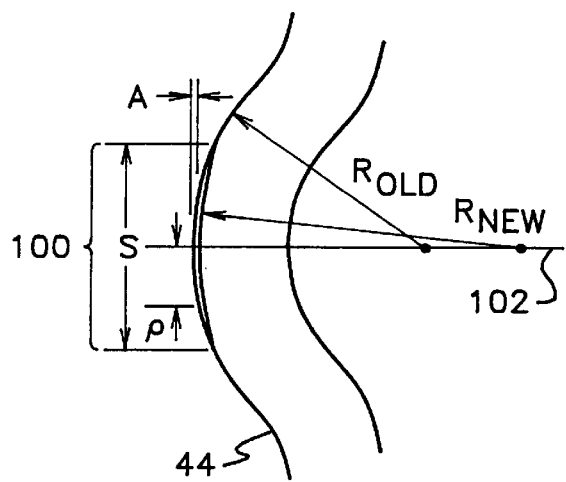
FIGS. 7A and 7B are side profiles of the cornea illustrating initial and ending radii of curvature over a treatment zone for correction of myopia and hyperopia.
Figure 7B:
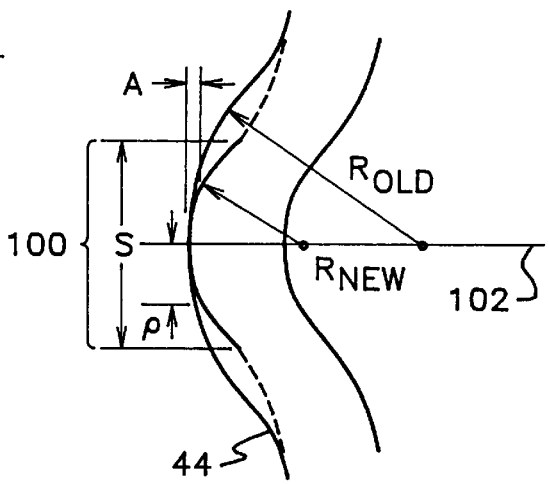

FIGS. 7A and 7B illustrate various mathematical attributes of the ablation profiles of the preceding ablation patterns. FIG. 7A shows a typical ablation profile for myopic ablation and FIG. 7B illustrates a typical ablation profile for hyperopic ablation. In both, the initial radius of the cornea of the eye 44 is given by $R_{OLD}$ and the new, desired radius of the cornea of the eye 44 is given by $R_{NEW}$. The absolute zone of treatment 100 is designated of a width S, which corresponds to the effective area that performs the corrective function. It is typically between 2 and 8 mm, but can be larger or smaller. The depth of ablation at any point within the treatment zone 100 of width S is given by a variable A, which stands for ablation depth. The distance from the axis of treatment 102 is given by a variable $\rho$.

To calculate the new radius $R_{NEW}$, the old radius $R_{OLD}$ and a desired dioptric correction $D_{CORR}$ is used in the following equation:

$$\text{NEW\_RADIUS}(R_{OLD}, D_{CORR}) = \frac{n-1}{\frac{n-1}{R_{OLD}} + D_{CORR}}$$

NEW_RADIUS returns a parameter indicating the new radius of correction needed, $R_{NEW}$, to given $R_{OLD}$ and $D_{CORR}$. Both $R_{OLD}$ and $R_{NEW}$ are measured in meters, and are typically between 5 and 15 mm.

The formula for calculating the necessary depth of ablation to correct for myopia as illustrated in FIG. 7A is given below:

$$\text{MYO\_ABLATE}(\rho, R_{OLD}, S, D_{CORR}) =$$

$$\sqrt{R_{OLD}^2 - \rho^2} - \sqrt{\left(\frac{R_{OLD}(n-1)}{n-1+R_{OLD}D_{CORR}}\right)^2 - \rho^2} -$$

$$\sqrt{R_{OLD}^2 - \frac{S^2}{4}} + \sqrt{\left(\frac{R_{OLD}(n-1)}{n-1+R_{OLD}D_{CORR}}\right)^2 - \frac{S^2}{4}}$$

The myopic ablation function MYO_ABLATE returns a needed depth of ablation at a particular distance ρ from the axis of treatment 102, given the uncorrected radius of curvature of the eye 44 $R_{OLD}$, a desired zone of correction S, and a desired degree of correction $D_{CORR}$. The function MYO_ABLATE also provides the appropriate degree of correction across the width S of a trench used to correct for astigmatism, as illustrated in FIGS. 4A and 4B.

Turning to FIG. 7B, the formula for hyperopic ablation is given below:

$$\text{HYP\_ABLATE}(\rho, R_{OLD}, D_{CORR}) = \sqrt{R_{OLD}^2 - \rho^2} -$$

$$\sqrt{\left(\frac{R_{OLD}(n-1)}{n-1+R_{OLD}D_{CORR}}\right)^2 - \rho^2} + \frac{R_{OLD}(n-1)}{n-1+R_{OLD}D_{CORR}} - R_{OLD}$$

The hyperopia ablate function HYP_ABLATE only uses three parameters, as it does not need optical zone of correction S.

These specific algorithms for creating appropriate curvatures are well known in the art and can be found in MUNNERLYN, C. AND KOONS, S., PHOTOREFRACTIVE KERATECTOMY: A TECHNIQUE FOR LASER REFRACTIVE SURGERY, Cataract Refract Surg., Vol. 14, (Jan. 1988).

Further, in the routines for performing ablation discussed below in conjunction with FIGS. 9–14, the inverse of these equations are needed. While the above equations return a depth of ablation needed at a particular value of ρ for a given degree of correction, the inverse equations do the exact opposite. They return the particular value of ρ at which a particular depth of ablation is needed given a particular degree of correction. These equations are given below:

$$\text{INV\_MYO\_ABLATE}(R_{OLD}, S, A, D_{CORR}) =$$

$$2(R_{OLD}^2 + R_{NEW}^2) - (C-A)^2 - \left(\frac{R_{OLD}^2 - R_{NEW}^2}{C-A}\right)^2$$

where $$C = \sqrt{R_{NEW}^2 - (S/2)^2} - \sqrt{R_{OLD}^2 - (S/2)^2}$$

and $$R_{NEW} = \text{NEW\_RADIUS}(R_{OLD}, D_{CORR})$$

$$\text{INV\_HYP\_ABLATE}(R_{OLD}, A, D_{CORR}) =$$

$$2(R_{OLD}^2 + R_{NEW}^2) - (C-A)^2 - \left(\frac{R_{OLD}^2 - R_{NEW}^2}{C-A}\right)^2$$

where $$C = R_{NEW} - R_{OLD}$$

and $$R_{NEW} = \text{NEW\_RADIUS}(R_{OLD}, D_{CORR})$$

The inverse myopic ablation function INV_MYO_ABLATE returns a parameter indicating the distance corresponding to ρ from the center of ablation in meters given a depth of ablation A, also in meters. It also uses the parameters $R_{OLD}$, S, and $D_{CORR}$.

The inverse hyperopic ablation function INV_HYP_ABLATE also returns a radius from the center of ablation in meters corresponding to ρ, given a depth of ablation A at a certain correction $D_{CORR}$ It returns ρ indicating how far away from the center of ablation a certain depth of ablation will be found.

Figure 8:
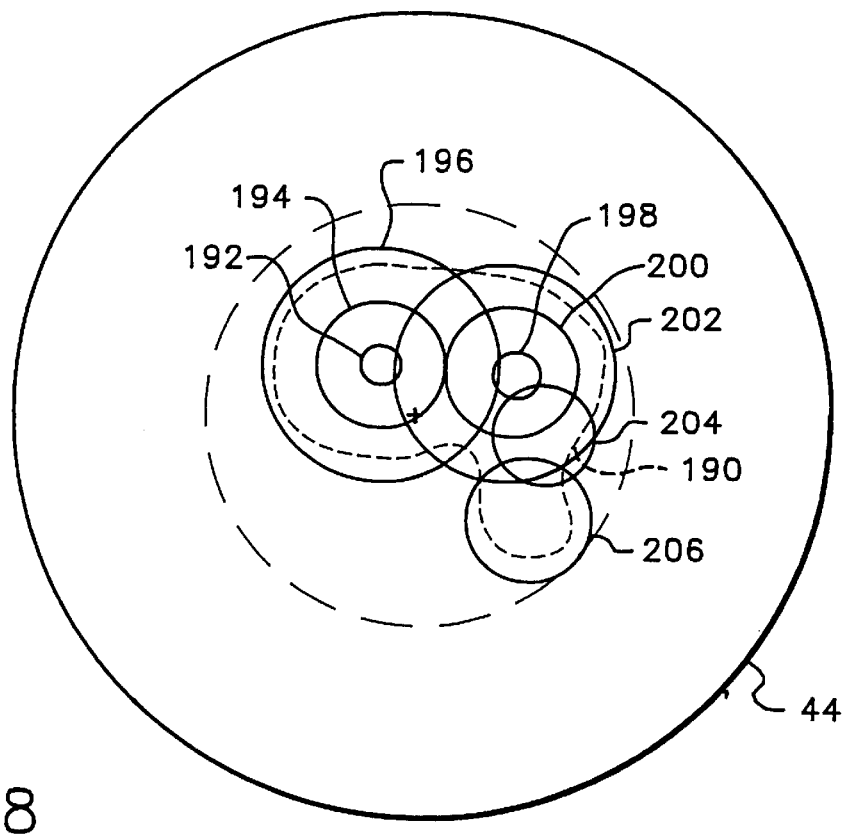
FIG. 8 is an illustration of shot patterns used to correct for general non-symmetrical aberrations of the eye according to the invention.

FIG. 8 illustrates how the system using aiming of the axis of ablation and variable spot sizes can correct for any topography of the eye 44 that is abnormal, including non-symmetric topographies. In FIG. 8, one line of a desired treatment topography 190 is illustrated. This could be retrieved, for example, from a computerized eye topography system which indicates various abnormalities in the surface of the eye 44. Using such a topography system, the eye surgery system 10, using the control unit 64, then performs a series of shots, which, for simplicity, are illustrated as eight shots 192 through 206. In actual practice, a far greater number of shots would likely be used. As the system knows the needed ablation at each point, it creates a map of the topography desired and performs ablation using various shot sizes aimed at various points to perform the necessary correction. In this way, a wide variety of non-symmetrical defects of the cornea can be corrected, such as apple and banana shapes, as well as any other abnormal shape.

Figure 9:
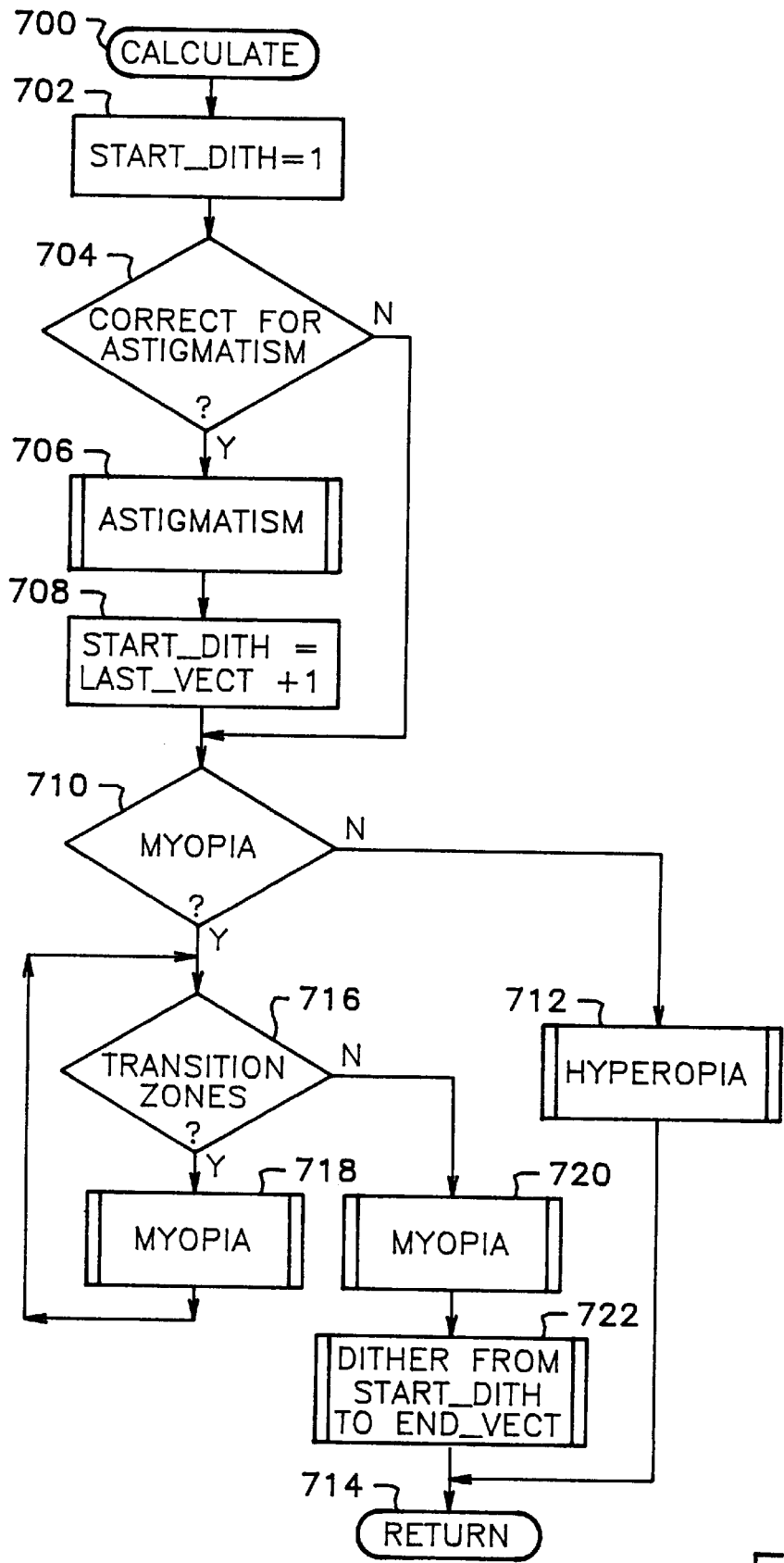
FIG. 9 is a flowchart illustrating a calculation routine used to perform correction for astigmatism, hyperopia, and myopia using the random or circular dithering and large beam scanning according to the invention.

FIG. 9 is a flowchart illustrating a CALCULATE routine 700 that would execute preferably on the control unit 64. The CALCULATE routine 700 calculates a series of shot patterns necessary to perform the desired ablation of the eye 44 to correct for a variety of conditions. In the described embodiment, shot patterns are created to correct for astigmatism, hyperopia, and myopia as described in conjunction with preceding FIGS. 2A to 7. Further, the dithering as illustrated in FIGS. 3 and 4 is applied to myopic correction shot patterns.

Preferably, the CALCULATE routine 700 runs in the control unit 64, which performs the necessary shot calculations before beginning an ablation sequence. By having all the points precalculated, there is no delay in calculation, so each successive shot can be fired in rapid sequence, as soon as the excimer laser 20 is ready. This provides for quicker treatment times and less difficulty in having the patient center on an optical fixation point.

Beginning at step 702, the CALCULATE routine 700 sets a variable START_DITHER to 1. This variable indicates the first ablation shot at which dithering is to begin, and is further discussed below. Note that all of the ablation shots are preferably stored in an array, and START_DITHER indicates a location within that array. Control proceeds from step 702 to step 704, where the routine 700 determines whether astigmatism correction is desired. This is pre-entered by the physician, including both angle of and degree of astigmatic correction, along with the maximum treatment area. As is readily apparent, the routine 700 could also request a degree of curvature for the line of astigmatic correction in the case of nonsymmetric astigmatism, and even provide for greater correction towards one or the other ends of the astigmatic region.

If astigmatic correction is desired, control proceeds from step 704 to step 706, where an ASTIGMATISM routine 750 is performed (discussed below in conjunction with FIGS. 10A and 10B), creating the appropriate shot patterns for the desired astigmatic correction. These shot patterns, for example, correspond to those discussed in conjunction with FIGS. 4A and 4B.

Once the shot pattern for astigmatic correction is calculated at step 706, control proceeds to step 708, where START_DITHER is set to a variable LAST_VECTOR. LAST_VECTOR points to the last calculated shot in the array for an ablation run. In this case, it points to the last vector calculated by the ASTIGMATISM routine 750. Because astigmatism involves overlapping shots rather than potentially reinforcing shots, dithering is preferably not performed during astigmatism correction in the disclosed embodiment, although it could be.

From step 704, if no correction for astigmatism was desired, and from step 708 in any case, control then proceeds to step 710, where the CALCULATE routine 700 determines whether correction for myopia is desired. If not, correction for hyperopia is desired, so control proceeds to step 712 where a HYPEROPIA routine 850 is performed, to be discussed below in conjunction with FIG. 12. As correction for hyperopia is similar to correction for astigmatism, but with the shots in a circle rather than a line, dithering is preferably not performed (although it could be) in the disclosed embodiment, so control then proceeds to step 714, where the routine 700 returns to a master routine, which then allows the physician to begin execution of the shot sequence calculated by the CALCULATE routine 700.

If at step 710 it was determined that correction for myopia is desired, the CALCULATE routine 700 then proceeds to step 716, where it determines whether transition zones are requested. If so, multiple myopic shot series must be formed with the initial "transition zone" series being created by performing a myopia correction. This was discussed above in conjunction with FIG. 2B. So, control proceeds to step 718 where a MYOPIA routine is performed to create a transition zone. This creates a standard myopia correction shot sequence for the transition zone.

Proceeding again to step 716, it is again determined whether more transition zones are required. If the last transition zone shot sequence has been calculated, or if none is needed, control then proceeds to step 720, where the MYOPIA routine is again executed, this time to provide the final correction for myopia.

The creation of series of shot sequences to correct for myopia is well known in the art. Given the necessary depth of ablation as determined by the MYO_ABLATE function described above, a shot pattern is created using appropriate shot sizes to conform to the necessary depth of ablation at each point radiating away from the axis of treatment 102.

Control then proceeds to step 722, where a DITHER routine 940 or 970 is executed as described below in conjunction with FIGS. 13 and 14, performing dithering, or randomizing, on all shots from START_DITHER as set in either step 702 or step 708 to LAST_VECTOR, which was described above in conjunction with step 708. At this point, calculation of the ablation shot sequence is complete, so control proceeds to step 714 where the CALCULATE routine 700 returns to the main program so that the physician can execute the ablation run as is now stored in the array.

Figure 10A:
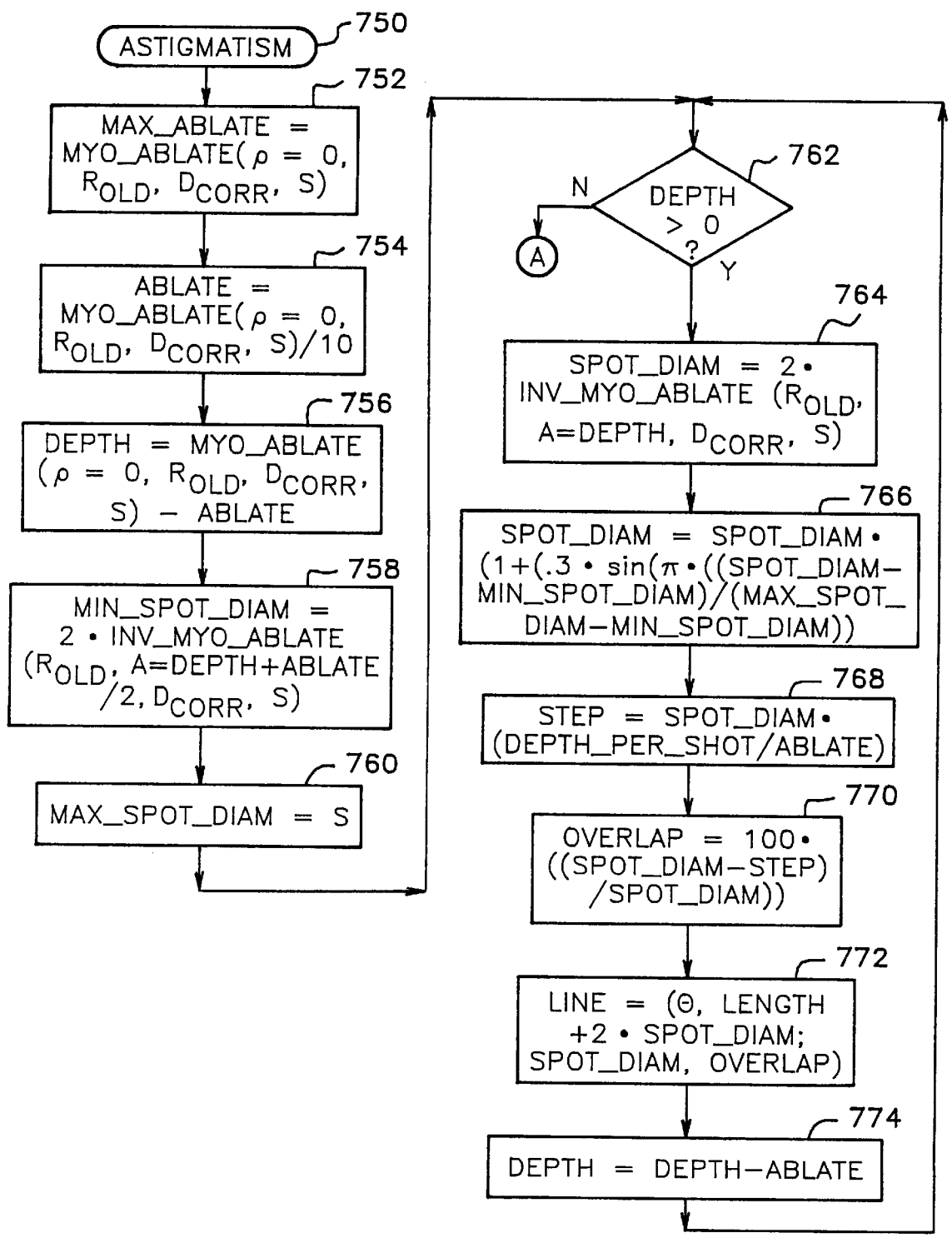
FIGS. 10A, 10B, and 11 are flowcharts illustrating an astigmatism routine used by the calculation routine of FIG. 9.
Figure 10B:
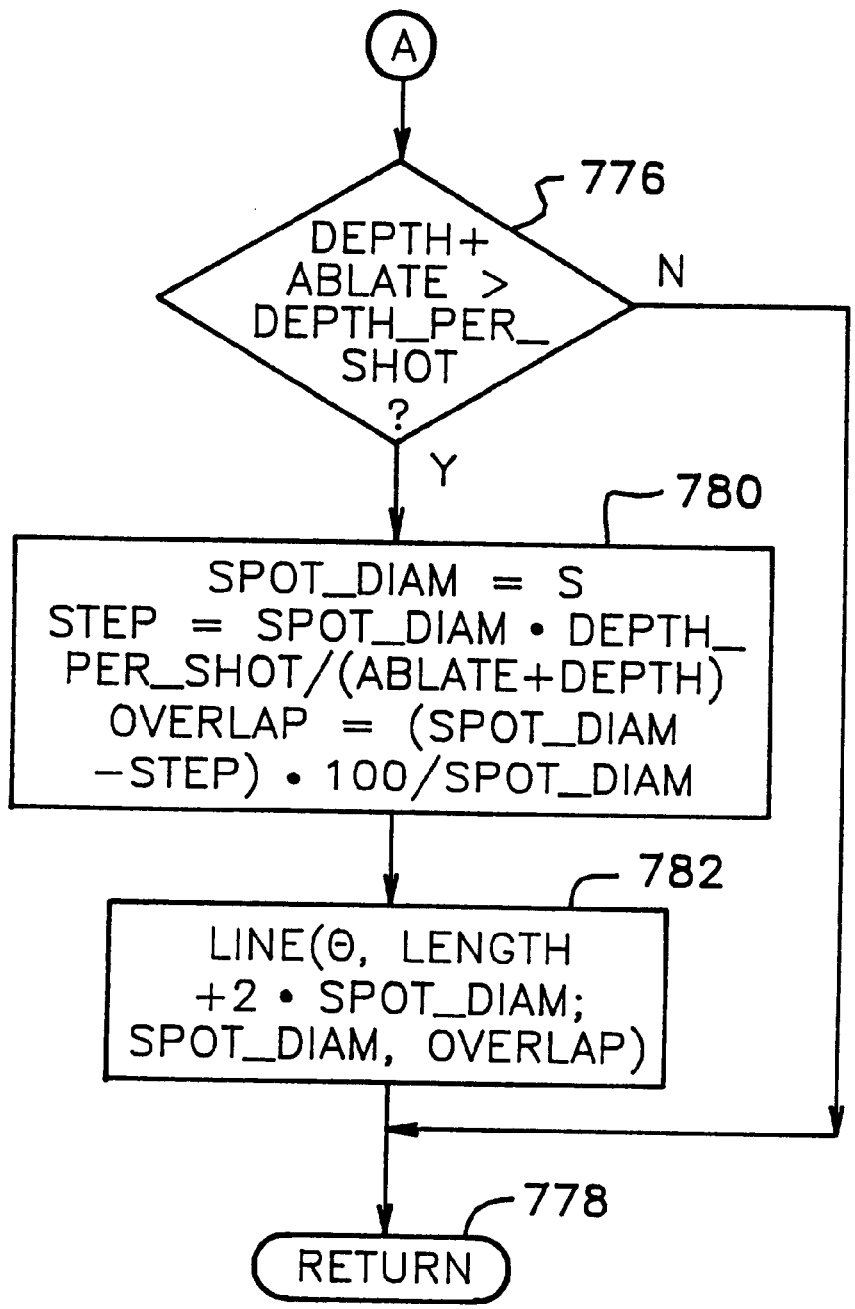

FIGS. 10A and 10B are a flowchart of the ASTIGMATISM routine 750 that is used to calculate the shot vectors necessary to create "trenches" of overlapping lines to correct for a desired dioptric degree of astigmatism along a particular axis. An appropriate number of trenches are created, with each trench preferably using progressively larger spot sizes. Beginning at step 752, the necessary depth of overall ablation is calculated at the deepest part of the series of trenches. This is done using the myopic ablation function MYO_ABLATE, described above in conjunction with FIG. 7A. A variable MAX_ABLATE is set to the value returned by MYO_ABLATE using $\rho=0$, indicating the necessary depth at the center of the trench (the deepest point). Also passed to MYO_ABLATE are the uncorrected radius of curvature $R_{OLD}$, the necessary dioptric correction $D_{CORR}$ and the width of the astigmatism treatment zone S. Note that S is equal to the width of the astigmatism treatment zone, not the length.

Control then proceeds to step 754, where the necessary depth of ablation per trench is calculated. This is preferably calculated as is MAX_ABLATE above, but instead setting a variable ABLATE, which indicates the amount of ablation per trench, to a value equal to MAX_ABLATE divided by 10. This indicates that preferably ten trenches are to be made, although less may be required as the amount of ablation per trench is calculated.

Control then proceeds to step 756, where a variable DEPTH is set equal to the previously calculated MAX_ABLATE minus ABLATE. DEPTH indicates the amount of ablation remaining to be performed to provide the desired degree of correction.

Control then proceeds to step 758, where a minimum spot diameter MIN_SPOT_DIAM is calculated, indicating the smallest spot diameter to be used to create a trench. MIN_SPOT_DIAM is set equal to two times the radius returned by the inverted myopic ablation function INV_MYO_ABLATE. INV_MYO_ABLATE is called with the initial radius of curvature $R_{OLD}$ with A set to DEPTH plus ABLATE/2, with $D_{CORR}$ as the degree of dioptric correction desired, and with S as the width of the treatment zone. The value returned by calling this function is the radius at which 95% of the overall ablation depth needed will be performed, and this radius will preferably be relatively close to the center of the axis of treatment—i.e., the radius will be small compared to the overall width of each trench.

Proceeding to step 760, a maximum spot diameter MAX_SPOT_DIAM is set equal to S, which is simply the width of the astigmatism treatment zone 100 (not the length).

Proceeding to step 762, a loop is entered that creates a series of trenches to provide for the overall degree of correction for astigmatism needed. First, at step 762 it is determined whether DEPTH is greater than zero. Again, DEPTH is the remaining depth necessary to ablate, which will be greater than zero when enough trenches have not been created to provide the desired degree of correction.

If DEPTH is greater than zero, control proceeds to step 764, where the spot diameter SPOT_DIAM is set equal to two times the result returned by INV_MYO_ABLATE, when that function is called with A set equal to DEPTH. This returns the radius at which the ultimate necessary ablation equals DEPTH. As DEPTH is initially nearly equal to the overall depth of ablation needed, the initial spot diameter will thus be small.

Proceeding to step 766, the spot diameter SPOT_DIAM is empirically corrected. This is done by setting SPOT_DIAM equal to (1+(0.3·SIN(π·(SPOT_DIAM−MIN_SPOT_DIAM)/(MAX_SPOT_DIAM−MIN_SPOT_DIAM)))). This performs an empirical adjustment to the spot diameter to provide better results and better conform the overall correction to the desired curve necessary to correct for astigmatism.

Proceeding to step 768, a variable STEP indicating the amount to move the spot target on each succeeding shot is set equal to SPOT_DIAM·(DEPTH_PER_SHOT/ABLATE). DEPTH_PER_SHOT is the amount of ablation per shot, and is typically 0.2 µm. Then, at step 770 a variable OVERLAP is set equal to 100·(SPOT_DIAM−STEP)/SPOT_DIAM. This is the amount of overlap in percent needed for each shot.

Proceeding to step 772, a routine LINE 800 is called, discussed below in conjunction with FIG. 11, with Θ set to the angle at which to create the line of astigmatism, a LENGTH variable set to a predetermined length of the astigmatism series of shots plus 2·SPOT_DIAM, SPOT_DIAM indicating the spot size, and OVERLAP.

The series of shots for the line having been created, control proceeds to 774, where DEPTH is reduced by ABLATE, which is the amount to ablate per trench. Control then loops to step 762, where the reduced value of DEPTH is again compared to zero. This loop is repeated, creating lines of shots with progressively larger spot diameters, until DEPTH is less than zero. DEPTH will be less than zero when virtually all of the ablation shots have been calculated necessary to perform the desired degree of correction.

Once DEPTH is less than zero, control proceeds to step 776, where it is determined whether DEPTH plus ABLATE is greater than DEPTH_PER_SHOT. If not, then another line of ablation should not be performed, as that would provide too much correction, so control then proceeds to step 778 where the ASTIGMATISM routine 750 returns to the CORRECTION routine 700.

If at step 776 the "residue" of ablation still needed does not exceed DEPTH_PER_SHOT, control instead proceeds to step 780. There, SPOT_DIAM is set to the maximum spot diameter of S, which is the width of the treatment zone 100 for the astigmatism line of trenches, STEP is set equal to SPOT_DIAM·DEPTH_PER_SHOT/(ABLATE+DEPTH) and OVERLAP is set equal to (SPOT_DIAM−STEP)·100/SPOT_DIAM.

Control then proceeds to step 782, where a final trench is created using the variables set at step 780 spot width by calling the routine LINE 800. The routine 750 then returns at step 778.

The ASTIGMATISM routine 750 thus creates a shot pattern as described above in conjunction with FIG. 4A.

Figure 11:
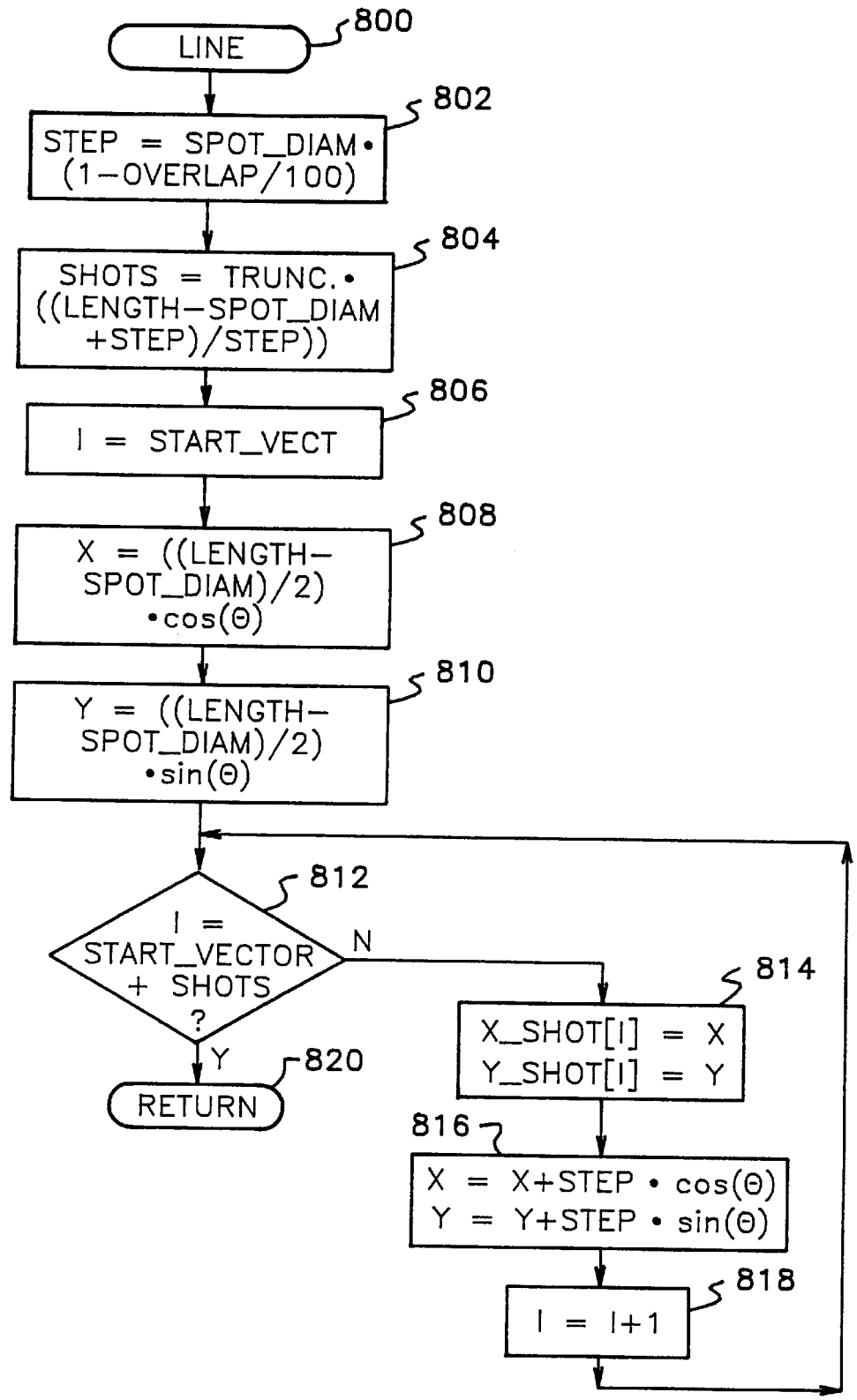

FIG. 11 is a flowchart of the LINE routine 800. This routine 800 calculates the shots for the generation of a line used in creating an astigmatism correction sequence of shots. The desired spot size is passed to the routine 800 in a variable SPOT_DIAM, an overlap percentage is passed in a variable OVERLAP, and the length of the line is determined by a LENGTH variable passed to the LINE routine 800.

Beginning at step 802, the LINE routine 800 first calculates the step size, which is equal to SPOT_DIAM·(1−OVERLAP). Proceeding to step 804, the number of shots required is calculated equal to the truncated value of (LENGTH−SPOT_DIAM+STEP)/STEP. Proceeding to step 806, a counter variable I is set equal to a variable START_VECTOR which is equal to LAST_VECTOR+1. LAST_VECTOR is set equal to I upon completion of the LINE routine 800.

Control then proceeds to step 808, where a variable corresponding to the X axis displacement from the axis of treatment 102 is set equal to ((LENGTH−SPOT_DIAM)/2)·cos θ, where θ is the angle of desired astigmatic correction. In step 810, Y is correspondingly set to ((LENGTH−SPOT_DIAM)/2)·sin θ.

Control then proceeds to step 812, where it is determined whether I equals START_VECTOR plus SHOTS, indicating the end of this line of shots. If not, control proceeds to step 814, where an array location X_SHOT[I] corresponding to the shot location of this particular shot is set equal to X and Y_SHOT[I] is correspondingly set equal to I. Then, at step 816 X is set equal to X+(STEP·cos θ) and Y is set equal to Y+(STEP·sin θ). This is the delta increment required for the next shot.

Control then proceeds to step 818, where I is incremented, and the routine then loops to step 812. Once I is equal to START_VECTOR+SHOTS, indicating the end of this line, the routine returns to the ASTIGMATISM routine 750 at step 814.

Figure 12:
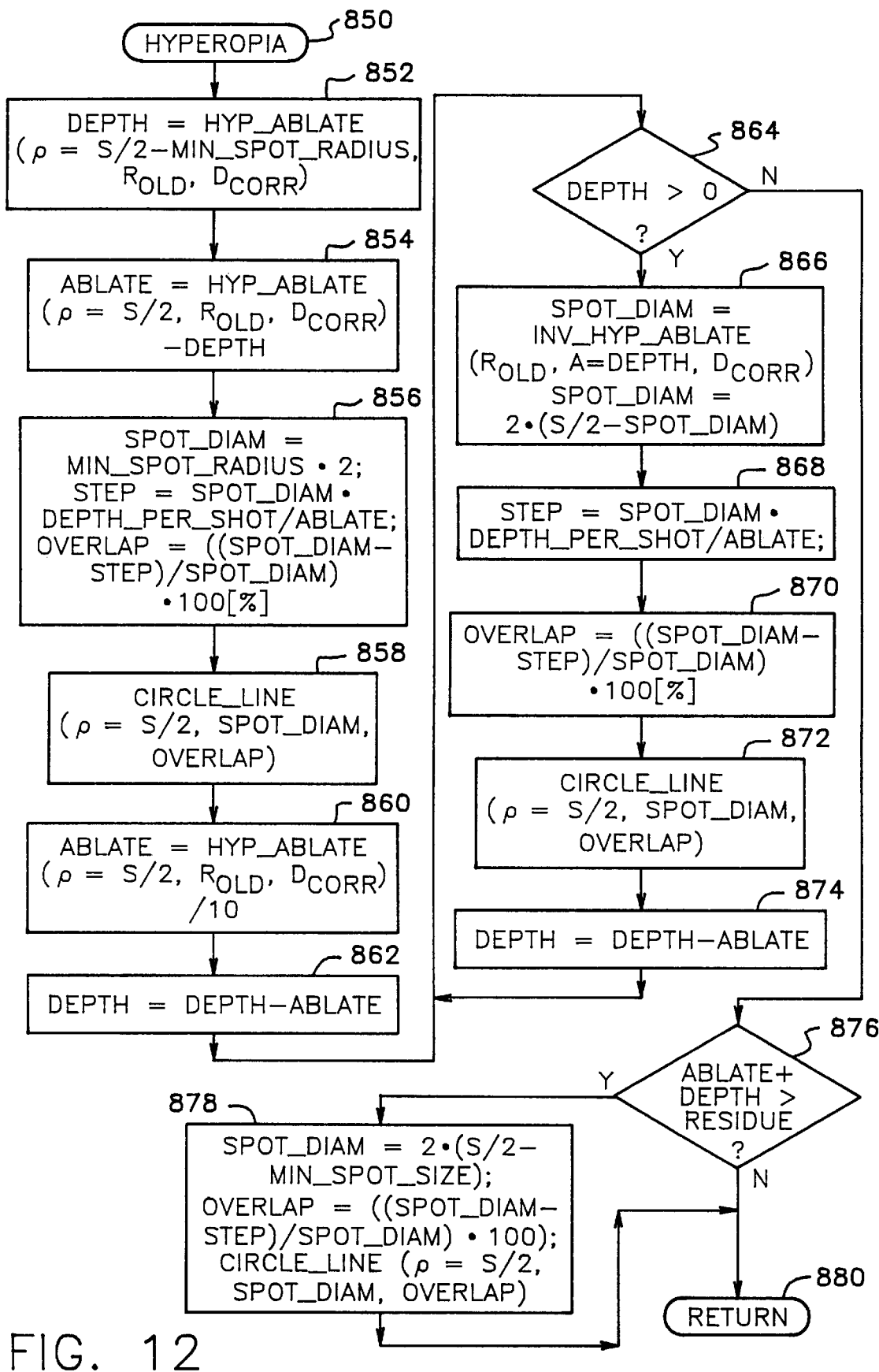
FIG. 12 is a flowchart illustrating a hyperopia routine used by the calculation routine of FIG. 9.

FIG. 12 is a flowchart of the HYPEROPIA routine 850 that creates circular trenches about the axis of treatment 102. It is similar to the ASTIGMATISM routine 750, but creates the circular trenches of an appropriate profile to correct for hyperopia rather than for astigmatism (which uses a myopia correction function).

Beginning at step 852, a variable DEPTH is set equal to the parameter returned by HYP_ABLATE discussed above in conjunction with FIG. 7B, when ρ is set equal to S/2−MIN_SPOT_RADIUS, where S is the diameter of the appropriate area of treatment and MIN_SPOT_RADIUS is the minimum spot size to ever be used for hyperopia ablation, which could be set, for example to 200 µm. HYP_ABLATE is also called with $R_{OLD}$ representing the uncorrected curvature of the eye 44 and $D_{CORR}$ representing the desired degree of dioptric correction. DEPTH thus equals the remaining depth to ablate. It is initially less than the total depth to ablate, as ρ was set just inside the circle of ablation as indicated by S/2 with MIN_SPOT_RADIUS subtracted, which is the first spot radius at which to ablate.

Proceeding to step 854, a variable ABLATE, which indicates the amount to ablate for this hyperopia treatment, is set equal to a parameter returned by HYP_ABLATE called with ρ equal to S/2, with that returned parameter decreased by the amount DEPTH. Thus, ABLATE is the difference in depth at the edge of the area of treatment as indicated by S/2 and the depth at a distance MIN_SPOT_RADIUS just inside that treatment area.

Proceeding to step 856, a variable SPOT_DIAM is set equal to MIN_SPOT_RADIUS·2, a variable STEP is set equal to SPOT_DIAM·DEPTH_PER_SHOT/ABLATE, and a variable OVERLAP is set equal to ((SPOT_DIAM−STEP)/SPOT_DIAM)·100 (i.e., expressed as percent). Thus, the first circular trench will be shot using the minimum spot diameter as indicated by MIN_SPOT_RADIUS·2.

Proceeding to step 858, a routine CIRCLE_LINE is called which calculates the series of shots necessary to ablate a circular trench given the variables SPOT_DIAM, STEP, and OVERLAP. The CIRCLE_LINE routine directly corresponds to the LINE routine 800, except that the circle is shot at a fixed radius given by S/2, instead of being shot along a line. Its implementation corresponds to the LINE routine 800, with the exception that each succeeding shot is incremented along the radius of ρ equal to S/2, rather than along a line.

Proceeding to step 860, ABLATE is set equal to a parameter returned by HYP_ABLATE when HYP_ABLATE is called with ρ equal to S/2, with that returned parameter then divided by 10. This corresponds to preferably ten trenches being ablated to form the appropriate profile of curvature to correct for hyperopia.

Proceeding to 862, DEPTH is then set to DEPTH minus ABLATE, which reduces DEPTH by 1/10th of the total depth needed to ablate the hyperopic trench.

The routine 850 then proceeds to step 864, where it is determined whether DEPTH, which indicates the total depth remaining to ablate, is greater than zero. If so, then there remaining trenches to ablate, so the routine proceeds to step 866, where SPOT_DIAM is set equal to the parameter returned by INV_HYP_ABLATE when that function is called with A equal to DEPTH. This then returns the radius at which ablation must occur to a depth equal to the current value of DEPTH in order to provide the appropriate correction for hyperopia. This returned parameter, however, is a radius from the axis of treatment 102. To calculate the actual spot diameter, SPOT_DIAM is set equal to 2·(S/2−SPOT_DIAM). This sets SPOT_DIAM to two times the difference of the radius of the actual zone of treatment minus the radius at which the current ablation depth is to occur. This difference in radii times two is thus equal to the spot diameter for the current trench to ablate.

Proceeding to step 868, STEP is set equal to SPOT_DIAM·DEPTH_PER_SHOT/ABLATE. Proceeding to step 870, OVERLAP is set equal to ((SPOT_DIAM−STEP)/SPOT_DIAM)·100, which sets the appropriate overlap in percent.

Using these values of SPOT_DIAM and OVERLAP, and with ρ equal to S/2, at step 872 the routine CIRCLE_LINE is called, creating a circular trench. Proceeding to step 874, DEPTH is again set equal to DEPTH minus ABLATE. The routine then loops to step 864, and continually loops through steps 866 through 874 until DEPTH is not greater than zero.

When DEPTH is not greater than zero at step 864, the routine 850 proceeds to step 876, where it is determined whether ABLATE plus DEPTH is greater than RESIDUE, where RESIDUE is an arbitrary value at which another trench is not to be ablated. This value is preferably 500 microns, although could be a different value. If ABLATE plus DEPTH is greater than RESIDUE, then more than that RESIDUE value remains to be ablated, so the routine 850 proceeds to step 878, where a final trench is created using a SPOT_DIAM of 2·(S/2−MIN_SPOT_SIZE) and an OVERLAP of ((SPOT_DIAM−STEP)/SPOT_DIAM)·100. Then from step 876 and step 878, the routine returns at step 880.

Figure 13:
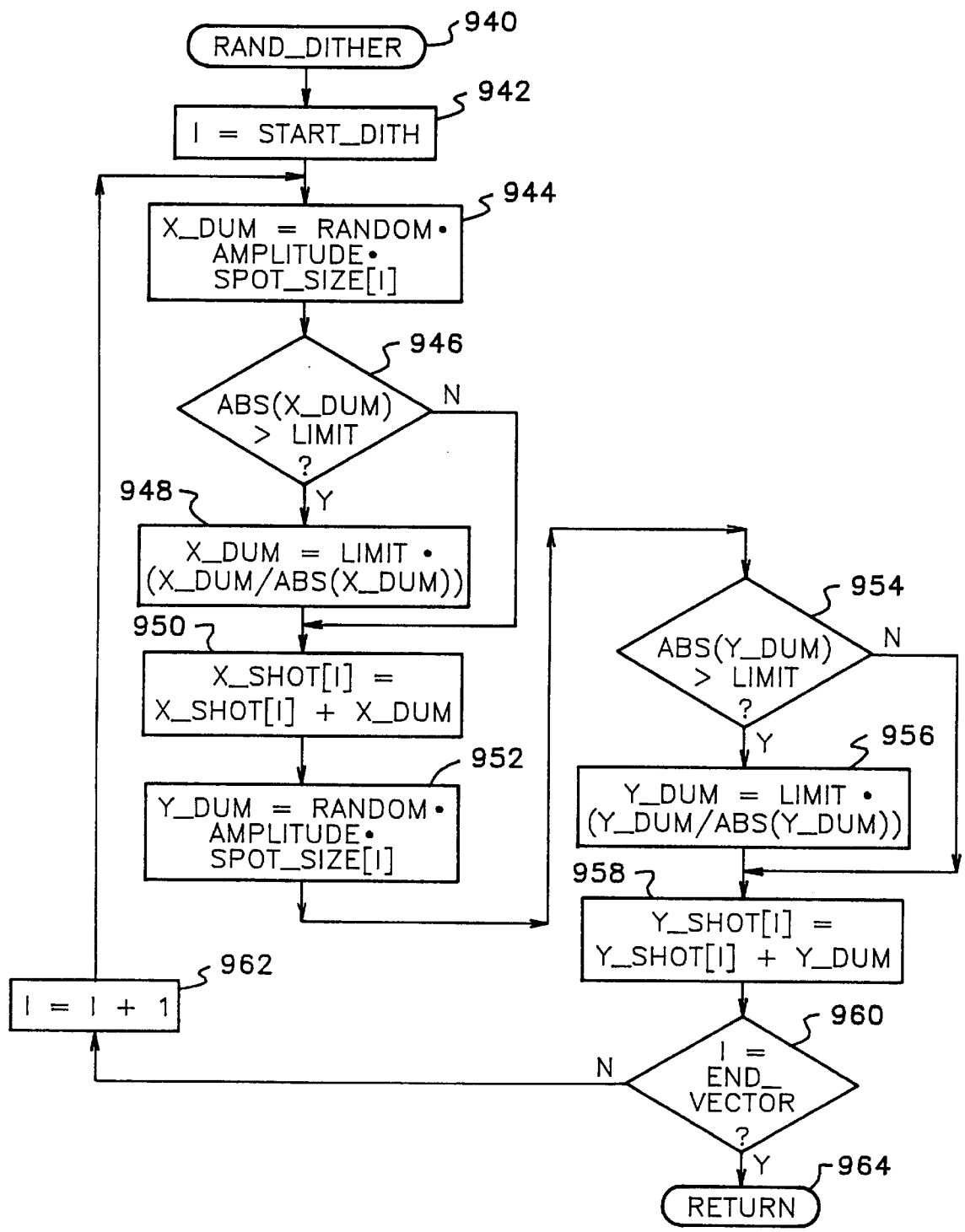
FIG. 13 is a flowchart of a random dithering routine used by the calculation routine of FIG. 9.

FIG. 13 is a flowchart of a RAND_DITHER routine 940 which corresponds to the DITHER routine as noted in step 722 of FIG. 9. The RAND_DITHER routine 940 randomly dithers all vectors in the described array from START_DITH to LAST_VECTOR. START_DITH was previously set at step 702 or step 708 of FIG. 9 to be equal to the first array location following shots used for correction of astigmatism. Thus, dithering is preferably applied to the myopia correction, rather than to the astigmatism correction. The RAND_DITH routine 970 creates a shot pattern as is illustrated in FIG. 3A.

The RAND_DITHER routine 940 begins at step 942 by setting a counter variable I to START_DITH. Control then proceeds to step 944, where an intermediate variable X_DUM is set equal to a random number RANDOM between −0.5 and 0.5 times AMPLITUDE times SPOT_SIZE[I]. The variable AMPLITUDE was passed to the RAND_DITHER routine 940 as indicating the appropriate amplitude of dithering in fractional percentage of spot size, and SPOT_SIZE[I] corresponds to the spot size for this particular shot.

Control then proceeds to step 946, where the routine 940 determines whether the absolute value of X_DUM is greater than a limiting size denoted by a variable LIMIT, which is predetermined by the system. If X_DUM is too large, control then proceeds to step 948, where X_DUM is set equal to LIMIT X_DUM/ABS(X_DUM), which sets X_DUM to LIMIT with the appropriate sign appended.

If X_DUM was not too large in step 946, and in any case from step 948, control then proceeds to step 950, where X_SHOT[I] is set equal to X_SHOT[I]+X_DUM, which provides a random dithering effect according to the invention. Control then proceeds to steps 952, 954, 956, and 958, where Y_SHOT[I] is adjusted with the random dithering as X_SHOT[I] was dithered at steps 944 through 950.

Control then proceeds from step 958 to step 960, where the RAND_DITHER routine 940 determines if I=LAST_VECTOR, indicating that the last vector desired has been dithered. If not, control proceeds to step 962, where I is incremented, and control then loops to step 944 to process the next shot.

If at step 960 I equals LAST_VECTOR, the RAND_DITHER routine 940 is complete, so the routine 940 then returns at step 964.

Figure 14:
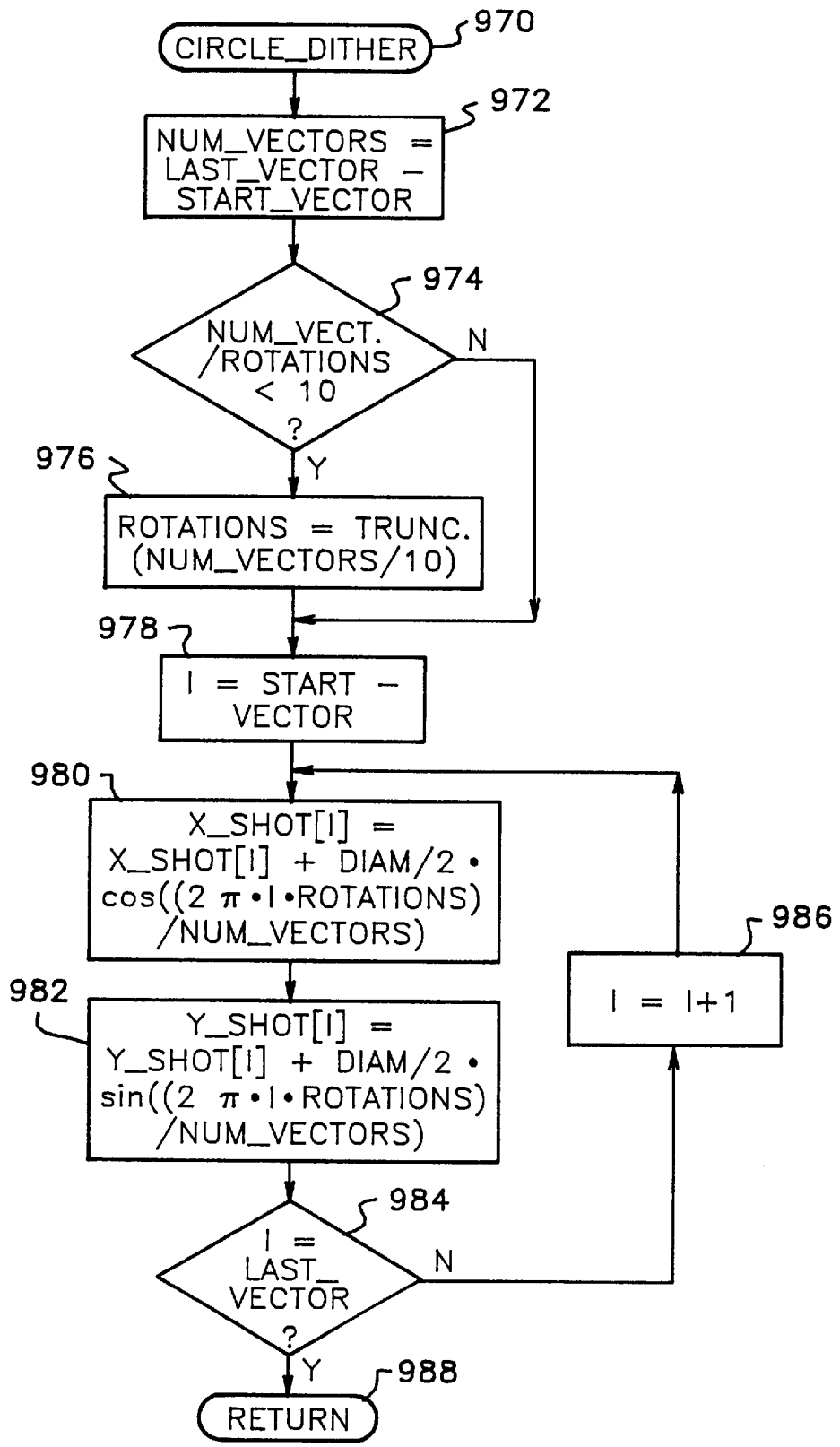
FIG. 14 is a flowchart of a circular dithering routine used by the calculation routine of FIG. 9.

FIG. 14 shows an alternative routine CIRCLE_DITH 970, which can be used instead of the RAND_DITH routine 940. A shot pattern as created by the CIRCLE_DITH routine 970 is illustrated in FIG. 3B. The CIRCLE_DITH routine 970 begins at step 972, where a variable NUM_VECT is set LAST_VECTOR−START_VECTOR, both of which were passed by the calling routine. Proceeding to step 974, it is determined whether NUM_VECT/ROTATIONS is less than 10. The variable ROTATIONS is passed to the routine 970 to indicate how many circular rotations to make around the axis of treatment 102 in adjusting all of the shots. The check is made at 974 to prevent an excessive number of rotations if there are insufficient shots. For example, if there are only twenty vectors, ten revolutions would result in two sets of ten shots each 180° apart. By arbitrarily requiring NUM_VECT/ROTATIONS to be at least 10, this prevents such accumulation of shots, requiring the shots be distributed over at least ten different points around the axis of treatment 102. If NUM_VECT/ROTATIONS is less than 10, control proceeds to step 976, where ROTATIONS is set equal to the truncated value of NUM_VECT/10. From step 976 and 974, if that step was not true, control then proceeds to step 978, where I is set equal to START_VECTOR.

Control then proceeds to step 980, where X_SHOT[I] is set equal to X_SHOT[I]+(DIAM/2)·cos((2π·I·ROTATIONS)/NUM_VECT). This circularly adjusts the center of each shot. Y_SHOT[I] is correspondingly adjusted in step 982.

From step 982, control proceeds to step 984, where it is determined whether I is equal to LAST_VECTOR. If not, control then proceeds to step 986 where I is incremented for another pass through steps 980 and 982 to adjust subsequent vectors.

If from step 984 I is equal to LAST_VECTOR, control then proceeds to step 988, where control returns to the CALCULATE routine 700.

It will be readily appreciated that this dithering, or oscillation, could also be applied one dimensionally, and could be used for hyperopia and astigmatism correction as well.

Figure 15:
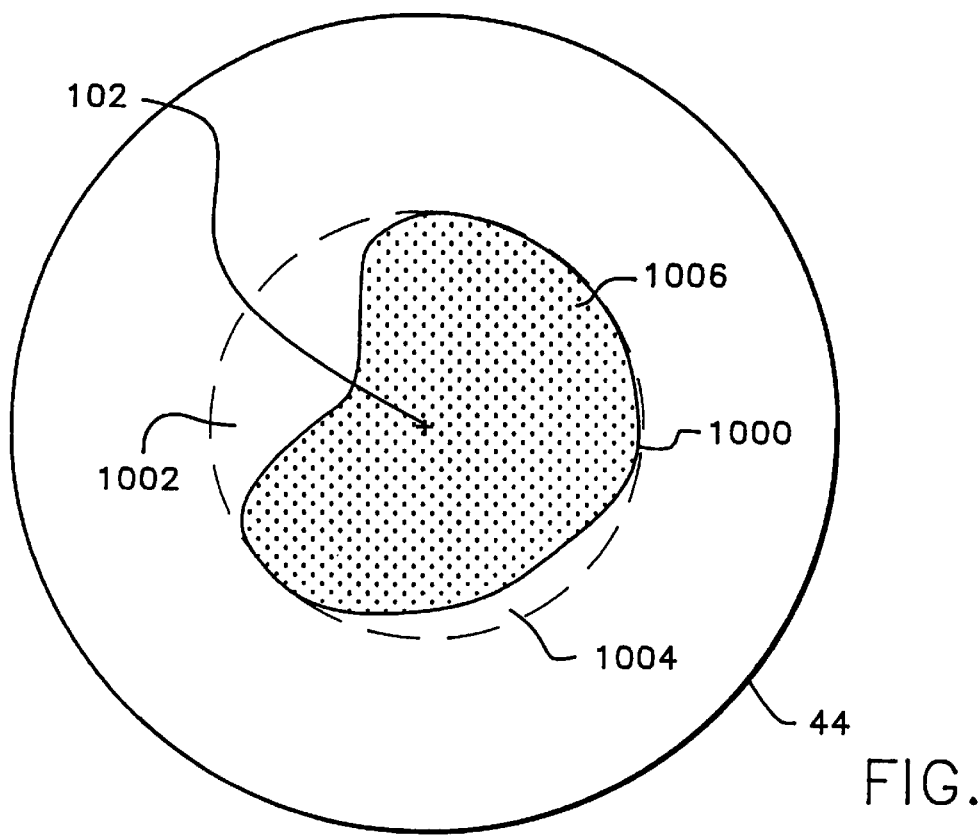
FIGS. 15 and 16 are views along the axis of treatment of the eye illustrating ablation of the epithelium according to the invention.

FIG. 15 illustrates an image returned by the video unit 56 in performing epithelia ablation using infrared dye and using the scanning large beam according to the invention. The epithelium is typically approximately 50 $\mu$m thick. As the preferred excimer laser 20 used in the system S according to the invention ablates approximately 0.2 $\mu$m per shot, 250 initial shots will typically be needed until the epithelium has been ablated. At some time before that point, however, variations of the epithelia thickness come into play. For example, some points might be 40 $\mu$m thick, while others are 60 $\mu$m thick.

The system S according to the invention removes the epithelium by sensing when it has completely removed at least a portion of the epithelium, and then selectively removing the remainder. FIG. 15 illustrates an epithelial removal zone 1000 in which a predetermined number of shots have been previously performed using a spot size the size of the epithelial removal region 1000. After each shot, the infrared video unit 56 captures any infrared fluorescence emitted from the eye 44. This fluorescence is created by first dyeing the epithelium with an infrared fluorescent dye that does not dye the layers underlying the epithelium. This dye is preferably infrared fluorescent to reduce the possibility of a pumped lasing action into the eye 44 of damaging frequencies of light at damaging energies. Other dyes could be used, including visible light emitting dyes, if it is ensured that no pumped lasing action will occur that might damage the eye 44. Infrared fluorescent dye is also preferred to prevent any distracting optical affects to the patient while the epithelium is being ablated.

After a predetermined number of shots, the video unit 56 will detect some portion of the epithelial removal region 1000 that does not fluoresce. This indicates that there is no infrared fluorescent dye at that location, which correspondingly indicates the epithelium has been entirely ablated at that point.

In FIG. 15, two regions 1002 and 1004 are shown in which all of the epithelium has been removed by the predetermined number of shots. At this point, the spot size is reduced, and a region 1006 in which the epithelium still remains, as indicated by the infrared fluorescent dye, is further ablated.

Figure 16:
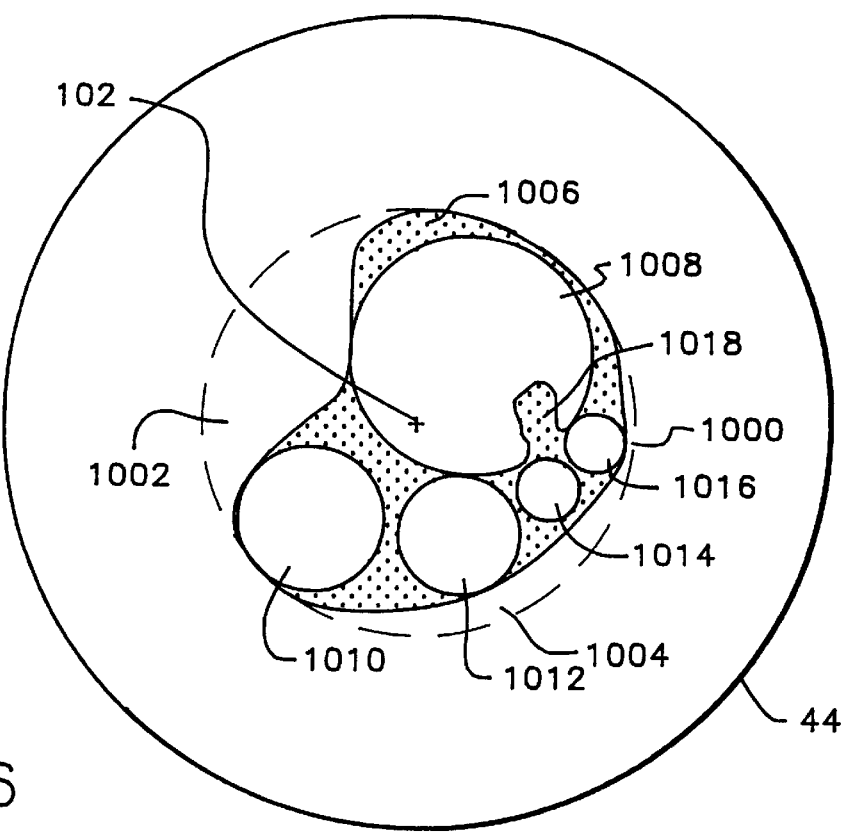

Either under computer control or under physician control, the selective ablation is performed as illustrated in FIG. 16. In FIG. 16, the remaining region 1006 has been further ablated using reduced spot sizes, forming further epithelial free regions 1008, 1010, 1012, 1014, and 1016. The video unit 56 further observes the epithelial removal region 1000 during ablation of each of these remaining regions, detecting when a certain portion of those regions do not fluoresce. Again, differences in epithelial depth across each of these regions can result in only partial ablation of the epithelium in these remaining regions. For example, an island 1018 of epithelium is shown remaining in the region 1008 which has been further ablated. Such islands must be further ablated, along with any remaining portion of the epithelium 1006 which has not been removed by the subsequent ablation.

It will be recognized that by keeping a computer map of the epithelial removal region 1000, along with the number of shots fired onto each particular point in that region, a map of epithelial thickness can be created. By knowing the ablation depth of each shot, along with where each shot has been fired, it is known how many shots a particular point receives before all of the epithelium is removed from that region. Thus, a map of the thickness of the epithelium is created. This map would be similar to that created in correcting for non-symmetrical optical aberrations as discussed in conjunction with FIG. 8.

It will be appreciated that the large beam scanning and dithering according to the invention need not only be applied to the surface of the eye 44. For example, U.S. Pat. No. 4,903,695, entitled "Method and Apparatus for Performing a Keratomileusis or the Like Operation," issued Feb. 27, 1990, discloses a method of removing a portion of the cornea from the eye and then ablating the exposed surface. Thus, the method and apparatus according to the invention can also be used on the exposed surface resulting from such a Keratomileusis type procedure. In such a case, the axis of treatment 102 would fall either on either the severed portion of the cornea or on the surface of the cornea from which a portion had been severed.

FIG. 17 is perspective view of a lens ablation pattern 1100 according to the invention for correcting for myopia. FIG. 17 illustrates in perspective greater ablation depth corresponding to the height of the perspective drawing. The lens ablation pattern 1100 is created by creating two standard astigmatism ablation patterns 1104 and 1106 (i.e., "cylindrical lenses") as illustrated and discussed in conjunction with FIGS. 4A, 4B, 10A, 10B, and 11. These two standard astigmatism ablation patterns 1104 and 1106 are preferably created at right angles to one another.

The lens ablation pattern 1100 includes a central region 1102 where the two standard astigmatism ablation patterns 1104 and 1106 intersect. The central region 1102 preferably encompasses the optically active area of the treatment zone, while the arms of the standard astigmatism ablation patterns 1104 and 1106 extend outward from that treatment zone.

FIG. 18A is a top view of the perspective view of FIG. 17. As can be seen, the central region 1102 encompasses an optically active area 1200 of the treatment zone. It is preferable that the optically active area 1200 resides within the central region 1102 where the two standard astigmatism ablation patterns 1104 and 1106 intersect, but that is not absolutely necessary, as a small portion of the central region 1102 could extend into the separate arms of the standard astigmatism ablation patterns 1104 and 1106.

FIG. 18A also shows a transition zone 1202, which would correspond to extra ablation on the sides of each of the standard astigmatism ablation patterns 1104 and 1106 to provide a smooth transition zone, preventing ridges, as discussed above in conjunction with FIGS. 2B and 9.

FIGS. 18B and 18C show end-on views of each of the standard astigmatism ablation patterns 1104 and 1106, along with the central region 1102.

When two standard astigmatism ablation patterns 1104 and 1106 are created at right angles, the central region 1102 results in a lens with the focusing properties of the standard spherical lens used to correct myopia. For example, if two −2.00 diopter standard astigmatism ablation patterns 1104 and 1106 are ablated at right angles, the resulting central region will be a −2.00 diopter myopia correcting lens.

It is believed that by creating the cylindrical lens in the central region 1102 through the two standard astigmatism ablation patterns 1104 and 1106, central islands can be minimized. In any case, use of the two standard astigmatism ablation patterns 1104 and 1106 to create a lens with spherical lens properties further increases the advantages of large-beam scanning dithering, as described above in conjunction with FIGS. 3A, 3B, 4A, and 4B.

Further, astigmatism can also be treated by providing a lower diopter correction for one of the standard astigmatism ablation patterns 1104 or 1106 than the other. For example, use of −1.00 diopter correction at 90° and −2.00 diopter correction at 0° will result in −1.00 diopter of myopia correction with an additional −1.00 diopter of astigmatism correction at 0°.

Ablation of the cylindrical lenses that form the standard astigmatism ablation patterns 1104 and 1106 at angles other than 90° to one another also creates a lens that corrects for myopia while simultaneously providing further correction for astigmatism. For example, a −2.00 diopter correction at 0° in conjunction with a −2.00 diopter correction at 45° results in a −0.59 diopter correction for myopia with a further −2.83 diopter correction for astigmatism at 22.5°. Similarly, a −2.00 diopter correction at 0° in conjunction with a −2.00 diopter correction at 10° results in a −0.03 diopter correction for myopia in conjunction with a −3.94 diopter correction for astigmatism at 5°. These are calculated using standard formulas based on adding lenses, as are known to the art.

It will be appreciated that whatever the method used to create the standard astigmatism ablation patterns 1104 or 1106, whether large-beam scanning or the various types of apertures disclosed in the background, such as a variable-width slit aperture of rectangular shape, the resulting central region 1102 will have the appropriate properties for treating myopia. Whatever the method or technique used for creating the cylindrical lenses, the intersecting cylindrical lenses form an appropriate corrective pattern.

By reversing the process, that is by creating the inverse of the standard astigmatism ablation patterns 1104 and 1106 using the various techniques described, or other known techniques, hyperopia can likewise be corrected. This would be achieved by using standard astigmatism ablation patterns 1104 and 1106 of positive diopter.

Figure 27:
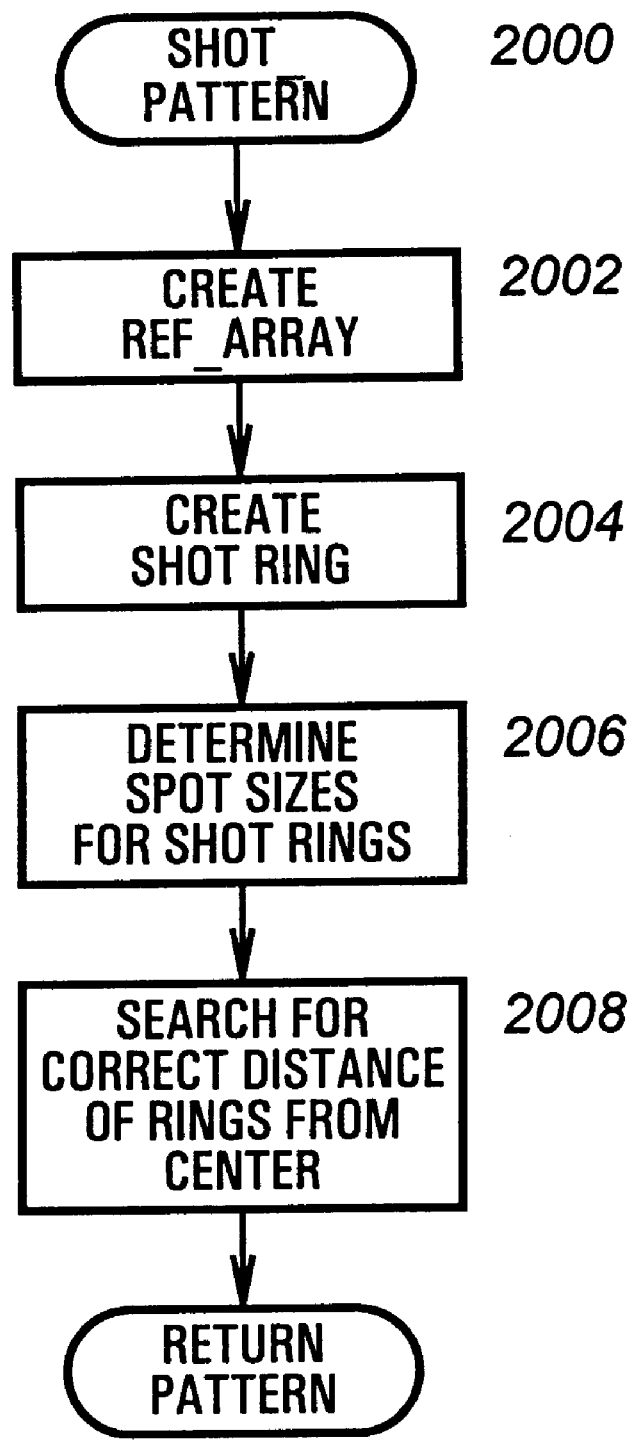
FIG. 27 is a flow chart illustration of a search routine used to generate shot patterns according to the invention.
Figure 28:
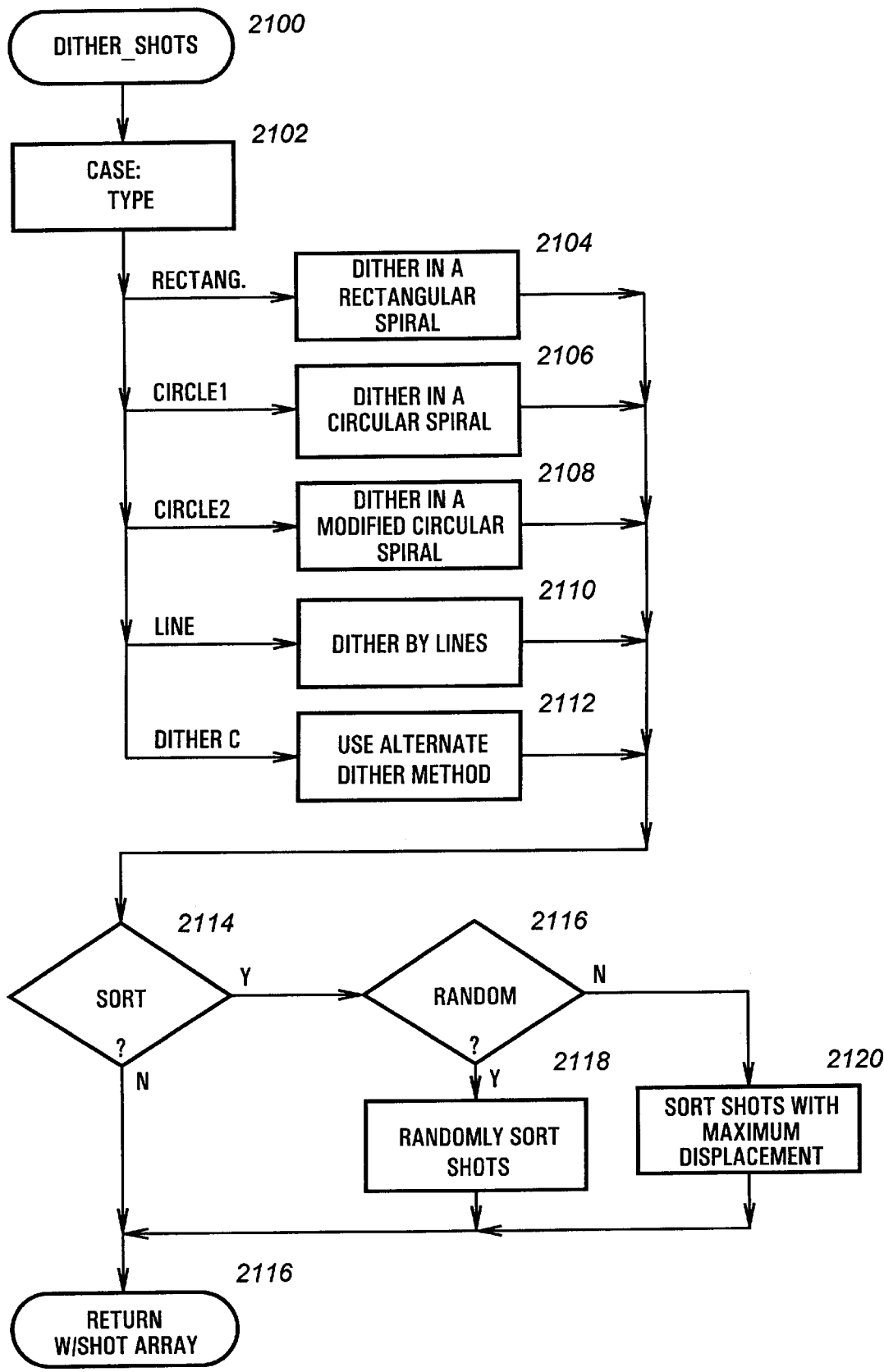
FIG. 28 is a flow chart illustration of a shot dithering routine used to generate shot patterns according to the invention.

Turning now to FIGS. 19 through 24, these Figures illustrate the center points of shot patterns calculated by a ring searching algorithm further discussed below in conjunction with FIG. 27 and a dither shot pattern algorithm further discussed below in conjunction with FIG. 28. These programs generate a number of shot patterns with center locations away from the center point of the treatment area, and also using fixed spot sizes according to the invention. It will be appreciated that a large, fixed spot size is used with center locations of shots as far as 2.5 mm from the center of the treatment zone. It will also be appreciated that by using a large spot size, the greatest area of tissue is ablated per shot, requiring fewer shots. It will further be appreciated that the ridging effects that are reduced by using the dithering according to the invention discussed earlier in conjunction with FIGS. 3A and 3B, is even further eliminated by the searching and shot dithering according to the invention, as these shot patterns produce virtually no reinforcing ridges. The programs illustrated by the flowcharts of FIGS. 27 and 28 are attached as Appendices A, B, and C. The program of FIG. 27 and attached Appendix A generates shot patterns by empirically determining a series of rings containing shots that will satisfy a desired ablation pattern. The program attached as Appendix B and illustrated in FIG. 28 distributes fixed sized shots over the treatment area using a shot dithering pattern, with a variety of different shot dithering patterns available. Further, the program attached as Appendix C and illustrated in FIG. 28 provides for either randomly sorting the resulting shot patterns or sorting the shot patterns with maximum displacement between sequential shots. Further, by displacing subsequent shots from each other, rather than having a particular point in the shot pattern always being ablated, and rather than having each subsequent shot overlap an immediately previous shot, thermal heating is reduced, allowing for greater shot rates.

Figure 19:
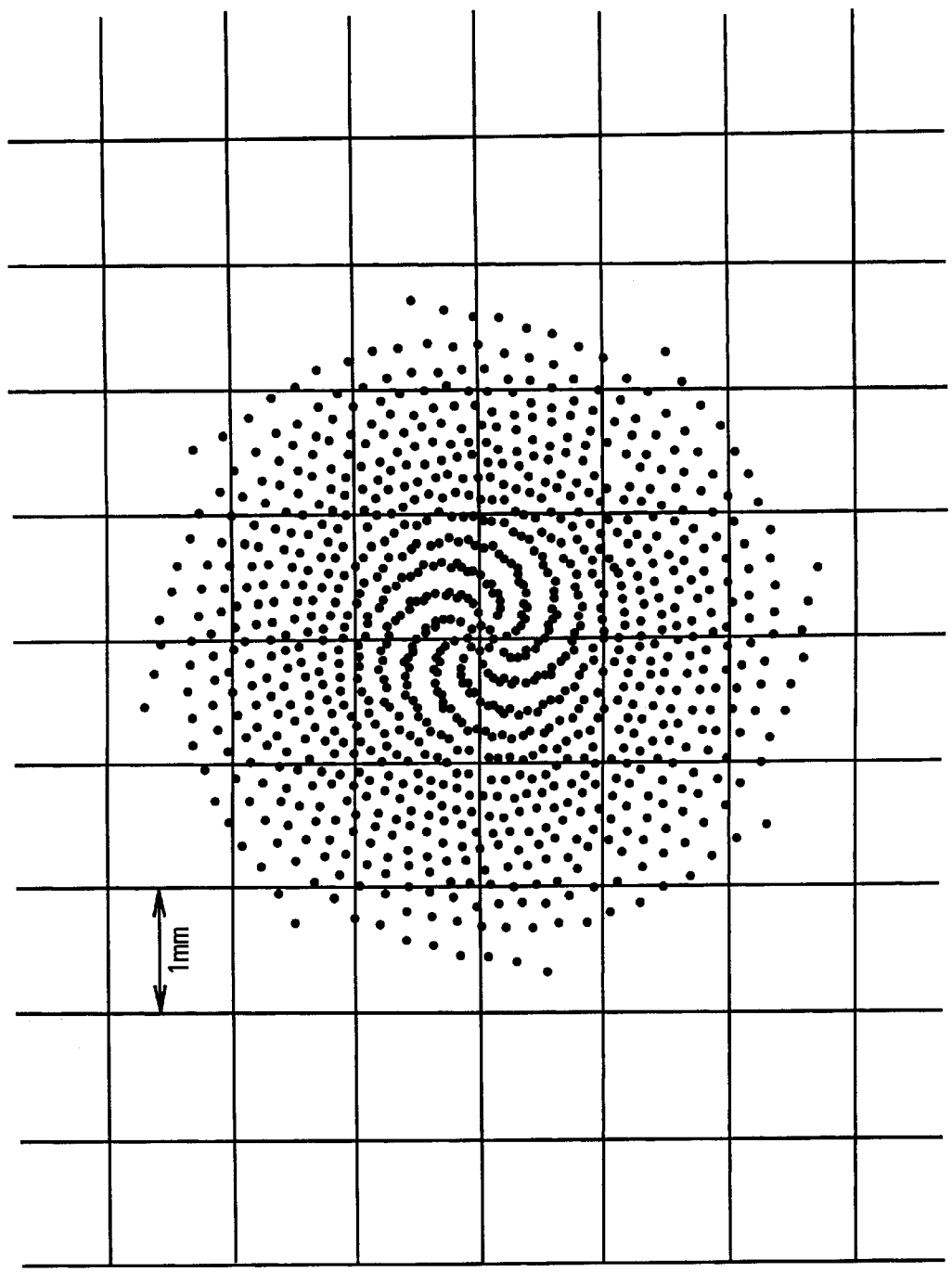
FIG. 19 is an illustration of a shot pattern according to the invention using a constant spot size of 2.0 mm to correct −5 diopters using a spiral shot dithering pattern according to the invention.
Figure 20:
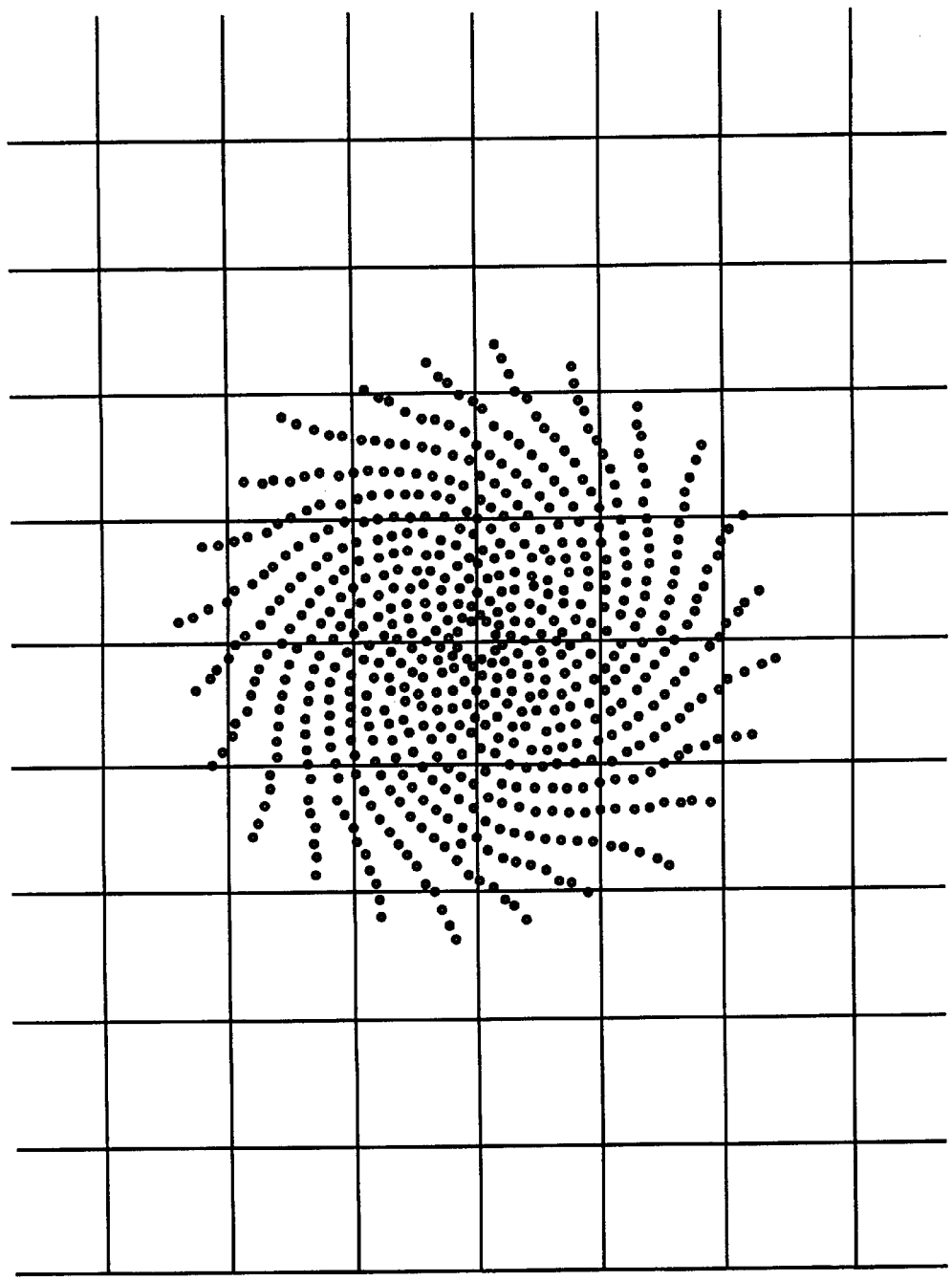
FIG. 20 is an illustration of a shot pattern according to the invention using a constant spot size of 2.0 mm to correct −5 diopters using a slightly different form of spiral shot dithering pattern according to the invention.
Figure 21:
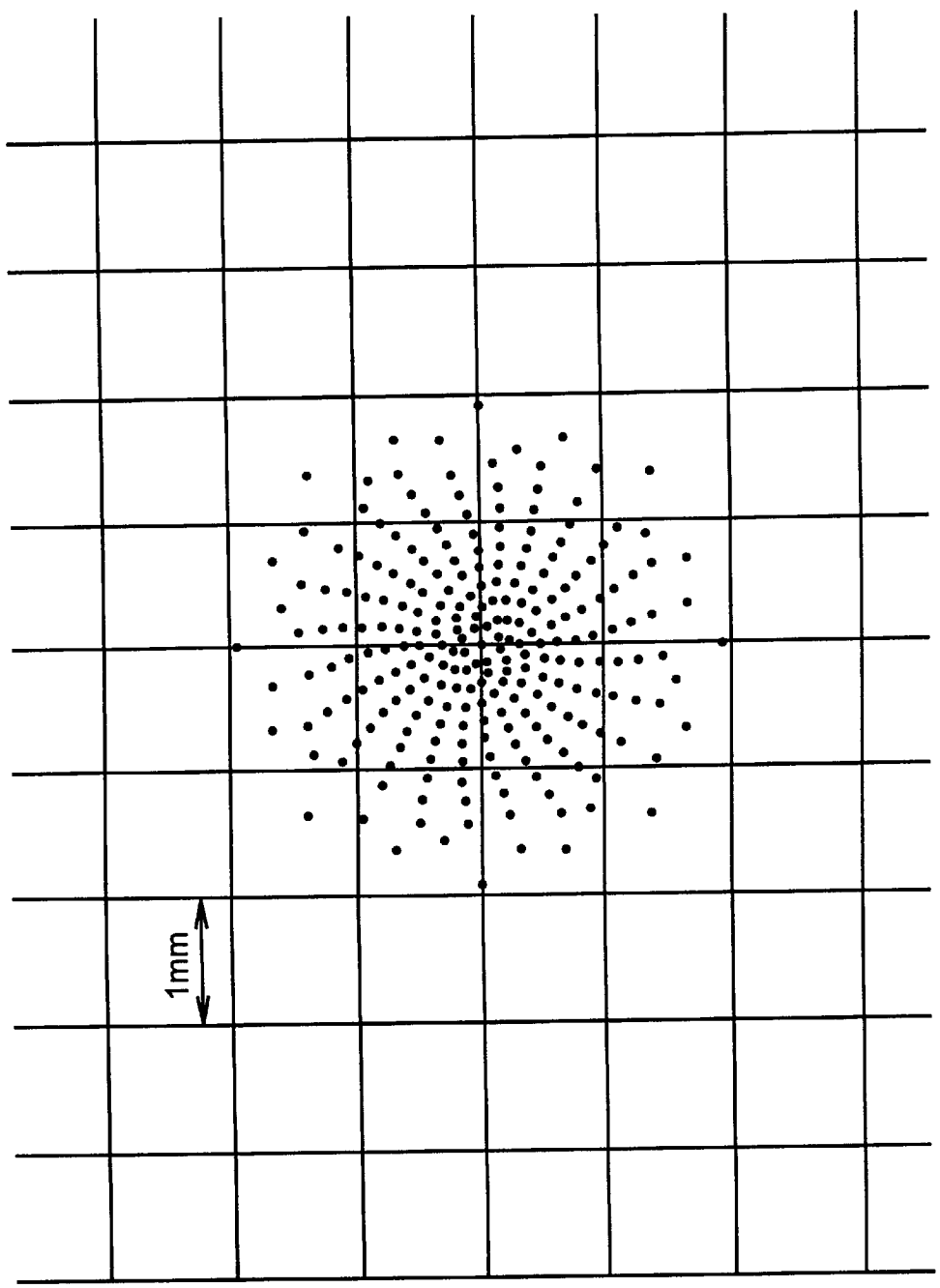
FIG. 21 is an illustration of a shot pattern according to the invention using a constant spot size of 4.25 mm to correct −5 diopters using the search algorithm according to the invention.
Figure 22:
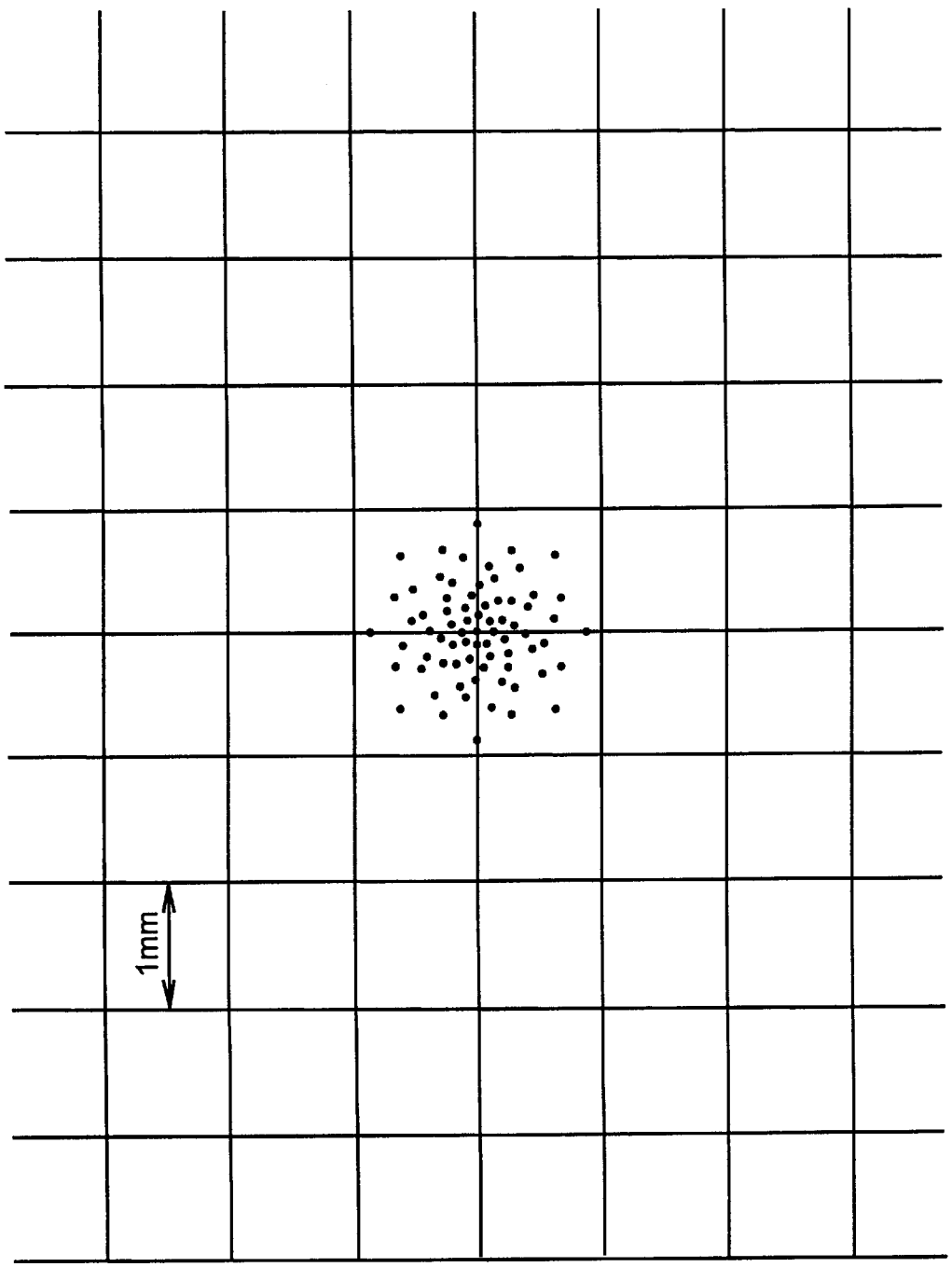
FIG. 22 is an illustration of a shot pattern according to the invention using a constant spot size of 2.0 mm to correct −7 diopters using the search algorithm according to the invention.
Figure 23:
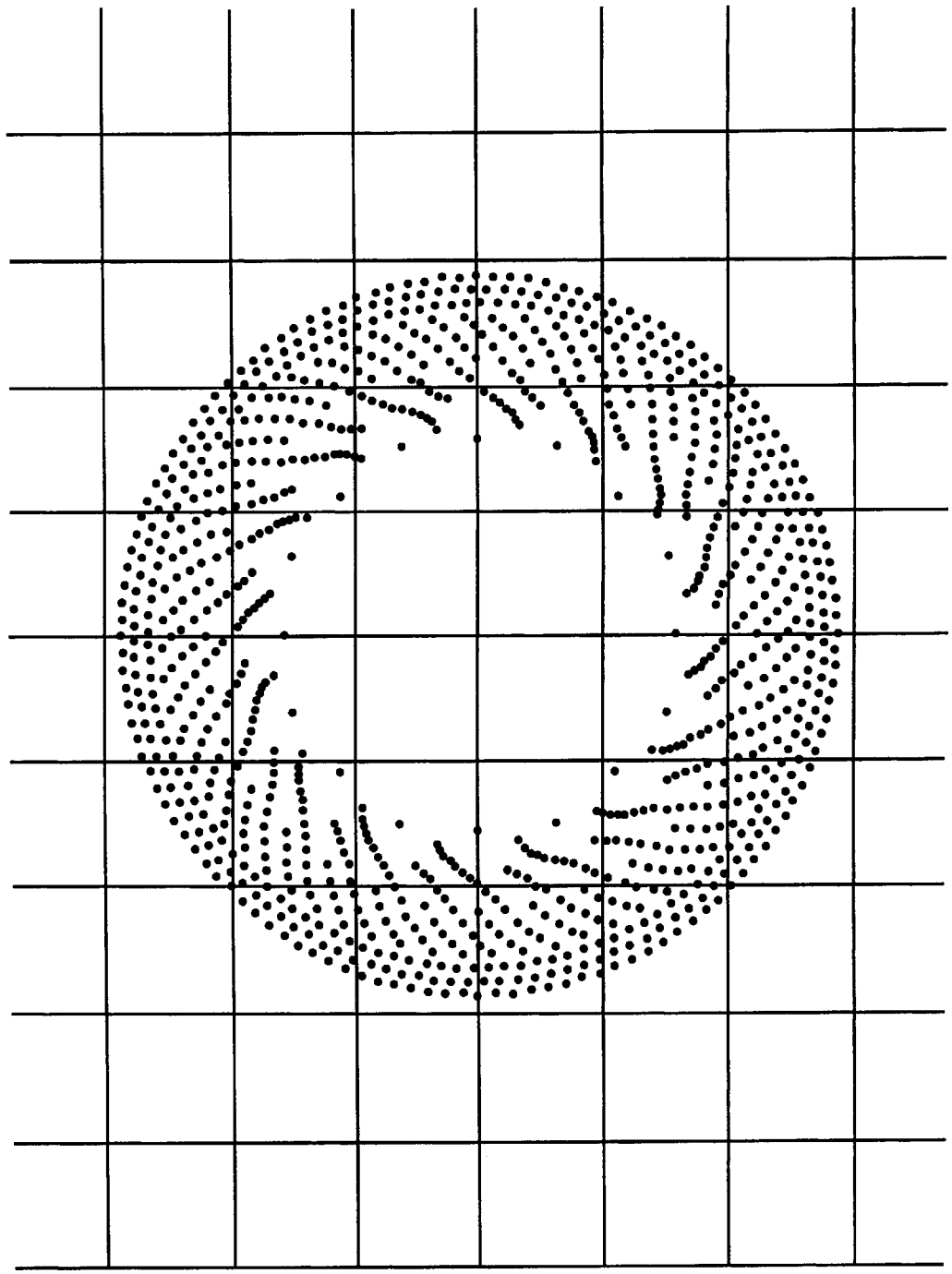
FIG. 23 is an illustration of a shot pattern according to the invention using a constant spot size of 2.0 mm to correct +5 diopters using the search algorithm according to the invention.

FIGS. 19 through 25 illustrate various shot patterns produced by the programs illustrated in FIGS. 27 and 28. FIGS. 19 and 20 illustrate shot patterns created using the shot dithering (as opposed to the displacement dithering of FIGS. 3A and 3B) illustrated by the flowchart of FIG. 28. FIGS. 21–23 illustrate shot patterns created by the search algorithm illustrated in FIG. 27. FIG. 19 was created using a constant 2.00 mm spot size to correct to −5.00 diopters. FIG. 20 was similarly created for a 2.00 mm spot size for correction to −5.00 diopters, but using a modified spiral pattern according to the invention and described in FIG. 28.

FIG. 21 was created for a 4.25 mm spot size to correct to −5.00 diopters using the ring searching according to the invention, while FIG. 22 was created for a 2.00 mm spot size to correct to −7.00 diopters using the ring searching according to the invention. FIG. 23 was created using the ring searching algorithm according to the invention to correct for hyperopia, created for a 2.00 mm spot size at +5.00 diopters of correction.

FIGS. 24A, 24B and 24C are a list of shots used to create the treatment pattern of FIG. 21, further illustrating the output of the ring searching algorithm according to the invention. As can be seen, there are no overlapping shots, and the shots in the sequence have been ordered by their X displacement in microns.

Figure 25:
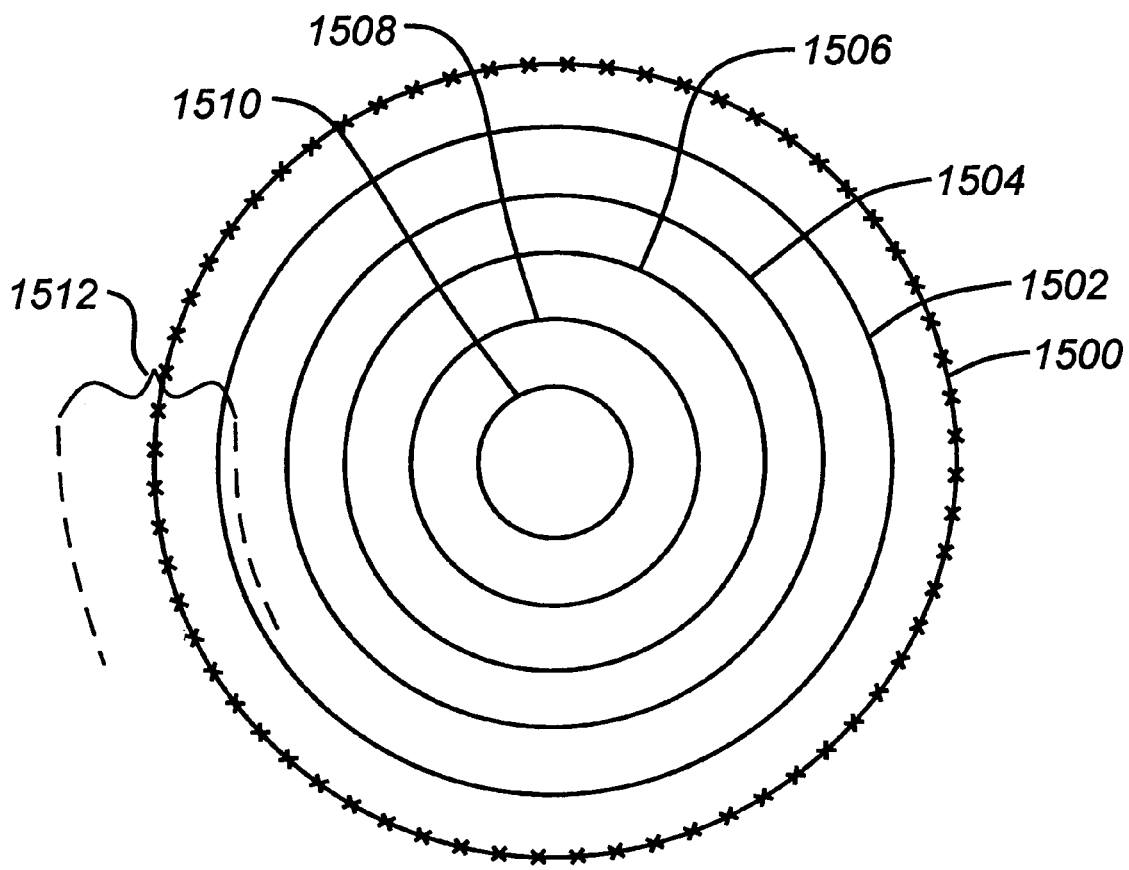
FIG. 25 is a diagram illustrating how concentric rings of overlapping spots are calculated according to the invention.

Turning to FIG. 25, the general steps of how the shot pattern is created by the searching algorithm of FIG. 27. In FIG. 25, it is seen that a number of concentric rings are determined by the search algorithm discussed below in conjunction with FIG. 27. Concentric rings 1500 to 1510 are determined using the program attached as Appendix A. Then, for each ring, the appropriate number of shots is determined. Taking ring 1500 for example, the number of shots needed and their spacing around the ring are calculated in order to correct to the appropriate degree within a particular treatment zone 1512. Then, appropriate shots are calculated for the ring 1502 and so on. In this way, the patterns of FIGS. 21 through 23 are calculated.

Figure 26:
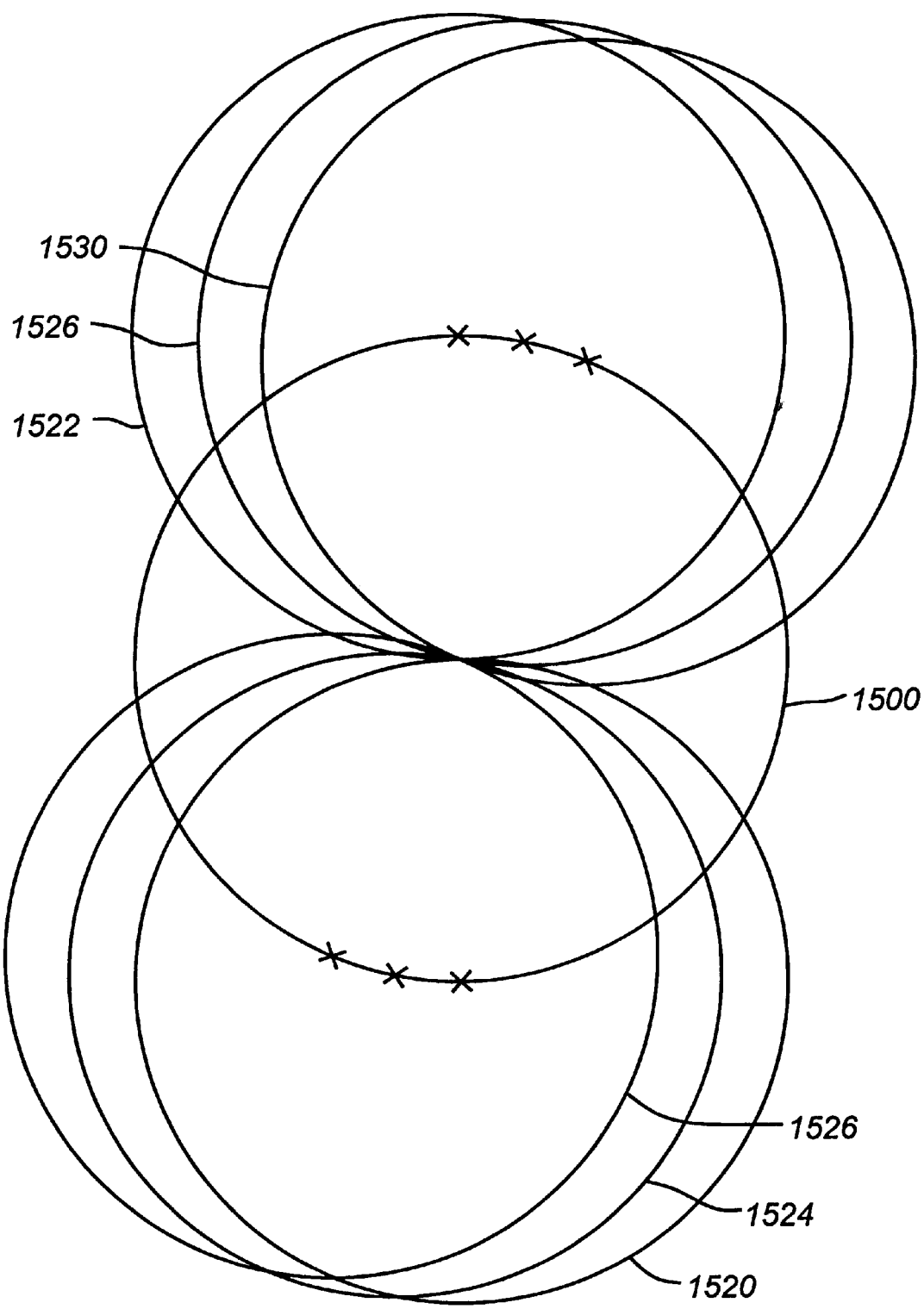
FIG. 26 is a diagram illustrating how concentric rings of overlapping spots are created with each sequential shot not overlapping with the immediately previous shot.

Referring to FIG. 26, it is seen that the ring that is determined includes a number of relatively large shots 1520 to 1530, preferably around 2.0 to 3.5 mm, that overlap around the ring 1500. The maximum shot rate that the tissue on one point of the cornea can typically absorb is 40 shots per second at 0.25 micron per shot of ablation. To increase this rate according to the invention, an alternating pattern is adopted. Other techniques are also described in conjunction with FIG. 27, but the basic concept is shown here. Rather than repeatedly fire at a particular point that might result in the 40 shot per second rate being exceeded, alternating shots are fired on opposite sides of the ring, for example. Referring to FIG. 27, an actual shot pattern used is shown. As is seen, the first shot 1520 is fired on the bottom of the pattern, then the second shot 1522 then is fired on the top of the pattern adjacent to, but not overlapping, the first shot 1520, the third shot 1522 is fired on the bottom of the pattern overlapping the first shot 1520. Further, overlapping patterns can then be fired, again using this alternating technique. The point behind this technique is to create the series of overlapping shots of FIGS. 25 and 26 without each subsequent shot actually overlapping the previous shot fired. Further according to the invention, each particular spot, shot 1520, for example, generally is a series of shots. But rather than fire a series of shots in succession, the entire ring can be created using single alternating shots as illustrated in FIG. 26, but repeating the pattern created by this series of single alternating shots of FIG. 26 as is needed for the particular ring 1500. In this way, instead of completing the ablation at one particular point, the ablation is distributed, and higher shot rates can be realized. It will be understood that when shots are needed close to the center of the pattern, as is illustrated by the ring 1510 in FIG. 25, it may not be possible to prevent a single point from being continuously ablated by displacing these shots. In such a case, it would be desirable to slow down the shot rate.

Turning to FIG. 27, the general flow of the program attached as Appendix A is shown. A routine SHOT_PATTERN 2000 empirically calculates a shot pattern necessary to ablate to the desired degree of correction. The main procedure is the procedure "Search" illustrated at lines 1107 to 1176 of the attached Appendix A. SHOT_PATTERN 2000 begins at step 2002 where a reference array indicating the necessary degree of ablation is calculated based on the desired amount of correction. This step corresponds to the procedure "FillReferenz", called at line 1145 and found at lines 314 to 378 of the attached Appendix A. This procedure creates a reference array indicating the necessary degree of ablation at each point of the treatment area to accomplish the desired degree of correction. It will be understood to those of ordinary skill in the art what the particular degree of ablation necessary to correct for hyperopia or myopia is, and in any case, the necessary equations are found in this specification.

Then, SHOT_PATTERN 2000 proceeds to step 2004, where it creates shot rings. This corresponds to the procedure "Verteilen", which is called at line 1161 and is shown at lines 394 to 462 of the attached Appendix A. This procedure partitions the spirals or rings into a maximum of 32 rings.

Proceeding to step 2006, the spot sizes for each of the rings is then calculated by a procedure "BlendenVorbelegung". Using fixed spot sizes, this will of course result in the same spot sizes for all of the rings. "BlendenVorbelegung" is called at line 1162 of the attached Appendix A, and is shown at lines 523 to 563.

SHOT_PATTERN 2000 then proceeds to step 2008, where it determines the correct distance of the rings from the treatment center. It does so by calling a procedure "Search Rings" at step 1163, which is shown at lines 641 to 969. This is an empirical algorithm for determining the optimal distance of each ring from the center.

Certain of the variables used by SHOT_PATTERN 2000 as illustrated in the attached Appendix A deserve further discussion. DAT_ALL.RHOMAX is a variable in a structure DAT_ALL, which holds the information about the current treatment. DAT_ALL.RHOMAX is a radius of the corrected zone, and typically has a value of 2.5 mm. DAT_ALL.SPH_CORR is the desired spherical correction in diopters, and typically has a value of from −5 to +5. DAT_ALL.VEKTORLAENGE is the length of the treatment vector, which equals the total number of shots and typically has a value between 200 and 1500.

SYSDATA.RATE is the ablation per shot. It is typically 0.25 microns, and is machine dependent.

VOLTHEO is the ablation volume of a certain treatment. For example, for a correction of −5.0 diopters within a treatment area with 5 mm diameter, the value is about 0.5 $mm^3$. This value is used in the constant spot mode to determine the "best" spot size using an empirical formula.

The structure RING holds all the information necessary for a particular ring of shots. The smallest treatment element is a "ring". The empirical algorithm can use up to 32 "rings", and it searches for the best ring values. RING.DIST is the mean radius of the ring. RING.SPOT is the spot size for shots used in this ring. RING.COUNT is the number of shots in this ring.

For myopia, the algorithm starts with all shots distributed to identical rings set to a radius of zero. The algorithm then increases the diameter of the rings one by one to get to the closest reference ablation function. For hyperopia, all rings are initially set to 7 mm in diameter and then decrease one by one to get closest to the hyperopia reference ablation function. Thus, the radii of the rings are empirically determined.

MICRO, MAXABL, and ABLSHOT are integer values of various floating point numbers used to speed up the routine. Because the algorithm is a searching algorithm requiring much computational power, the speed is dramatically increased by using integer calculation.

Using these algorithms, a large spot size provides for a greater amount of ablation per shot, while at the same time permitting virtually any treatment pattern to be achieved. A relatively large spot size would be 2.0 mm, thus providing for relatively large coverage of treatment area per shot. It will be appreciated that using such large spot sizes, however, the shots are generally not "adjacent" to each other, but instead overlap to generate the desired degree of ablation at a particular point. It is the calculation of the result of the overlapping shots that is technically challenging and relies on the empirical algorithm described. This is especially true when using a fixed spot size that is relatively large in relation to the treatment area. It will further be appreciated that by using a fixed spot size, the diaphragm 36 can be replaced by simpler equipment that requires less maintenance and adjustment. This is another advantage of using the large, fixed spot size of overlapping shots.

Turning to FIG. 28, an alternative method of calculating treatment patterns using large, fixed spot sizes distributed throughout the treatment area is shown, as well as the use of shot sorting to decrease thermal effects. A routine DITHER_SHOTS 2100 provides for both this shot dithering as well as the sorting. The shot dithering of FIG. 28 is achieved by the program shown in Appendix B, while the sorting is achieved by the program shown in the attached Appendix C.

Proceeding to step 2102, DITHER_SHOTS 2100 performs a case statement depending on the type of shot dithering desired. A number of different types of shot dithering are shown in the program attached as Appendix B, and these distribute the shots throughout the treatment area in a slightly different way.

This case statement is performed in the attached Appendix B at lines 547 to 554. If it is desired to perform a rectangular dithering, indicated by the type of dithering being "RECTANG", DITHER_SHOTS 2100 calls a routine at step 2104 in which the treatment is performed by dithering in a rectangular spiral. This corresponds to the procedure "DO_DITHER_RECT" in the attached Appendix B, at lines 26 through 93.

If it is desired to perform a first type of circular dithering in a spiral, indicated by the type of dithering being "CIRCLE1", DITHER_SHOTS 2100 proceeds to step 2106, where a routine is called that dithers in a circular spiral. In Appendix B. this corresponds to the procedure "DO_DITHER_CIRCULAR", shown at lines 97 through 179.

If it is desired to perform a slightly different type of circular dithering, indicated by type equaling "CIRCLE2" A at step 2102, DITHER_SHOTS 2100 proceeds to step 2108, where it dithers in a modified circular spiral. The routine for accomplishing this is the procedure "DO_DITHER_CIRCULAR2" shown in Appendix B at lines 183 through 279. This procedure works in a similar manner to that of the program of Appendix A illustrated in FIG. 27.

If it is desired to perform a line-by-line oriented dithering, indicated by type equalling "LINE" at step 2102, DITHER_SHOTS 2100 proceeds to step 2110, where a routine is called that dithers line by line. This routine is shown as procedure "DO_DITHER_XY" at lines 283 through 395 of the attached Appendix B.

If an alternative form of dithering is desired, as indicated by type equalling "DITHERC" at step 2102, DITHER_SHOTS 2100 proceeds to step 2112, where this alternative method is used. This is found as the procedure "DO_DITHER_C" in Appendix B at lines 399 through 515.

Using a variety of shot dithering methods, an array of shots is created for a fixed spot size spread over a treatment area to correct to the desired degree of ablation.

DITHER_SHOTS 2100 then proceeds to step 2114, where it determines whether a sorting of the shots is desired. If not, DITHER_SHOTS 2100 proceeds to step 2116, where it returns to the software controlling the excimer laser system with a shot array suitable for correcting to the desired degree. If at step 2114 sorting is desired, DITHER_SHOTS 2100 instead proceeds to step 2116, where it determines whether random sorting is desired.

Random sorting will statistically decrease overall heating during the treatment. Although there will typically be some overlap from shot to shot, statistically, different portions of the treatment area will be ablated within a given period of time, rather than one portion of the treatment area being continuously ablated. If at step 2116 it is desired to randomly sort, control proceeds to step 2118, where DITHER_SHOTS 2100 randomly sorts the shots. This is performed by the program attached as Appendix C at lines 40–52.

If at step 2116 it is desired to not randomly sort, but instead to sort for maximum displacement between shots, control proceeds to step 2120, where DITHER_SHOT 2100 sorts into a spiral pattern, as illustrated in the attached Appendix C by the procedure "SORT_SPIRAL", shown at lines 21–38. From steps 2120 and 2118, control then returns to a calling procedure in the excimer laser system at step 2116.

In this way, a shot dither treatment is achieved, and the shots are sorted in a way to minimize thermal heating. It will be appreciated that the sorting could be provided also with the software illustrated in FIG. 27 and attached as Appendix A.

The foregoing disclosure and description of the invention are illustrative and explanatory thereof, and various changes in the size, shape, materials, components, circuit elements, and optical components, as well as in the details of the illustrated system and construction and method of operation may be made without departing from the spirit of the invention.

```
{

Helix         version 1.0   Mai   1994           (C)  CHIRON Technolas

Unit Helix

Versucht einen Behandlungsvektor für Myopiebehandlung in Helixform zu
    erstellen.

}

UNIT Helix;

{$O+,G+}

INTERFACE

USES Overlay, Crt, GlobVar, Fenster;

CONST
    VarSpot       =   0;
    ConstSpot     = 128;
VAR
    SpiralMaxZone : double;

FUNCTION HelixErrorMsg(Error : INTEGER): STRING;

PROCEDURE CalcHelix(VAR Korr, Zone, MaxAbtrag : double; VAR Error : INTEGER);

PROCEDURE Search(Typ : BYTE; VAR Error : INTEGER);

IMPLEMENTATION

CONST
    LIASize       = 1023;
    Micro         = 4096;
    HalfZone      = 0.0075;   { Ein µm Ablation entspricht 4096 Digits }
TYPE                          { Radius der betrachteten Zone          }
    LongIntArray  = ARRAY[0..LIASize] OF LongInt;
    LongIntArrPtr = ^LongIntArray;
    RingType      = RECORD
                        Count : INTEGER;  { Anzahl Schüsse auf'm Ring   }
                        Spot  : INTEGER;  { Durchmesser in µm           }
                        Dist  : INTEGER;  { Entfernung von Mitte in µm  }
                    END;
VAR
    PReferenz     : LongIntArrPtr;
    MaxAbl        : LongInt;
    MaxSpot       : double;
    ShotCount     : WORD;
    VolTheo       : double;
    Ring          : ARRAY[0..31] OF RingType;
    AblShot       : double;

{-------------------------------------------------------------------}
{ Berechnung einer Myopiebehandlung                                 }
{ Übergabe: Korr in dioptr, Zone in m                               }
{ Calculation with an empirically found formula for Myopia-treatment}
```

APPENDIX A

U.S. EXPRESS MAIL NO. TB693235642US

```
71   { using helixes with varable spotsizes.                              }
72   {----------------------------------------------------------------}
73   PROCEDURE CalcHelix(VAR Korr, Zone, MaxAbtrag : double; VAR Error : INTEGER);
74   CONST
75     Ralt   = 0.0078;
76   VAR
77     Abl,
78     Rneu   : double;
79     Ringe  : INTEGER;
80     Spot,
81     Radius : double;
82     Loop   : INTEGER;
83     P1, P2 : double;
84     PRing  : double;
85     d      : double;
86     Win    : double;
87     dWin   : double;
88     WinSt  : INTEGER;
89
90         {
91
92
93
94         FUNCTION NeuR(Korr : double) : double;                          }
95         BEGIN
96           NeuR := (1.3377-1) / ( (1.3377-1)/Ralt + Korr );
97         END; {NeuR}
98
99         {
100
101
102
103        FUNCTION MaxAbl(Korr, Zone : double) : double;                  }
104        VAR
105          QRad  : double;
106          RNeu  : double;
107        BEGIN
108          RNeu   := NeuR(Korr);
109          QRad   := Sqr(Zone / 2.0);
110          MaxAbl := Ralt - Sqrt(Ralt*Ralt-QRad) - RNeu + Sqrt(RNeu*RNeu-QRad);
111        END; {MaxAbl}
112
113
114        {
115
116
117
118        FUNCTION GetZone(Korr, MaxAbl : double) : double;               }
119        VAR
120          RNeu : double;
121          d    : double;
122        BEGIN
123          RNeu    := NeuR(Korr);
124          d       := -2*MaxAbl*Ralt + 4*Rneu*(MaxAbl - Ralt + RNeu) + MaxAbl*MaxAbl;
125          d       := Sqrt(d) / (MaxAbl - Ralt + RNeu);
126          GetZone := Sqrt(MaxAbl) * Sqrt(-MaxAbl + 2*Ralt) * d;
127        END; {GetZone}
128
129
130        {
131
132
133
134        FUNCTION Pot(z, h : double) : double;                           }
135        BEGIN
136          IF z > 0
137            THEN Pot := Exp( h * Ln(z) )
138            ELSE Pot := 0.0;
139        END; {Pot}
140
```

APPENDIX A

U.S. EXPRESS MAIL NO. TB693235642US

U.S. EXPRESS MAIL NO. TB693235642US

U.S. EXPRESS MAIL NO. TB693235642US

61

```
142
143              {
144
145                                                                                                      }
146              {------ Addiert einen Ring mit 8 Schüssen ------}
147              PROCEDURE AddRing(Radius, Spot, Winkel : double);
148              VAR
149                Loop  : INTEGER;
150              BEGIN
151                FOR Loop := 1 TO 8 DO
152                  IF Dat_All.VektorLaenge <= MaxVektor THEN
153                    BEGIN
154                      INC(Dat_All.Vektorlaenge);
155                      WITH Treatment[Dat_All.Vektorlaenge]^ DO
156                        BEGIN
157                          x_pos := Round(Radius*1E6*Cos(Winkel));
158                          y_pos := Round(Radius*1E6*Sin(Winkel));
159                          Winkel:= Winkel + Pi/4.0;
160                          sollblende := Round(Spot*1E6);
161                          istblende := sollblende;
162                          energie := 100;
163                        END;
164                    END
165                  ELSE Error := 2;
166              END; {AddRing}
167
168
169              {
170                  Existiert gemeinsamer Teiler für »a« und »b«?
171                                                                                                      }
172              FUNCTION GT(a, b : INTEGER) : BOOLEAN;
173              VAR
174                i : INTEGER;
175              BEGIN
176                IF a > b THEN
177                  BEGIN
178                    i := a; a := b; b := i;
179                  END;
180                GT := FALSE;
181                FOR i := 2 TO (a DIV 2) DO
182                  IF ((a MOD i)=0) AND ((b MOD i)=0) THEN GT := TRUE;
183              END; {GT}
184
185
186      BEGIN
187        Error := 1;
188        IF Zone < 0.0029999 THEN EXIT;
189        IF Zone > 0.0070001 THEN EXIT;
190        Abl      := MaxAbl(Korr, Zone);
191        Ringe := (Trunc(Abl / (8*0.25E-6)) + 1);
192        Abl      := Ringe * 8 * 0.25E-6;
193        MaxAbtrag := Abl;
194        Zone     := GetZone(Korr, Abl);
195
196        DEC(Ringe);
197        PRing := Pot(Ringe, 1.5) * 2.0;
198
199        {---------------------- Empirisch bestimmte Parameter ----------------}
200        d    := Zone*1000;
201        P1   := 6.9  - (7.0-d)*0.08;
202        P2   := 0.95 - Pot((7.0-d), 1.25) * 0.08;
203        P2   := P2 / 1000.0;
204
205        Win   := 0;
206        dWin  := (Pi/4.0) / Ringe;
207        Error := 0;
208        WinSt := Ringe DIV 3 - Ringe DIV 12;
209        IF WinSt < 1 THEN WinSt := 1;
210        WHILE GT(WinSt, Ringe) DO
```

APPENDIX A

U.S. EXPRESS MAIL NO. TB693235642US

```
211      INC(WinSt);
212      FOR Loop := 0 TO Ringe DO
213      BEGIN
214         Radius := Zone / 20.0 +  (Zone*(Loop+1)) / (P1*(Ringe+1));
215         Spot   := ((Zone-P2) / 2.0  -  Pot(Loop, 1.5) * (Zone/2.0 - P2) / PRing) * 2.0
                   ;
216         {
217         Win    := Loop * (Pi/4.0) / Ringe;
218         }
219
220         AddRing(Radius, Spot, Win);
221         Win := Win + WinSt * dWin;
222         IF Win > (2.0*Pi) THEN
223            Win := Win - 2.0*Pi;
224      END;
225   END; {CalcHelix}
226
227
228
229   {
230
231   Funktion    Because it takes time to find the correct solution it's better to
232               give some messages time by time.
233   Eingabe
234   Rückgabe
235      .                                                                              }
236   PROCEDURE StillAlive;
237   CONST
238      c : ARRAY[0..3] OF CHAR = (' ','\','|','/');
239   VAR
240      X, Y  : INTEGER;
241      i     : INTEGER;
242   BEGIN
243      X := WhereX;
244      Y := WhereY;
245      i := (SysTick DIV 4) AND $00000003;
246      Write(c[i]);
247      IF i = 0 THEN
248         BEGIN
249            i := TextAttr;
250            TextColor(DarkGray);
251            GotoXY(X-4, Y+1);
252            Write(Now);
253            TextAttr := i AND $00FF;
254         END;
255      GotoXY(X, Y);
256   END; {StillAlive}
257
258
259   {
260
261   Funktion    Adds a "Myopia" or "Hyperopia" of »Dio« diopters
262               to the PReference-Array.
263   Eingabe
264   Rückgabe
265                                                                                     }
266   PROCEDURE AddDioptr(Dio : double; Spot : double);
267   VAR
268      R1, R2      : double;
269      R1Q,R2Q     : double;
270      Schwelle    : double;
271      d, dQ       : double;
272      X, Y        : INTEGER;
273      w, l        : LongInt;
274      SpotQ       : double;
275      LoopEnd     : INTEGER;
276      SpotH2      : double;
277   BEGIN
278      Dio := -Dio;
279      R1    := (SysData.index-1) / ((SysData.Index-1)/SysData.r_alt - Dio);
```

APPENDIX A

U.S. EXPRESS MAIL NO. TB693235642US

```
280     Spot    := Spot / 2.0;
281     IF R1 < Spot THEN EXIT;
282
283     R2  := SysData.R_alt;
284     R2Q := R2*R2;
285
286     MaxAbl   := -200000;
287     SpotQ    := Spot*Spot;
288     R1Q      := R1*R1;
289     VolTheo  := VolTheo +
290                 Pi/3.0 * ((2.0*R2Q*R2 - (2*R2Q+SpotQ)*Sqrt(R2Q-SpotQ)));
291     VolTheo  := VolTheo -
292                 Pi/3.0 * ((2.0*R1Q*R1 - (2*R1Q+SpotQ)*Sqrt(R1Q-SpotQ)));
293     Schwelle := + (R2 - Sqrt(R2Q - SpotQ)) - (R1 - Sqrt(R1Q - SpotQ)) ;
294     LoopEnd  := Round(Spot * (LIASize / HalfZone));
295     IF LoopEnd > LIASize THEN LoopEnd := LIASize;
296     FOR X := 0 TO LoopEnd DO
297        BEGIN
298           dQ := X * Sqr(HalfZone/LIASize) * X;    {Radiusquadrat }
299           IF dQ < SpotQ THEN
300              BEGIN
301                 d :=  Schwelle + (R1 - Sqrt(R1Q - dQ + 1.0E-12)) - (R2 - Sqrt(R2Q - dQ + 1
                       .0E-12)) ;
302                 d := d * 1.0E6 * Micro;
303                 IF d < (Maxlongint DIV 2) THEN l := Round(d)
304                                           ELSE l := Maxlongint DIV 2;
305                 IF dio < 0
306                    THEN INC(PReferenz^[X], l - PReferenz^[0])
307                    ELSE INC(PReferenz^[X], l);      {nach oben spiegeln }
308                 IF PReferenz^[X] > MaxAbl THEN MaxAbl := PReferenz^[X];
309              END;
310        END;
311  END; {AddDioptr}
312
313
314  {
315
316  Funktion   Fills the Array PReference with the aim of the treatment.
317
318  Eingabe
319  Rückgabe
320                                                                                       }
321  PROCEDURE FillReferenz(VAR Error : INTEGER);
322  VAR
323     Loop    : INTEGER;
324     LastDio : double;
325     Zone    : double;
326     R1, Spot: double;
327  BEGIN
328     IF MaxAvail < SizeOf(LongIntArray) THEN
329        BEGIN
330           Error := 180;
331           EXIT;
332        END;
333     New(PReferenz);
334     MaxSpot := 0;
335     FillChar(PReferenz^, SizeOf(LongintArray), 0);
336     MaxAbl := 0;
337     IF Dat_All.sph_korr > 1E-12 THEN
338        BEGIN
339           Zone := (SysData.index-1) / ((SysData.Index-1)/SysData.r_alt + Dat_all.sph_kor
                   r) - 0.001E-3;
340           IF Zone > 7.0E-3 THEN Zone := 7.0E-3;
341           Zone := Zone*2.0;
342           AddDioptr(Dat_all.sph_korr, Zone);
343           MaxSpot := Dat_all.rhomax*2;
344           MaxAbl  := PReferenz^[Round(Dat_All.rhomax*LIASize/HalfZone)];
345           FOR Loop := 10 TO LIASize DO
346              IF PReferenz^[Loop]<1 THEN PReferenz^[Loop] := PReferenz^[Loop-1];
347           EXIT;
```

APPENDIX A

U.S. EXPRESS MAIL TB693235642US

```
                                                                64
348         END;
349     IF SysData.CanadianMode THEN
350       BEGIN
351         IF Dat_All.Canadian.Calculated THEN
352           FOR Loop := 1 TO 8 DO
353             WITH Dat_All.Canadian.Data[Loop] DO
354               IF Percent > 0.00001 THEN
355                 BEGIN
356                   AddDioptr(korr, 2.0*rhomax);
357                   IF MaxSpot < rhomax*2 THEN
358                     MaxSpot := rhomax*2;
359                 END;
360         EXIT;
361       END;
362     IF (Dat_All.TransTable.Eintraege > 0) AND (Dat_All.TransTable.Eintraege < 255) THE
        N
363       BEGIN
364         LastDio := 0;
365         WITH Dat_All.TransTable DO
366           FOR Loop := Eintraege DOWNTO 1 DO
367             BEGIN
368               Adddioptr(TransEvent[Loop].Dioptr-LastDio, TransEvent[Loop].Max);
369               LastDio := TransEvent[Loop].Dioptr;
370               IF MaxSpot < TransEvent[Loop].Max THEN
371                 MaxSpot := TransEvent[Loop].Max;
372             END;
373         AddDioptr(Dat_All.sph_korr-LastDio, Dat_All.rhomax*2);
374         EXIT;
375       END;
376     MaxSpot := Dat_all.rhomax*2;
377     AddDioptr(Dat_All.sph_korr, Dat_All.rhomax*2);
378 END; {FillReferenz}
379
380
381 {
382
383 Funktion     Clears memory.
384
385 Eingabe
386 Rückgabe
387                                                                                          }
388 PROCEDURE DestroyReferenz;
389 BEGIN
390   Dispose(PReferenz);
391 END; {DestroyReferenz}
392
393
394 {
395
396 Funktion     Partitioning of the spirals into (max. 32) rings with 8,16,32...
397              shots. This makes calculation easier.
398 Eingabe
399 Rückgabe
400                                                                                          }
401 PROCEDURE Verteilen(Shots : WORD);
402 CONST
403   V            : ARRAY[1..8] OF WORD = (8, 16, 32, 64, 128, 256, 512, 1024);
404 VAR
405   ShotCnt      : ARRAY[0..7] OF WORD;
406   Loop, i, j   : INTEGER;
407
408         {
409            Berechnung der Summe der in »ShotCnt[]« beschriebenen Schüsse.
410                                                                                          }
411         FUNCTION Summe : WORD;
412         VAR
413           Loop : INTEGER;
414           S    : WORD;
415         BEGIN
416           S := 0;
```

APPENDIX A

U.S. EXPRESS MAIL NO. TB693235642US

```
417            FOR Loop := 1 TO 7 DO
418              S := S + ShotCnt[Loop];
419            Summe := S;
420          END;
421
422    BEGIN
423      IF Dat_All.sph_korr > 1E-12 THEN
424        BEGIN
425          i := 8;
426          j := 4;
427          Loop := 0;
428          REPEAT
429            REPEAT
430              Ring[Loop].Count := i;
431              INC(Loop);
432              DEC(j);
433            UNTIL j = 0;
434            IF i < 128 THEN i := i*2;
435            j := 4;
436            IF i > 16 THEN j   := 5;
437            IF i > 64 THEN j   := 1;
438            IF Loop = 31 THEN i := 256;
439          UNTIL Loop > 31;
440          EXIT;
441        END;
442      FillChar(ShotCnt, SizeOf(ShotCnt), 0);
443      ShotCnt[0] := Shots MOD 8;
444      ShotCnt[1] := Shots DIV 8;
445      FOR Loop := 1 TO 6 DO
446        IF Summe > 31 THEN
447          WHILE (ShotCnt[Loop] > 4) AND (Summe > 31) DO
448            BEGIN
449              DEC(ShotCnt[Loop], 2);
450              INC(ShotCnt[Loop+1], 1);
451            END;
452      j := 0;
453      FOR Loop := 1 TO 7 DO
454        FOR i := 1 TO ShotCnt[Loop] DO
455          BEGIN
456            Ring[j].Count := V[Loop];
457            INC(j);
458          END;
459      INC(Ring[j].Count, ShotCnt[0]);
460      FOR Loop := j+1 TO 31 DO
461        Ring[Loop].Count := 0;
462    END; {Verteilen}
463
464
465    {
466
467    Funktion    Checking routine for programming purposes.
468
469    Eingabe
470    Rückgabe
471                                                                                        }
472    PROCEDURE FastView(PA : LongIntArrPtr);
473    VAR
474      Loop   : INTEGER;
475      Max    : LongInt;
476      y1,y2  : LongInt;
477
478        PROCEDURE VertLine(X, Y : INTEGER);
479        BEGIN
480          GotoXY(X, 1);
481          WHILE Y > 1 DO
482            BEGIN
483              Write(' ');
484              GotoXY(X, WhereY+1);
485              DEC(Y, 2);
486            END;
```

APPENDIX A

U.S. EXPRESS MAIL NO. TB693235642US

```
487            IF Y > 0 THEN Write(' ');
488         END;
489
490   BEGIN
491      TextBackground(LightGray);
492      ClrScr;
493      Max := PA^[0];
494      FOR Loop := 1 TO LIASize DO
495         IF Max < PA^[Loop] THEN Max := PA^[Loop];
496      FOR Loop := 1 TO LIASize DO
497         IF Max < PReferenz^[Loop] THEN Max := PReferenz^[Loop];
498      GotoXY(1, 25);
499      IF Max=0 THEN EXIT;
500      FOR Loop := 0 TO 79 DO
501         BEGIN
502            y1 := Round(PA^[Trunc(Loop/79.0*LIASize)]*48.0/Max);
503            y2 := Round(PReferenz^[Trunc(Loop/79.0*LIASize)]*48.0/Max);
504            IF Y1 > Y2 THEN
505               BEGIN
506                  TextColor(Black); TextBackground(LightGray);
507                  Vertline(1+Loop, y1);
508                  TextColor(Red); TextBackground(Black);
509                  Vertline(1+Loop, y2);
510               END
511            ELSE BEGIN
512                  TextColor(Red); TextBackground(LightGray);
513                  Vertline(1+Loop, y2);
514                  TextColor(Black); TextBackground(Red);
515                  Vertline(1+Loop, y1);
516               END;
517         END;
518      GotoXY(1, 25);
519   END; {FastView}
520
521
522
523   {
524
525   Funktion    Gives each ring of shots a special spotsize for the shots.
526
527   Eingabe
528   Rückgabe
529                                                                            }
530   PROCEDURE BlendenVorbelegung(Typ : BYTE);
531   VAR
532      Loop : INTEGER;
533      l    : LongInt;
534      Mini : LongInt;
535   BEGIN
536      IF Dat_all.sph_korr > 1E-12 THEN
537         BEGIN
538            IF ((Typ AND ConstSpot) = ConstSpot) OR (1=1) THEN
539               BEGIN
540                  Mini := Round(Dat_all.rhomax*1E6);
541                  IF Mini < 2000 THEN Mini := 2000;
542                  IF Mini > 3500 THEN Mini := 3500;
543                  FOR Loop := 0 TO 31 DO
544                     Ring[Loop].Spot := Mini;      { Nur wie Radius! }
545               END
546            ELSE BEGIN
547                  FOR Loop := 0 TO 31 DO
548                     Ring[Loop].Spot := Round(Dat_All.rhomax*2E6);
549               END;
550         END
551      ELSE BEGIN
552         IF (Typ AND ConstSpot) = ConstSpot THEN
553            BEGIN
554               l := Round(Sqrt(VolTheo*1.135/(ShotCount*SysData.rate*Pi)) * 2E6);
555               FOR Loop := 0 TO 31 DO
556                  Ring[Loop].Spot := l;
```

APPENDIX A

U.S. EXPRESS MAIL NO. TB693235642US

```
557          END
558        ELSE BEGIN
559          FOR Loop := 0 TO 31 DO
560            Ring[Loop].Spot := Round(MaxSpot*1E6);
561        END;
562    END;
563  END; {BlendenVorbelegung}
564
565
566  {
567
568    Funktion    Calculate ablation of one of the shot-rings and store it in
569                PAblation.
570    Eingabe
571    Rückgabe
572                                                                              }
573  PROCEDURE Calculate(RingNr : INTEGER; VAR PAblation : LongIntArrPtr);
574  VAR
575    Loop   : LongInt;
576    w      : double;
577    Q      : double;
578    Entf   : double;
579    s      : STRING;
580    EMax,
581    EMin   : double;
582    e      : double;
583    Ra, Di : double;
584    l      : LongInt;
585    c      : double;
586
587          {
588
589
590                                                                              }
591          FUNCTION Arccos(w : double) : double;
592          BEGIN
593            IF Abs(w) <> 1
594              THEN ArcCos := Pi/2.0 - ArcTan(w / Sqrt(1.0 - w*w))
595              ELSE ArcCos := Pi/2.0 * (1.0 - w);
596          END; {ArcCos}
597
598  BEGIN
599    WITH Ring[RingNr] DO
600      BEGIN
601        l := Round(LongInt(Count)*AblShot);
602        Ra := Spot*1E-6*LIASize/HalfZone/2.0;
603        Di := Dist*1E-6*LIASize/HalfZone;
604        IF (Spot=0) OR (Count=0) THEN
605          BEGIN
606            FillChar(PAblation^, SizeOf(LongIntArray), 0);
607            EXIT;
608          END;
609        IF Dist = 0 THEN
610          BEGIN
611            FillChar(PAblation^, SizeOf(LongIntArray), 0);
612            FOR Loop := 0 TO Round(Ra) DO
613              PAblation^[Loop] := l;
614            EXIT;
615          END;
616
617        Di := Di * HalfZone / LIASize;
618        Ra := Ra * HalfZone / LIASize;
619        Q := (Di*Di - Ra*Ra);
620        EMax := (Di + Ra);
621        EMin := Abs(Di - Ra);
622        c := Count / Pi;
623        FOR Loop := 0 TO LIASize DO
624          BEGIN
625            Entf := Loop * HalfZone / LIASize;
626            IF Entf=0 THEN Entf := 1E-12;
```

APPENDIX A

U.S. EXPRESS MAIL NO. TB693235642US

```
627              IF (Entf >= EMin) AND (Entf <= EMax) THEN
628                BEGIN
629                  e := (c * Arccos( (Q + (Entf*Entf)) / (2.0*Entf*Di)));
630                  PAblation^[Loop] := Round(e*AblShot);
631                END
632              ELSE IF (Entf < EMin) AND (Spot/2.0 > Dist)
633                THEN PAblation^[Loop] := 1
634                ELSE PAblation^[Loop] := 0;
635          END;
636      END; {with}
637  END; {Calculate}
638
639
640
641  {
642
643    Funktion   Search for rings of 8,16,32.. shots to build the spirals.
644               The sum of the ablation of all shot-rings (stored in "PAblation")
645               has to be the same as the theor. values stored in "PReference").
646    Eingabe    Typ: Use constant spots or allow variable spot sizes.
647    Rückgabe
648                                                                                }
649  PROCEDURE SearchRings(Typ : BYTE; VAR Error : INTEGER);
650  VAR
651    Loop          : INTEGER;
652    Step          : INTEGER;
653    PAblation     : LongIntArrPtr;
654    PRingAblation : LongIntArrPtr;
655    PSum          : LongIntArrPtr;
656    Ready         : BOOLEAN;
657    i, j          : INTEGER;
658    Grenze        : INTEGER;
659
660      {
661         Addiert »PRingAblation^« zu »PAblation^«.
662                                                                                }
663      PROCEDURE AddAblation;
664      VAR
665        Loop : INTEGER;
666      BEGIN
667        FOR Loop := 0 TO LIASize DO
668          INC(PAblation^[Loop], PRingAblation^[Loop]);
669      END; {SearchRings.AddAblation}
670
671
672      {
673         Subtrahiert »PRingAblation^« von »PAblation^«.
674                                                                                }
675      PROCEDURE DecAblation;
676      VAR
677        Loop : INTEGER;
678      BEGIN
679        FOR Loop := 0 TO LIASize DO
680          DEC(PAblation^[Loop], PRingAblation^[Loop]);
681      END; {SearchRings.DecAblation}
682
683
684      {
685         "TRUE", falls »PAblation^« an irgendeiner Stelle kleiner ist
686         als »PReferenz^«. (d.h.: Abtrag ist an dieser Stelle zu gering.)
687                                                                                }
688      FUNCTION XBelowCheck(Grenze:INTEGER) : BOOLEAN;
689      VAR
690        Loop : INTEGER;
691      BEGIN
692        XBelowCheck := FALSE;
693        FOR Loop := 1 TO Grenze DO
694          IF (PAblation^[Loop] < PReferenz^[Loop]-(Micro SHR 4)) THEN
695            BEGIN
696              XBelowCheck := TRUE;
```

```
697              EXIT;
698            END;
699        END; {SearchRings.XBelowCheck}
700
701
702
703        {
704           "TRUE", falls »PAblation^« an irgendeiner Stelle kleiner ist
705           als »PReferenz^«. (d.h.: Abtrag ist an dieser Stelle zu gering.)
706                                                                              }
707        FUNCTION BelowCheck : BOOLEAN;
708        BEGIN
709           BelowCheck := XBelowCheck(LIASize);
710        END; {SearchRings.BelowCheck}
711
712
713        {
714           "TRUE", falls »PAblation^« an irgendeiner Stelle größer ist
715           als »PReferenz^«. (d.h.: An d. Stelle wird zuviel abgetragen.)
716                                                                              }
717        FUNCTION AboveCheck : BOOLEAN;
718        VAR
719           Loop : INTEGER;
720        BEGIN
721           AboveCheck := FALSE;
722           FOR Loop := 1 TO LIASize DO
723              IF (PAblation^[Loop] > PReferenz^[Loop]+(Micro SHR 4)) THEN
724                 BEGIN
725                    AboveCheck := TRUE;
726                    EXIT;
727                 END;
728        END; {SearchRings.AboveCheck}
729
730
731        {
732           Bestimmt größten Abtrag laut »PAblation^«.
733                                                                              }
734        FUNCTION MaximalAblation : LongInt;
735        VAR
736           Loop : INTEGER;
737           l    : LongInt;
738        BEGIN
739           l := PAblation^[0];
740           FOR Loop := 1 TO LIASize DO
741              IF (PAblation^[Loop]) > l THEN
742                 l := PAblation^[Loop];
743           MaximalAblation := l;
744        END; {SearchRings.MaximalAblation}
745
746   BEGIN
747     StillAlive;
748     New(PAblation);
749     New(PRingAblation);
750     New(PSum);
751     FillChar(PAblation^, SizeOf(LongIntArray), 0);
752     FillChar(PSum^, SizeOf(LongIntArray), 0);
753     Ready := FALSE;
754     {
755     FastView(PReferenz);
756     }
757     IF Dat_All.sph_korr > 1E-12 THEN
758        BEGIN
759           FOR Loop := 0 TO 31 DO
760              Ring[Loop].Dist := 6000;
761           IF (Typ AND ConstSpot) = ConstSpot THEN    {==== Hyperopia const. spots====}
762              BEGIN
763                 FOR Loop := 0 TO 31 DO
764                    IF Ring[Loop].Count > 0 THEN
765                       BEGIN
766                          Step := 8*8*8*8;
```

APPENDIX A

U.S. EXPRESS MAIL NO. TB693235642US

```
767              REPEAT
768                Ready := FALSE;
769                REPEAT
770                  StillAlive;
771                  DEC(Ring[Loop].Dist, Step);
772                  Calculate(Loop, PRingAblation);
773                  AddAblation;
774                  {
775                  FastView(PAblation);
776                  writeln('Ring:',Loop,'    Dist:',Ring[Loop].Dist);
777                  }
778                  Ready := AboveCheck;
779                  DecAblation;
780                  IF Ring[Loop].Dist < Step THEN
781                    Ready := TRUE;
782                UNTIL Ready;
783                INC(Ring[Loop].Dist, Step);
784                Step := Step SHR 3;
785              UNTIL Step < 1;
786              Calculate(Loop, PRingAblation);
787              AddAblation;
788              IF MaximalAblation > MaxAbl THEN
789                BEGIN
790                  IF Loop < 31 THEN
791                    FOR i := Loop+1 TO 31 DO
792                      Ring[i].Count := 0;
793                END;
794            END;
795          END
796          ELSE BEGIN                                   {==== Hyperopia variabl. spots=}
797            FOR Loop := 0 TO 31 DO
798              IF Ring[Loop].Count > 0 THEN
799                FOR j := 0 TO 1 DO
800                  BEGIN
801                    Step := 8*8*8*8;
802                    REPEAT
803                      Ready := FALSE;
804                      REPEAT
805                        StillAlive;
806                        DEC(Ring[Loop].Dist, Step);
807                        Calculate(Loop, PRingAblation);
808                        AddAblation;
809                        {
810                        FastView(PAblation);
811                        write('Ring:',Loop,'    Dist:',Ring[Loop].Dist);
812                        }
813                        Ready := AboveCheck;
814                        DecAblation;
815                        IF Ring[Loop].Dist < Step THEN
816                          Ready := TRUE;
817                      UNTIL Ready;
818                      INC(Ring[Loop].Dist, Step);
819                      Step := Step SHR 3;
820                    UNTIL Step < 1;
821                    IF j = 1 THEN
822                      BEGIN
823                        Calculate(Loop, PRingAblation);
824                        AddAblation;
825                      END
826                    ELSE BEGIN
827                      Ring[Loop].Spot := Round(Dat_all.rhomax*1.5E6) -
828                                          (Ring[Loop].Dist-Ring[Loop].Spot DIV 2);
829                      IF Ring[Loop].Spot < 2000 THEN
830                        Ring[Loop].Spot := 2000;
831                      Ring[Loop].Dist := 6000;
832                    END;
833                    IF MaximalAblation > MaxAbl THEN
834                      BEGIN
835                        IF j = 1 THEN
836                          IF Loop < 31 THEN
```

APPENDIX A
U.S. EXPRESS MAIL NO. TB693235642US

```
                                    71
837                         FOR i := Loop+1 TO 31 DO
838                             Ring[i].Count := 0;
839                   END;
840             END;
841        END;
842        IF MaximalAblation < MaxAbl
843          THEN Error := 181
844          ELSE BEGIN         {----- Hyperopie korrigieren auf richtigen Abtrag -----}
845            Loop := 31;
846            WHILE (Ring[Loop].Count < 1) AND (Loop > 0) DO
847              DEC(Loop);
848            IF Ring[Loop].Count > 64 THEN
849              BEGIN
850                WHILE (MaxAbl > MaximalAblation) AND (Ring[Loop].Count >= 80)
851                  DO BEGIN
852                    StillAlive;
853                    Calculate(Loop, PRingAblation);
854                    DecAblation;
855                    DEC(Ring[Loop].Count, 16);
856                    Calculate(Loop, PRingAblation);
857                    AddAblation;
858                  END;
859              END;
860          END;
861     END
862     ELSE BEGIN
863       IF (Typ AND ConstSpot) = ConstSpot THEN    {==== Myopia with const. spots======}
864         BEGIN
865           Grenze := Round(Ring[0].Spot/2.0E6*LIASize/HalfZone-3);
866           FOR Loop := 0 TO 31 DO
867             BEGIN
868               IF Ring[Loop].Count > 0 THEN
869                 BEGIN
870                   Ring[Loop].Dist := 0;
871                   Calculate(Loop, PRingAblation);
872                   AddAblation;
873                 END;
874             END;
875           FillChar(PRingAblation^, SizeOf(LongIntArray), 0);
876           FOR Loop := 0 TO 31 DO
877             IF Ring[Loop].Count > 0 THEN
878               BEGIN
879                 Calculate(Loop, PRingAblation);
880                 DecAblation;
881                 Ring[Loop].Dist := 0;
882                 Step := 8*8*8*8;
883                 REPEAT
884                   Ready := FALSE;
885                   REPEAT
886                     StillAlive;
887                     INC(Ring[Loop].Dist, Step);
888                     Calculate(Loop, PRingAblation);
889                     AddAblation;
890                     {
891                     FastView(PAblation);
892                     write('Ring:',Loop:5,'   Dist:',Ring[Loop].Dist:5,
893                           '  Spot:',Ring[Loop].Spot:5,'    ',Grenze);
894                     }
895                     Ready := XBelowCheck(Grenze);
896                     DecAblation;
897                     IF Ring[Loop].Dist > 8700 THEN
898                       Ready := TRUE;
899                   UNTIL Ready;
900                   DEC(Ring[Loop].Dist, Step);
901                   Step := Step SHR 3;
902                 UNTIL Step < 1;
903                 Calculate(Loop, PRingAblation);
904                 AddAblation;
905               END;
```

APPENDIX A

```
906        END
907        ELSE BEGIN                               {==== Myopia mit variabl. spots ====}
908          FOR Loop := 0 TO 31 DO
909            BEGIN
910              IF Ring[Loop].Count > 0 THEN
911                BEGIN
912                  Ring[Loop].Dist := 0;
913                  Calculate(Loop, PRingAblation);
914                  AddAblation;
915                END;
916            END;
917          FillChar(PRingAblation^, SizeOf(LongIntArray), 0);
918          FOR Loop := 0 TO 31 DO
919            IF Ring[Loop].Count > 0 THEN
920              BEGIN
921                FOR j := 0 TO LIASize DO
922                  INC(PSum^[j], PRingAblation^[j]);
923                Calculate(Loop, PRingAblation);
924                DecAblation;
925                Ring[Loop].Spot := 0;
926                FOR j := LIASize DOWNTO 0 DO
927                  IF (Ring[Loop].Spot=0) AND (PReferenz^[j] > PSum^[j]) THEN
928                    BEGIN
929                      Ring[Loop].Spot := 1 + Trunc(j * HalfZone*2E6 / LIASize+0.99);
930                      Grenze := j;
931                    END;
932                DEC(Grenze, 4);
933                Ring[Loop].Dist := 0;
934                Step := 8*8*8*8;
935                WHILE Step*2 > Ring[Loop].Spot DO
936                  Step := Step SHR 3;
937
938                REPEAT
939                  Ready := FALSE;
940                  REPEAT
941                    StillAlive;
942                    INC(Ring[Loop].Dist, Step);
943                    DEC(Ring[Loop].Spot, Step*2);
944                    Calculate(Loop, PRingAblation);
945                    AddAblation;
946                    {
947                    FastView(PAblation);
948                    write('Ring:',Loop:5,'   Dist:',Ring[Loop].Dist:5,
949                         '  Spot:',Ring[Loop].Spot:5,'   ',Grenze);
950                    }
951                    Ready := XBelowCheck(Grenze);
952                    DecAblation;
953                    IF Ring[Loop].Dist > 8700 THEN
954                      Ready := TRUE;
955                  UNTIL Ready;
956                  DEC(Ring[Loop].Dist, Step);
957                  INC(Ring[Loop].Spot, Step*2);
958                  Step := Step SHR 3;
959                UNTIL Step < 1;
960                Calculate(Loop, PRingAblation);
961                AddAblation;
962              END;
963          END;
964      END;
965      Dispose(PSum);
966      Dispose(PRingAblation);
967      Dispose(PAblation);
968      StillAlive;
969    END; {Search}
970
971
972    {
973
974    Funktion    After determination of the shot-rings these rings have to be
```

APPENDIX A

U.S. EXPRESS MAIL NO. TB693235642US

```
975                    arranged in a way that the shots are ordered in spirals.
976      Eingabe
977      Rückgabe
978                                                                                               }
979      PROCEDURE AddRings2Treatment(VAR Error : INTEGER);
980      VAR
981        Loop  : INTEGER;
982        MLoop : INTEGER;
983        LastWin,
984        Win, d,
985        dWin  : double;
986        WinSt : INTEGER;
987
988            {
989                Existiert gemeinsamer Teiler für »a« und »b«?
990                                                                                               }
991            FUNCTION GT(a, b : INTEGER) : BOOLEAN;
992            VAR
993              i : INTEGER;
994            BEGIN
995              IF a > b THEN
996                 BEGIN
997                    i := a; a := b; b := i;
998                 END;
999              GT := FALSE;
1000             FOR i := 2 TO (a DIV 2) DO
1001               IF ((a MOD i)=0) AND ((b MOD i)=0) THEN GT := TRUE;
1002             IF (b MOD a) = 0 THEN GT := TRUE;
1003           END; {DigitizeRings.GT}
1004
1005
1006           {
1007              Hängt "Schussring" an Schußvektor an.
1008                                                                                               }
1009           PROCEDURE AddRing(Nr : INTEGER; Win : double);
1010           VAR
1011             Loop : INTEGER;
1012             dWin : double;
1013           BEGIN
1014             IF Dat_All.Vektorlaenge + Ring[Nr].Count > max_vektor
1015                THEN EXIT;
1016             dWin := 2.0*Pi / Ring[Nr].Count;
1017             Win := Win * Pi / 180.0;
1018             FOR Loop := 0 TO Ring[Nr].Count-1 DO
1019                BEGIN
1020                  IF Dat_all.Vektorlaenge < max_vektor
1021                     THEN INC(Dat_All.Vektorlaenge)
1022                     ELSE BEGIN
1023                            Error := 181;
1024                            EXIT;
1025                          END;
1026                  WITH Treatment[Dat_all.Vektorlaenge]^ DO
1027                     BEGIN
1028                       x_pos := Round( Sin(Win)*Ring[Nr].Dist);
1029                       y_pos := Round(-Cos(Win)*Ring[Nr].Dist);
1030                       sollblende := Ring[Nr].Spot;
1031                     END;
1032                  Win := Win + dWin;
1033                END;
1034             LastWin := Win;
1035           END; {DigitizeRings.AddRing}
1036
1037     BEGIN
1038       LastWin := 0;
1039       MLoop := -1;
1040       FOR Loop := 0 TO 31 DO
1041         IF Ring[Loop].Count > 0 THEN MLoop := Loop;
1042       IF MLoop < 0 THEN EXIT;
1043       IF MLoop > 3 THEN
1044         BEGIN
```

```
1045          dWin  := (360/8) / (MLoop-3);
1046          WinSt := (MLoop-3) DIV 3  +  (MLoop-3) DIV 17;
1047          IF WinSt<=2 THEN WinSt := 2;
1048          WHILE GT(WinSt, MLoop-3) DO
1049             INC(WinSt);
1050       END;
1051    FOR Loop := 0 TO MLoop DO
1052       BEGIN
1053          IF Ring[Loop].Count > 0 THEN
1054             BEGIN
1055                d := (Ring[Loop].Dist*2 + Ring[Loop].Spot) * 1E-6;
1056                IF SpiralMaxZone < d THEN
1057                   SpiralMaxZone := d;
1058                CASE Loop OF
1059                   0 : Win :=  90.00;
1060                   1 : Win :=  67.50;
1061                   2 : Win :=  56.25;
1062                   3 : Win :=  33.75;
1063                ELSE BEGIN
1064                   IF Loop=4 THEN Win := Win - 22.5;
1065                   d := 360/Ring[Loop].Count;
1066                   Win := Win + WinSt*dWin;
1067                   (*
1068                   LastWin := Win-360/{Ring[Loop-1].Count}8.0+d+(WinSt*dWin);
1069                   *)
1070       .           WHILE Win > LastWin DO
1071                      Win := Win - 45;
1072                   Win := Win + 45;
1073                END;
1074                END; {case}
1075                IF Win > 360 THEN Win := Win-360;
1076                IF Error=0 THEN
1077                   AddRing(Loop, Win);
1078             END;
1079       END;
1080 END; {DigitizeRings}
1081
1082
1083
1084
1085 {
1086
1087  Funktion
1088
1089  Eingabe
1090  Rückgabe
1091
1092 FUNCTION HelixErrorMsg(Error : INTEGER): STRING;
1093 VAR
1094    st : STRING[80];
1095 BEGIN
1096    CASE Error OF
1097       180 : st := Tongue^._No_Mem;
1098       181 : st := 'More than 2500 shots necessary!';
1099       182 : st := 'Correction too small.';
1100       183 : st := 'Correction zone too small';
1101       ELSE st := 'Error creating treatment vector.';
1102    END; {case}
1103    HelixErrorMsg := st;
1104 END; {HelixErrorMsg}
1105
1106
1107 {
1108
1109  Funktion   Main-Procedure for searching the correct spiral-treatment.
1110
1111  Eingabe
1112  Rückgabe
1113
1114 PROCEDURE Search(Typ : BYTE; VAR Error : INTEGER);
```

APPENDIX A

U.S. EXPRESS MAIL NO. TB693235642US

```
1115  VAR
1116     OldRhomax : double;
1117     Taste     : CHAR;
1118  BEGIN
1119     IF Dat_All.rhomax < 1.5E-3 THEN     {---Treatment area large enough?---}
1120        BEGIN
1121           Error := 183;
1122           EXIT;
1123        END;
1124     OldRhomax := Dat_All.rhomax;
1125     SpiralMaxZone := Dat_All.rhomax*2;
1126     IF Dat_All.sph_korr > 6.0 THEN      {------ Erste Abschätzung, ob über 2500 Schuß
                -----}
1127        BEGIN                            { ----- More than 2500 shots? ----}
1128           IF (Dat_all.rhomax*2E6) > (7000-Dat_all.sph_korr*(328.7-7.6*Dat_all.sph_korr))
1129              THEN BEGIN
1130                 Error := 181;
1131                 EXIT;
1132              END;
1133        END;
1134     IF (Dat_all.sph_korr < -0.001) AND (Typ = ConstSpot) THEN
1135        Dat_all.rhomax := Dat_All.rhomax * 100/90;
1136     SpiralMaxZone := Dat_All.rhomax*2;
1137     IF MaxAvail < SizeOf(LongIntArray)*3 + 4096 THEN
1138        BEGIN
1139           Error := 180;
1140           EXIT;
1141        END;
1142     Error    := 0;
1143     VolTheo  := 0.0;
1144     AblShot  := SysData.rate*1.0E6*Micro;
1145     FillReferenz(Error);
1146     Dat_All.rhomax := OldRhomax;
1147     FillChar(Ring, SizeOf(Ring), 0);
1148     ShotCount := Trunc(1.0 + MaxAbl / AblShot);
1149     IF ShotCount > 2500 THEN
1150        BEGIN
1151           DestroyReferenz;
1152           Error := 181;
1153           EXIT;
1154        END;
1155     IF ShotCount < 64 THEN
1156        BEGIN
1157           DestroyReferenz;
1158           Error := 182;
1159           EXIT;
1160        END;
1161     Verteilen(ShotCount);          {--- Create "shot-rings" ----}
1162     BlendenVorbelegung(Typ);       {--- spotsize for the rings--}
1163     SearchRings(Typ, Error);       {---Determine correct distance }
1164                                    {   of the rings from treatment }
1165                                    { center.---                    }
1166     IF Error=0 THEN
1167        AddRings2Treatment(Error);
1168     DestroyReferenz;
1169     IF Error <> 0 THEN Dat_all.Vektorlaenge := 0;
1170     IF Dat_all.sph_korr > 0.000001
1171        THEN Dat_All.MaxAbtrag := 0
1172        ELSE Dat_all.MaxAbtrag := Dat_all.Maxabtrag+
1173                                  (Dat_All.Vektorlaenge-Dat_all.Transversend) * SysData.
                                      rate;
1174     WHILE KeyPressed DO
1175        Taste := ReadKey;
1176  END; {Search}
1177
1178
1179
1180  END
```

APPENDIX A

U.S. EXPRESS MAIL NO. TB693235642US

Procedures for dither mode

```
{----------------------------------------------------------------
 2
 3   The procedures below are part of a large but simple parser
 4   that interprets text like "dither(-5, 2000)" as an instruction
 5   to dither a -5 diptr treatment with spot sizes of 2000µm.
 6   The variable "Fehler" and procedures like "GetNext(..)" and
 7   "CheckEndOfOrder" are based upon this purpose. They are not
 8   relevant to the dither algorithm.
 9
10   A little explanation is needed about how the procedures
11   determine the wished ablation at a given point. There exist
12   a big array (as a matter of fact: 4 big arrays) that contain the
13   wished ablation. To read the ablation at a point (X, Y) one has
14   to refer to (with Mitte=128 is the center of the array on both axis)
15
16   l    := ((longint(Y+Mitte) shl 8 + (X+Mitte))) shl 1;;
17   memW[WArraySeg[l shr 15] : WArrayOfs[l shr 15] + (l and $7FFF)];
18 .
19
20----------------------------------------------------------------}
21
22
23
24
25
26{ Dithering on a rectangular spiral }
27PROCEDURE DoDitherRect(VAR rhomax2 : extended);
28CONST
29   dx     : ARRAY[0..3] OF INTEGER = (0, 1, 0, -1);
30   dy     : ARRAY[0..3] OF INTEGER = (-1, 0, 1, 0);
31VAR
32   Mult   : extended;
33   X, Y   : extended;
34   Stp    : extended;
35   Ec     : extended;
36   iX, iY : INTEGER;
37   e, Cnt : extended;
38   Di,DCnt,
39   ECnt   : WORD;
40BEGIN
41   IF Fehler > 1 THEN EXIT;
42   Stp  := 15.0/255.0;     { mm per digit }
43   Mult := 4.0E9*Stp*Stp / (rhomax2*Pi*rhomax2); { Flächenverhältnis }
44   Mult := Mult*4.0/1000.0  *4;
45   iX   := 0;
46   iY   := 0;
47   SwapEm;
48   Ec   := 0;
49   ECnt := 0;
50   DCnt := 0;
51   Di   := 0;
52   REPEAT
53     X   := iX * Stp + 0.001;
54     Y   := iY * Stp + 0.001;
55     l   := ((LongInt(iY+Mitte) SHL 8 + (iX+Mitte))) SHL 1;
56     Cnt := memW[WArraySeg[l SHR 15] : WArrayOfs[l SHR 15] +
                                                    (l AND $7FFF)];
57     Cnt := Cnt / 64.0 / 4.0;   { SollAbtrag in µm }
58     e   := Cnt * Mult;
59     Cnt := e + Ec;
```

APPENDIX B

U.S. EXPRESS MAIL NO. TB693235642US

```
60      WHILE Cnt > Mult/2 DO
61        BEGIN
62          IF Dat_all.Vektorlaenge < 2500 THEN
63            BEGIN
64              INC(Dat_All.Vektorlaenge);
65              WITH Treatment[Dat_All.Vektorlaenge]^ DO
66                BEGIN
67                  x_pos := Round(X*1000 + ErrorX*1E6);
68                  y_pos := Round(Y*1000 + ErrorY*1E6);
69                  sollblende := Round(rhomax2);
70                  istblende := sollblende;
71                  energie := 100;
72                END;
73            END
74            ELSE BEGIN
75              Fehler := 12;
76              SwapEm;
77              EXIT;
78            END;
79            Cnt := Cnt-4; { -1, wenn odd Anweisung weiter unten noch drin }
80        END;
81        Ec := Cnt;
82        INC(iX, dx[Di]);
83        INC(iY, dy[Di]);
84        INC(DCnt);
85        IF DCnt > (ECnt SHR 1) THEN
86          BEGIN
87            DCnt := 0;
88            INC(ECnt);
89            INC(Di);
90            Di := Di AND $0003;
91          END;
92      UNTIL (Abs(iY) > 126) OR (Abs(iX) > 126);
93END; {DoDitherRect}
94
95
96
97{ Dithering on circles }
98PROCEDURE DoDitherCircular(VAR rhomax2 : extended);
99VAR
100   Mult   : extended;
101   Mult2  : extended;
102   X, Y   : extended;
103   Stp    : extended;
104   Ec     : extended;
105   iX, iY: INTEGER;
106   e, Cnt: extended;
107   Di,DCnt,
108   ECnt   : WORD;
109   i      : INTEGER;
110   StartAngle,
111   StepAngle : extended;
112   InnerRing : extended;
113   Loop   : INTEGER;
114BEGIN
115   IF Fehler > 1 THEN EXIT;
116   Stp  := 15.0/255.0;   { mm per digit }
117   Mult := 4.0E9*Stp*Stp / (rhomax2*Pi*rhomax2); { Flächenverhältnis }
118   Mult := Mult*4.0/1000.0  *4;
119   iX   := 0;
120   iY   := 0;
121   Ec   := 0;
122   ECnt := 0;
123   DCnt := 0;
124   Di   := 0;
125   X    := 0;
```

APPENDIX B

U.S. EXPRESS MAIL NO. TB693235642US

78

```
126   Y    := 0;
127   REPEAT
128     {
129       Mult := Stp - Stp/(iX+1)*iX;
130       Mult := Stp*Stp - (Stp*Mult)/2;
131     }
132     Mult := Pi*(Sqr(Stp*(iX+1))-Sqr(iX*Stp)) / (2.8*Pi*(iX+1));
133     Mult := 4.0E9*Mult / (rhomax2*Pi*rhomax2); { Flächenverhältnis }
134     Mult := Mult*4.0/1000.0  *4;
135     X    := iX * Stp + 0.001;
136     l    := ((LongInt(iY+Mitte) SHL 8 + (iX+Mitte))) SHL 1;
137     Cnt := memW[WArraySeg[l SHR 15] : WArrayOfs[l SHR 15] +
                                                          (l AND $7FFF)];
138     Cnt := Cnt / 64.0 / 4.0;  { SollAbtrag in µm }
139     e   := Cnt * Mult;
140     Cnt := e + Ec;
141     IF Cnt > 0.0 THEN
142        BEGIN
143          Mult2 := (Sqr( (iX+1)*Stp) - Sqr(iX*Stp)) / (Sqr(Stp));
144          Cnt := Cnt*Mult2;
145          i := Round(Cnt+0.5);
146          IF i < 7 THEN i := 0;
147          Cnt := Cnt-i;
148          Cnt := Cnt / Mult2;
149          IF (i+Dat_all.Vektorlaenge) > 2500 THEN
150             BEGIN
151                Fehler := 12;
152                SwapEm;
153                EXIT;
154             END;
155          IF i > 0 THEN
156             BEGIN
157                StartAngle := Random*2*Pi;
158                StepAngle  := Pi*2.0 / i;
159                InnerRing  := Round(iX*Stp*1000);
160             END;
161          IF i >=1 THEN
162          FOR Loop := 1 TO i DO
163             BEGIN
164                INC(Dat_All.Vektorlaenge);
165                WITH Treatment[Dat_All.Vektorlaenge]^ DO
166                   BEGIN
167                      x_pos := Round(InnerRing*Cos(StartAngle) + ErrorX*1E6);
168                      y_pos := Round(Innerring*Sin(StartAngle) + ErrorY*1E6);
169                      StartAngle := StartAngle + StepAngle;
170                      sollblende := Round(rhomax2);
171                      istblende := sollblende;
172                      energie := 100;
173                   END;
174             END;
175       END;
176     Ec := Cnt;
177     INC(iX, 1);
178   UNTIL (Abs(iY) > 126) OR (Abs(iX) > 126);
179 END; {DoDitherCircular}
180
181
182
183 { A slightly different approach of dithering. This procedure works
184   for radial-symmetrical treatments. The procedure just walks from
185   center to the side on a single line. For each step id increases
186   the error as long as it is great enough for at least 8 shots. So
187   this dither method creates rings of 8 shots similar to the
188   HELIX.Search algorithm.
189   Of corse this approach needs a varying correction value depending
190   on the size of the rings.
```

APPENDIX B

U.S. EXPRESS MAIL NO. TB693235642US

```
191}
192 PROCEDURE DoDitherCircular2(VAR rhomax2 : extended; Dir : INTEGER);
193 VAR
194   Mult  : extended;
195   Mult2 : extended;
196   X, Y  : extended;
197   Stp   : extended;
198   Ec    : extended;
199   iX, iY: INTEGER;
200   e, Cnt: extended;
201   Di,DCnt,
202   ECnt  : WORD;
203   i,j   : INTEGER;
204   StartAngle,
205   StepAngle : extended;
206   InnerRing : extended;
207   Loop  : INTEGER;
208 BEGIN
209   IF Fehler > 1 THEN EXIT;
210   Stp  := 15.0/255.0;   { mm per digit }
211   Mult := 4.0E9*Stp*Stp / (rhomax2*Pi*rhomax2); { Flächenverhältnis }
212   Mult := Mult*4.0/1000.0  *4;
213   IF Dir < 0 THEN iX := 120
214               ELSE iX := 0;
215   iY   := 0;
216   Ec   := 0;
217   ECnt := 0;
218   DCnt := 0;
219   Di   := 0;
220   X    := 0;
221   Y    := 0;
222   StartAngle := 0;
223   REPEAT
224     {
225     Mult := Stp - Stp/(iX+1)*iX;
226     Mult := Stp*Stp - (Stp*Mult)/2;
227     }
228     Mult := Pi*(Sqr(Stp*(iX+1))-Sqr(iX*Stp)) / (2.65*Pi*(iX+1));
                                                    { extra correction}
229     Mult := 4.0E9*Mult / (rhomax2*Pi*rhomax2);
                                    { Flächenverhältnis = Ratio of areas}
230     Mult := Mult*4.0/1000.0  *4;
231     X  := iX * Stp;
232     l  := ((LongInt(iY+Mitte) SHL 8 + (iX+Mitte))) SHL 1;
233     Cnt := memW[WArraySeg[l SHR 15] : WArrayOfs[l SHR 15] +
                                                  (l AND $7FFF)];
234     Cnt := Cnt / 64.0 / 4.0;  { SollAbtrag in µm }
235     e   := Cnt * Mult;
236     Cnt := e + Ec;
237     IF Cnt > 0.0 THEN
238       BEGIN
239         Mult2 := (Sqr( (iX+1)*Stp) - Sqr(iX*Stp)) / (Sqr(Stp));
240         Cnt := Cnt*Mult2;
241         i := Round(Cnt+4.5);
242         j := i DIV 8;
243         i := j * 8;
244         IF i < 7 THEN i := 0;
245         IF i > 32 THEN i := 32;
246         Cnt := Cnt-i;
247         Cnt := Cnt / Mult2;
248         j := i DIV 8;
249         IF (i+Dat_all.Vektorlaenge) > 2500 THEN
250           BEGIN
251             Fehler := 12;
252             SwapEm;
253             EXIT;
```

APPENDIX B

U.S. EXPRESS MAIL NO. TB693235642US

```
254           END;
255       WHILE i > 0 DO
256         BEGIN
257           StartAngle := StartAngle+0.1*(256-iX)/50.0;
258           StepAngle  := Pi*2.0 / 8;
259           InnerRing  := Round(iX*Stp*1000 - (Stp/2) + (Stp*((j+1)-(i
      DIV 8))/(j+1)));
260           FOR Loop := 1 TO 8 DO
261             BEGIN
262               INC(Dat_All.Vektorlaenge);
263               WITH Treatment[Dat_All.Vektorlaenge]^ DO
264                 BEGIN
265                   x_pos := Round(InnerRing*Cos(StartAngle) +
                                                       ErrorX*1E6);
266                   y_pos := Round(Innerring*Sin(StartAngle) +
                                                       ErrorY*1E6);
267                   StartAngle := StartAngle + StepAngle;
268                   sollblende := Round(rhomax2);
269                   istblende := sollblende;
270                   energie := 100;
271                 END;
272             END;
273           DEC(i, 8);
274         END;
275       END;
276       Ec := Cnt;
277       INC(iX, Dir);
278     UNTIL (Abs(iY) > 126) OR (Abs(iX) > 126) OR (iX < 0);
279 END; {DoDitherCircular}
280
281
282
283 { Dithering line by line as proposed by Floyd-Steinberg }
284 { Weightening matrix changed                           }
285
286 PROCEDURE DoDitherXY(VAR rhomax2 : extended);
287 VAR
288   Mult  : extended;
289   X, Y  : extended;
290   Stp   : extended;
291   eX,eY : extended;
292   Err   : ARRAY[0..3,-127..127] OF single;
293   Ec    : extended;
294   iX, iY: INTEGER;
295   Cnt,e : extended;
296   Pre   : extended;
297   AddW  : WORD;
298   Maximum: WORD;
299   L1,Loop : WORD;
300   l     : LongInt;
301 BEGIN
302   IF Fehler > 1 THEN EXIT;
303   AddW := 0;
304   (*
305   Maximum := 0;
306   FOR L1 := 0 TO 3 DO
307    FOR Loop := 0 TO 16383 DO
308     BEGIN
309      IF memW[WArraySeg[L1] : WArrayOfs[L1] + Loop shl 1] > Maximum
310      THEN Maximum := memW[WArraySeg[L1] : WArrayOfs[L1] + Loop shl 1];
311     END;
312   AddW := 65535 - Maximum;
313   FOR L1 := 0 TO 3 DO
314    FOR Loop := 0 TO 16383 DO
315     Inc(memW[WArraySeg[L1] : WArrayOfs[L1] + Loop shl 1], AddW);
316   *)
```

```
317  Stp := 15.0/255.0;    { mm per digit }
318  Mult := 4.0E9*Stp*Stp / (rhomax2*Pi*rhomax2);
                                              { <--- Flächenverhältnis }
319                                           { Absolute necessary
correction }
320                                           { with the ratio of the areas. }
321                                           { Not original part of Floyd-St.}
322  Mult := Mult*4.0/1000.0;
323  X    := -120 * Stp + 0.001;
324  Y    := -120 * Stp - 0.001;
325  eX   := -X;
326  eY   := -Y;
327  iX   := -120;
328  iY   := -120;
329  FillChar(Err, SizeOf(Err), 0);
330  Err[1, -122] := -64;
331  NewCirc(Round(rhomax2));
332  REPEAT
333    X  := -120*Stp+0.001;
334    iX := -120;
335    REPEAT
336      l := ((LongInt(iY+Mitte) SHL 8 + (iX+Mitte-1))) SHL 1;
337      Cnt := memW[WArraySeg[l SHR 15] : WArrayOfs[l SHR 15] + (l AND
$7FFF)]-Addw;
338      Cnt := Cnt / 64.0 / 4.0;  { SollAbtrag in µm }
339      Ec := ((Err[3, iX-1] + Err[2, iX  ]) * 8.0    +
340              (Err[2, iX-1] + Err[2, iX+1]) * 5.657 +
341              (Err[3, iX-2] + Err[1, iX  ]) * 4.0   +
342              (Err[2, iX-2] + Err[2, iX+2] + Err[1, iX-1] +
                                               Err[1, iX+1])  * 3.578 +
343              (Err[3, iX-3] + Err[0, iX  ]) * 2.667 +
344              (Err[2, iX-3] + Err[2, iX+3] + Err[0, iX-1] +
                                               Err[0, iX+1])  * 2.530 +
345              (Err[1, iX-2] + Err[1, iX+2])  * 2.828 ) / 70.736;
346      e   := Cnt * Mult;
347      Cnt := e + Ec;
348      WHILE Cnt >= (Mult/2.0) DO
349        BEGIN
350          IF Dat_all.Vektorlaenge < 2500 THEN
351            BEGIN
352              INC(Dat_All.Vektorlaenge);
353              WITH Treatment[Dat_All.Vektorlaenge]^ DO
354                BEGIN
355                  x_pos      := Round(X*1000 + ErrorX*1E6);
356                  y_pos      := Round(Y*1000 + ErrorY*1E6);
357                  sollblende := Round(rhomax2);
358                  istblende  := sollblende;
359                  energie    := 100;
360                END;
361            END
362          ELSE BEGIN
363            Fehler := 12;
364            SwapEm;
365            EXIT;
366          END;
367          Cnt := Cnt-1;
368        END;
369      Err[3, iX] := Cnt;
370      X := X + Stp;
371      INC(iX);
372    UNTIL X > eX;
373    Err[0] := Err[1];
374    Err[1] := Err[2];
375    Err[2] := Err[3];
376    FillChar(Err[3], SizeOf(Err[3]), 0);
377    Y := Y + Stp;
```

APPENDIX B

U.S. EXPRESS MAIL NO. TB693235642US

```
378      INC(iY);
379   UNTIL Y > eY;
380END; {DoDitherXY}
381
382
383
384PROCEDURE OrderDitherXY(VAR Zeile : STRING);
385VAR
386   rhomax2: extended;
387BEGIN
388   IF Fehler > 1 THEN EXIT;
389   Delete(Zeile, 1, 9);          { "DITHERXY(" entfernt }
390   GetNext(Zeile, rhomax2, 500, 7000);
391   IF Fehler > 1 THEN EXIT;
392   CheckEndOfOrder(Zeile);
393   DoDitherXY(rhomax2);
394   IF Fehler=0 THEN Fehler := 1;
395END; {OrderDitherXY}
396
397
398
399PROCEDURE DoDitherC(VAR rhomax2 : extended);
400VAR
401  Mult     : extended;
402   X, Y    : extended;
403   R, Phi  : extended;
404   Stp     : extended;
405   Err     : ARRAY[0..3,0..1023] OF single;
406   ErrS    : ARRAY[0..3] OF single;
407   M       : ARRAY[0..3,-3..3] OF INTEGER;
408   Ec      : extended;
409   iR      : INTEGER;
410   iX, iY  : INTEGER;
411   Cnt,e   : extended;
412   er      : extended;
413   dPhi    : extended;
414   i, j    : INTEGER;
415   iPhi    : INTEGER;
416BEGIN
417   IF Fehler > 1 THEN EXIT;
418   Stp  := 15.0/255.0;    { mm per digit }
419   Mult := 4.0E9*Stp*Stp / (rhomax2*Pi*rhomax2); { Flächenverhältnis }
420   Mult := Mult*4.0/1000.0;
421   iX   := -125;
422   iY   := -125;
423   FillChar(Err, SizeOf(Err), 0);
424   FillChar(ErrS, SizeOf(ErrS), 0);
425   R    := 0;
426   iR   := 0;
427   eR   := Stp*120;
428   Phi  := 0.0;
429   ErrS[1] := 1;
430   ErrS[2] := 1;
431   ErrS[3] := 1;
432   REPEAT
433     {
434     Phi  := 0.0;
435     }
436     ErrS[0] := (R*2.0*Pi / Stp);
437
438     IF ErrS[0] < 1 THEN
439        BEGIN
440           ErrS[0] := 1;
441           dPhi := 4*Pi;
442        END
443        ELSE dPhi := 2.0*Pi / (R*2.0*Pi / Stp);
```

APPENDIX B

U.S. EXPRESS MAIL NO. TB693235642US

```
444    {
445    dPhi := 2.0*Pi / ErrS[0];
446    }
447    iPhi := 0;
448    REPEAT
449      iX := Round(iR * Sin(Phi));
450      iY := Round(iR * Cos(Phi));
451      l := ((LongInt(iY+Mitte) SHL 8 + (iX+Mitte))) SHL 1;
452      Cnt := memW[WArraySeg[l SHR 15] : WArrayOfs[l SHR 15] +
                                                    (l AND $7FFF)];
453      Cnt := Cnt / 64.0 / 4.0;   { SollAbtrag in µm }
454      FOR i := 0 TO 3 DO
455        FOR j := -3 TO 3 DO
456          BEGIN            {iPhi+j)/ErrS[0]}
457            M[i, j] := Round( (Phi+j*dPhi)/(2.0*Pi)*ErrS[i] );
458            WHILE M[i, j] < 0       DO INC(M[i, j], Round(ErrS[i]));
459            WHILE M[i, j] >= ErrS[i] DO DEC(M[i, j], Round(ErrS[i]));
460          END;
461      e  := Cnt * Mult;
462      Ec := ((Err[0, M[0,-1]] + Err[1, M[1, 0]]) * 8.0  +
463             (Err[1, M[1,-1]] + Err[1, M[1,+1]]) * 5.657 +
464             (Err[0, M[0,-2]] + Err[2, M[2, 0]]) * 4.0  +
465             (Err[1, M[1,-2]] + Err[1, M[1,+2]] + Err[2, M[2,-1]] +
                Err[2, M[2,+1]])  * 3.578 +
466             (Err[0, M[0,-3]] + Err[3, M[3, 0]]) * 2.667 +
467             (Err[1, M[1,-3]] + Err[1, M[1,+3]] + Err[3, M[3,-1]] +
                Err[3, M[3,+1]])   * 2.530 +
468             (Err[2, M[2,-2]] + Err[2, M[2,+2]])* 2.828 ) / 70.736;
469      IF iPhi < 3 THEN
470        Ec := Ec * (1.15-(iPhi/20));
471      Cnt := e + Ec;
472      WHILE Cnt > 0.0 DO
473        BEGIN
474          IF Dat_all.Vektorlaenge < 2500 THEN
475            BEGIN
476              INC(Dat_All.Vektorlaenge);
477              WITH Treatment[Dat_All.Vektorlaenge]^ DO
478                BEGIN
479                  x_pos := Round(iR*Stp*Sin(Phi)*1000.0 + ErrorX*1E6);
480                  y_pos := Round(iR*Stp*Cos(Phi)*1000.0 + ErrorY*1E6);
481                  sollblende := Round(rhomax2);
482                  istblende := sollblende;
483                  energie := 100;
484                  IF (Abs(x_pos) > 7500) OR (Abs(y_pos) > 7500) THEN
485                    BEGIN
486                      DEC(Dat_all.Vektorlaenge);
487                      REPEAT
488                        Cnt := Cnt-1.0;
489                      UNTIL Cnt <= 0.0;
490                    END;
491                END;
492            END
493          ELSE BEGIN
494            Fehler := 12;
495            SwapEm;
496            EXIT;
497          END;
498          Cnt := Cnt-1;
499        END;
500      Err[0,M[0,0]] := Cnt;
501      Phi := Phi + dPhi;
502      INC(iPhi);
503    UNTIL Phi >= 2*Pi;
504    Phi := Phi - 2*Pi;
505    ErrS[3]:= ErrS[2];
506    ErrS[2]:= ErrS[1];
```

APPENDIX B

U.S. EXPRESS MAIL NO. TB693235642US

```
507     ErrS[1] := ErrS[0];
508     Err[3] := Err[2];
509     Err[2] := Err[1];
510     Err[1] := Err[0];
511     FillChar(Err[0], SizeOf(Err[0]), 0);
512     R := R + Stp;
513     INC(iR);
514   UNTIL R > eR;
515 END; {DoDitherC}
516
517
518
519 PROCEDURE OrderDitherC(VAR Zeile : STRING);
520 VAR
521   rhomax2: extended;
522 BEGIN
523   IF Fehler > 1 THEN EXIT;
524   Delete(Zeile, 1, 8);          { "DITHERC(" entfernt }
525   GetNext(Zeile, rhomax2, 500, 7000);
526   IF Fehler > 1 THEN EXIT;
527   CheckEndOfOrder(Zeile);
528   DoDitherC(rhomax2);
529   IF Fehler=0 THEN Fehler := 1;
530 END; {OrderDitherC}
531
532
533
534
535 PROCEDURE OrderDither(VAR Zeile : STRING);
536 VAR
537   Typ     : extended;
538   rhomax2 : extended;
539 BEGIN
540   IF Fehler > 1 THEN EXIT;
541   Delete(Zeile, 1, 7);          { "DITHER(" entfernt }
542   GetNext(Zeile, Typ, -0.01, 5.3);
543   IF Fehler > 1 THEN EXIT;
544   GetNext(Zeile, rhomax2, 500, 7000);
545   IF Fehler > 1 THEN EXIT;
546   CheckEndOfOrder(Zeile);
547   CASE Round(Typ) OF
548     0 : DoDitherXY(rhomax2);
549     1 : DoDitherC(rhomax2);
550     2 : DoDitherRect(rhomax2);
551     3 : DoDitherCircular(rhomax2);
552     4 : DoDitherCircular2(rhomax2, 1);
553     5 : DoDitherCircular2(rhomax2, -1);
554   END; {case}
555   IF Fehler=0 THEN Fehler := 1;
556 END; {OrderDither}
```

APPENDIX B

U.S. EXPRESS MAIL NO. TB693235642US

Procedure for sorting shot arrays

```
PROCEDURE OrderSort(VAR Zeile : STRING; Typ : INTEGER);
VAR
  Dist    : ARRAY[0..MaxVektor] OF single;
  Win     : single;
  Loop    : INTEGER;
  Tausch  : BOOLEAN;
  helpse  : shot_event;
  helps   : single;

PROCEDURE Tausche(n, m : WORD);   {exchange shot n with shot m }
      BEGIN
        helpse := Treatment[n]^;
        Treatment[n]^:=Treatment[m]^;
        Treatment[m]^:=helpse;
        helps := Dist[n];
        Dist[n] := Dist[m];
        Dist[m] := helps;
      END;

PROCEDURE SortSpiral;             {sort shots in a spiral }
      VAR
        Loop : INTEGER;
        w    : WORD;
      BEGIN
        REPEAT
          Loop := 2;
          Tausch := FALSE;
          REPEAT
            IF Dist[Loop-1] > Dist[Loop]
              THEN BEGIN
                Tausch := TRUE;
                Tausche(Loop, Loop-1);
              END;
            INC(Loop);
          UNTIL Loop > Dat_all.Vektorlaenge;
        UNTIL NOT(Tausch);
      END;

PROCEDURE SortRandom;             {---------- Random sort }
      VAR
        Loop : INTEGER;
        m, n : WORD;
      BEGIN
        Randomize;
        FOR Loop := 1 TO 5000 DO
          BEGIN
            m := Random(Dat_all.Vektorlaenge)+1;
            n := Random(Dat_all.Vektorlaenge)+1;
            Tausche(m, n);
          END;
      END;

BEGIN
  FOR Loop := 1 TO Dat_all.Vektorlaenge DO
                              { Determine Distance from treatment-}
    BEGIN                     { center for each shot }
      Dist[Loop]:= Sqrt(Sqr(Treatment[Loop]^.x_pos*1.0)+
```

APPENDIX C
U.S. EXPRESS MAIL NO. TB693235642US

```
59                    Sqr(Treatment[Loop]^.y_pos*1.0));
60       IF Treatment[Loop]^.x_pos <> 0
61         THEN BEGIN
62           Win := ArcTan(Treatment[Loop]^.y_pos /
                                          Treatment[Loop]^.x_pos);
63           IF Treatment[Loop]^.x_pos > 0
64             THEN BEGIN
65               IF Win < 0 THEN Win := Win + 2.0*Pi;
66             END
67             ELSE win := Win + Pi;
68         END
69         ELSE BEGIN
70           IF Treatment[Loop]^.y_pos > 0
71             THEN Win := 0
72             ELSE Win := Pi;
73         END;
74         Dist[Loop] := Round(Dist[Loop]/59) + win/(2*Pi);
                            { Add Angle/(2*Pi) to Distance }
75     END;
76   CASE Typ OF
77     0 : SortSpiral;
78     1 : SortRandom;
79   END; {case}
80END; {OrderSort}
```

APPENDIX C

U.S. EXPRESS MAIL NO. TB693235642US

What is claimed is:

1. An apparatus for shaping the cornea by removing tissue from a region of the cornea that has an area to be subject to ablation to a desired treatment pattern, the area having a central point, the apparatus comprising:
   a laser that emits a laser beam having a suitable wavelength;
   an optical system coupled to said laser that receives the laser beam and images the laser beam onto the cornea;
   means coupled to the optical system for directing the optical system to provide the laser beam at a fixed spot size on the cornea, wherein the fixed spot size is a relatively large fraction of the area of the cornea to be subject to ablation; and
   means coupled to the laser and the means for directing the optical system for directing said laser to fire the laser beam and the optical system to image the laser beam in a series of shots at said fixed spot size, said series of shots including shots being centered at at least two distances from the central point, said series of shots including shots partially overlapping with prior shots, and said series of shots ablating the cornea to the desired treatment pattern, wherein said means for directing the optical system to provide the laser beam at a fixed spot size further comprises means for providing the laser beam at a spot size fixed between 2.0 mm and 3.5 mm in diameter.

2. A method of controlling a laser system, the laser system including a laser that emits a laser beam having a suitable wavelength and the laser system including an optical system that images the laser beam onto a cornea that has an area to be subject to ablation to a desired treatment pattern, the area having a central point, the method comprising the steps of:
   calculating a shot sequence to ablate the cornea to the desired treatment pattern;
   sorting said calculated shot sequence; and
   directing the laser system to fire the laser beam in a series of shots, said series of shots corresponding to and fired in order of said sorted calculated shot sequence,
   wherein said sorting step further comprises the step of randomly sorting said calculated shot sequence.

3. The method of claim 2, wherein said sorting step further comprises the step of sorting said calculated shot sequence into a spiral.

4. A method of controlling a laser system, the laser system including a laser that emits a laser beam having a suitable wavelength and the laser system including an optical system that images the laser beam onto a cornea that has an area to be subject to ablation to a desired treatment pattern, the area having a central point, the method comprising the steps of:
   directing the laser system to provide the laser beam at a fixed spot size on the cornea, wherein the fixed spot size is a relatively large fraction of the area of the cornea to be subject to ablation; and
   directing the laser system to fire the laser beam in a series of shots at said fixed spot size, said series of shots including shots being centered at at least two distances from the central point, said series of shots including shots partially overlapping with prior shots, and said series of shots ablating the cornea to the desired treatment pattern,
   wherein said step of directing the laser system to provide the laser beam at a fixed spot size further comprises the step of directing the laser system to provide the laser beam at a spot size fixed between 2.0 mm and 3.5 mm in diameter.

5. The method of claim 4, wherein said step of directing the laser system to fire the laser beam in a series of shots being centered at least two distances from the central point further comprises the steps of:
   directing the laser system to fire a series of overlapping shots forming a ring having a first radius from the central point; and
   directing the laser system to fire a series of overlapping shots forming a ring having a second radius from the central point.

6. The method of claim 4, wherein said step of directing the laser system to fire a series of partially overlapping shots includes the step of:
   firing a first shot;
   firing a second shot not overlapping said first shot; and
   firing a third shot partially overlapping said first shot.

7. The method of claim 4, wherein said step of directing the laser system to fire the laser beam in a series of shots further comprises the steps of:
   dividing the series of shots among a plurality of rings; and
   empirically calculating a radius for each of said plurality of rings to satisfy the desired treatment pattern.

8. The method of claim 4, wherein said step of directing the laser system to fire the laser beam in a series of shots further comprises the steps of:
   calculating a shot dithering pattern corresponding to the desired treatment pattern; and
   directing the laser system to fire the laser beam with the series of shots corresponding to said shot dithering pattern.

9. The method of claim 8, wherein said calculating step further comprises calculating a rectangular shot dithering pattern.

10. The method of claim 8, wherein said calculating step further comprises calculating a circular shot dithering pattern.

11. The method of claim 8, wherein said calculating step further comprises calculating a line-by-line shot dithering pattern.

12. The method of claim 8 further comprising the step of:
   after said calculating step, sorting said calculated shot dithering pattern.

13. The method of claim 12, wherein said sorting step further comprises the step of randomly sorting said calculated shot dithering pattern.

14. The method of claim 12, wherein said sorting step further comprises the step of sorting said calculated shot dithering pattern into a spiral.

15. A method of controlling a laser system, the laser system including a laser that emits a laser beam having a suitable wavelength and the laser system including an optical system that images the laser beam onto a cornea that has an area to be subject to ablation to a desired treatment pattern, the area having a central point, the method comprising the steps of:
   directing the laser system to provide the laser beam at a fixed spot size on the cornea, wherein the fixed spot size is a relatively large fraction of the area of the cornea to be subject to ablation; and
   directing the laser system to fire the laser beam in a series of shots at said fixed spot size, said series of shots including shots being centered at at least two distances from the central point, said series of shots including shots partially overlapping with prior shots, and said series of shots ablating the cornea to the desired treatment pattern, wherein said step of directing the laser system to fire the laser beam in a series of shots further comprises the steps of:
 dividing the series of shots among a plurality of rings; and
 empirically calculating a radius for each of said plurality of rings to satisfy the desired treatment pattern.

16. A method of controlling a laser system, the laser system including a laser that emits a laser beam having a suitable wavelength and the laser system including an optical system that images the laser beam onto a cornea that has an area to be subject to ablation to a desired treatment pattern, the area having a central point, the method comprising the steps of:
 directing the laser system to provide the laser beam at a fixed spot size on the cornea, wherein the fixed spot size is a relatively large fraction of the area of the cornea to be subject to ablation; and
 directing the laser system to fire the laser beam in a series of shots at said fixed spot size, said series of shots including shots being centered at at least two distances from the central point, said series of shots including shots partially overlapping with prior shots, and said series of shots ablating the cornea to the desired treatment pattern, wherein said step of directing the laser system to fire the laser beam in a series of shots further comprises the steps of:
 calculating a shot dithering pattern corresponding to the desired treatment pattern; and
 directing the laser system to fire the laser beam with the series of shots corresponding to said shot dithering pattern.

17. The method of claim 16, wherein said calculating step further comprises calculating a rectangular shot dithering pattern.

18. The method of claim 16, wherein said calculating step further comprises calculating a circular shot dithering pattern.

19. The method of claim 16, wherein said calculating step further comprises calculating a line-by-line shot dithering pattern.

20. The method of claim 16 further comprising the step of:
 after said calculating step, sorting said calculated shot dithering pattern.

21. The method of claim 20, wherein said sorting step further comprises the step of randomly sorting said calculated shot dithering pattern.

22. The method of claim 20, wherein said sorting step further comprises the step of sorting said calculated shot dithering pattern into a spiral.

23. A method of controlling a laser system, the laser system including a laser that emits a laser beam having a suitable wavelength and the laser system including an optical system that images the laser beam onto a cornea that has an area to be subject to ablation to a desired treatment pattern, the area having a central point, the method comprising the steps of:
 directing the laser system to provide the laser beam at a fixed spot size on the cornea, wherein the fixed spot size is a relatively large fraction of the area of the cornea to be subject to ablation; and
 directing the laser system to fire the laser beam in a series of shots at said fixed spot size, said series of shots including shots being centered at at least two distances from the central point, said series of shots including shots partially overlapping with prior shots, and said series of shots ablating the cornea to the desired treatment pattern, wherein said step of directing the laser system to fire a series of partially overlapping shots includes the step of:
 firing a first shot;
 firing a second shot not overlapping said first shot; and
 firing a third shot partially overlapping said first shot.

* * * * *